United States Patent
Atkinson et al.

(10) Patent No.: US 10,471,050 B2
(45) Date of Patent: Nov. 12, 2019

(54) 2-OXO-1,2-DIHYDROPYRIDINE-3,5-DICARBOXAMIDE COMPOUNDS AS BROMODOMAIN INHIBITORS

(71) Applicant: GlaxoSmithKline Intellectual Property (No. 2) Limited, Brentford, Middlesex (GB)

(72) Inventors: Stephen John Atkinson, Stevenage (GB); Emmanuel Hubert Demont, Stevenage (GB); Lee Andrew Harrison, Stevenage (GB); Thomas George Christopher Hayhow, Stevenage (GB); Matthew J. Lindon, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GLAXOSMITHKLINE INTELLECTUAL PROPERTY (NO.2) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/766,222

(22) PCT Filed: Oct. 3, 2016

(86) PCT No.: PCT/EP2016/073532
§ 371 (c)(1),
(2) Date: Apr. 5, 2018

(87) PCT Pub. No.: WO2017/060180
PCT Pub. Date: Apr. 13, 2017

(65) Prior Publication Data
US 2018/0280368 A1 Oct. 4, 2018

Related U.S. Application Data

(60) Provisional application No. 62/237,002, filed on Oct. 5, 2015.

(51) Int. Cl.
| | | |
|---|---|---|
| C07D 401/14 | (2006.01) | |
| A61K 31/4412 | (2006.01) | |
| C07D 213/82 | (2006.01) | |
| C07D 401/12 | (2006.01) | |
| A61P 37/06 | (2006.01) | |
| A61K 31/4439 | (2006.01) | |

(52) U.S. Cl.
CPC ...... *A61K 31/4412* (2013.01); *A61K 31/4439* (2013.01); *A61P 37/06* (2018.01); *C07D 213/82* (2013.01); *C07D 401/12* (2013.01); *C07D 401/14* (2013.01)

(58) Field of Classification Search
CPC .................................................. A61K 31/4412
See application file for complete search history.

(56) References Cited

U.S. PATENT DOCUMENTS

| 2012/0208814 A1 | 8/2012 | Demont et al. |
| 2014/0179648 A1 | 6/2014 | Liu et al. |

FOREIGN PATENT DOCUMENTS

| EP | 1 357 111 B1 | 10/2003 |
| EP | 1 433 788 A1 | 6/2004 |
| EP | 1 477 186 A1 | 11/2004 |
| WO | WO 2004/033446 A1 | 4/2004 |
| WO | WO 2014/074675 A1 | 5/2014 |
| WO | WO 2014/096965 A2 | 6/2014 |
| WO | WO 2015/015318 A2 | 2/2015 |
| WO | WO 2017/037116 A1 | 3/2017 |
| WO | WO 2017/060180 A1 | 4/2017 |
| WO | WO 2017/174621 A1 | 10/2017 |
| WO | WO 2017/202742 A1 | 11/2017 |

OTHER PUBLICATIONS

Dittmer et al., Journal of Organic Chemistry (1973), 38(16), 2873-82.*
Dittmer et al., "Models for the Pyridine Nucleotide Coenzymes. Synthesis and Properties of Bridged Dinicotinamide Derivatives[1-3]", *J. Org. Chem.*, vol. 38, No. 16, pp. 2873-2882 (1973).
Gallenkamp et al., "Bromodomains and Their Pharmacological Inhibitors", *ChemMedChem*, vol. 9, No. 3, pp. 438-464 (2014).
Garnier et al., "BET bromodomain inhibitors: a patent review", *Expert Opinion on Therapeutic Patents*, vol. 24, No. 2, pp. 185-199 (2014).
International Search Report for International application No. PCT/EP2016/070519, dated Oct. 20, 2016, 4 pages.
International Search Report for International application No. PCT/EP2016/072216, International filing date: Sep. 20, 2016, 3 pages.
International Search Report for International application No. PCT/EP2016/073532, dated Nov. 30, 2016, 5 pages.

(Continued)

*Primary Examiner* — Paul V Ward
(74) *Attorney, Agent, or Firm* — Jane F. Djung; Duke M. Fitch; Edward R. Gimmi

(57) ABSTRACT

The present invention relates to compounds of formula (I) and salts thereof, pharmaceutical compositions containing such compounds and to their use in therapy.

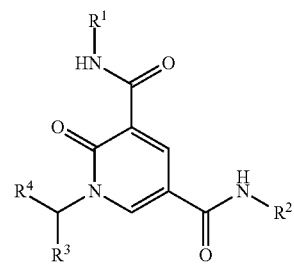

21 Claims, No Drawings

(56) References Cited

OTHER PUBLICATIONS

International Search Report for International application No. PCT/EP2017/058050, dated May 24, 2017, 5 pages.
International Search Report for International application No. PCT/EP2017/062208, dated Jul. 6, 2017, 5 pages.
International Search Report for International application No. PCT/EP2018/054730, dated May 4, 2018, 4 pages.
International Search Report for International application No. PCT/EP2018/054733, dated Jun. 11, 2018, 4 pages.
Notice of Allowance for U.S. Appl. No. 15/762,229, USPTO, dated Dec. 11, 2018, 9 pages.
Notice of Allowance for U.S. Appl. No. 15/762,229, USPTO, dated Mar. 20, 2019, 9 pages.
Restriction Requirement for U.S. Appl. No. 15/757,199, USPTO, dated Feb. 11, 2019, 9 pages.

* cited by examiner

2-OXO-1,2-DIHYDROPYRIDINE-3,5-DICARBOXAMIDE COMPOUNDS AS BROMODOMAIN INHIBITORS

This application is a § 371 of International Application No. PCT/EP2016/073532, filed 3 Oct. 2016, which claims the benefit of U.S. Provisional Application No. 62/237,002, filed 5 Oct. 2015, which are incorporated herein in their entireties.

FIELD OF THE INVENTION

The present invention is directed to certain compounds which are bromodomain inhibitors, processes for their preparation, pharmaceutical compositions comprising the compounds and the use of the compounds or the compositions in the treatment of various diseases or conditions. Compounds which are bromodomain inhibitors may be useful in the treatment of various diseases and conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.*, 2011, 54, 3827-3838).

Chan et al. report that BET bromodomain inhibition suppresses transcriptional responses to cytokine-Jak-STAT signalling in a gene-specific manner in human monocytes, which suggests that BET inhibition reduces inflammation partially through suppression of cytokine activity. (Chan et al., *Eur. J. Immunol.*, 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.*, 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. *Nature Communications*, 2014, 5, 5418).

Funabashi et al describe 1,2,3,4,-tetrahydroquinolines and conduct a configuration and conformation analysis (Funabashi et al, *Bulletin of the Chemical Society of Japan*, 1969, 42, 2885-2894).

WO2014/140076 discloses 2,3-disubstituted 1-acyl-4-amino-1,2,3,4-tetrahydroquinoline derivatives and their use as bromodomain inhibitors.

SUMMARY OF THE INVENTION

The present invention relates to a compound of formula (I)

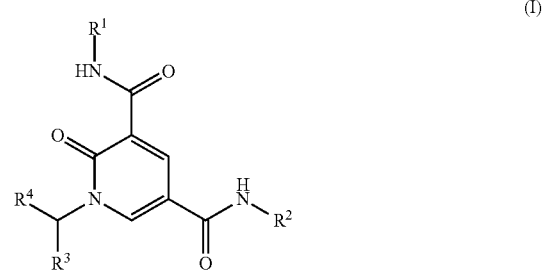

or a salt thereof
wherein
$R^1$ is $C_{1-3}$alkyl or cyclopropyl;
$R_2$ is —$CH_3$, $C_{2-6}$alkyl optionally substituted by up to five fluoro, —$C_{2-6}$alkylOR$^5$, —$C_{2-6}$alkylNR$^5$R$^6$, —$(CH_2)_m SO_2 C_{1-3}$alkyl, —$(CH_2)_m C(O)NR^5R^6$, —$(CH_2)_m CN$, —$(CH_2)_m CO_2 R^5$, —$(CH_2)_m NHCO_2 C(CH_3)_3$ or —$(CH_2)_n C_{5-6}$heteroaryl wherein $C_{5-6}$heteroaryl is optionally substituted by one or two substituents independently selected from halo, $C_{1-4}$alkyl, $C_{3-4}$cycloalkyl and —OR$^5$;
$R^3$ is a) phenyl (which may be unsubstituted or substituted by one, two or three R$^9$ groups which may be the same or different); b) a $C_{5-6}$heteroaryl group (which may be unsubstituted or substituted by $C_{1-3}$alkyl, $C_{3-4}$cycloalkyl, $C_{1-3}$alkoxy or halo); c) a $C_{9-11}$heteroaryl group (which may be unsubstituted or substituted by one, two or three groups independently selected from —$C_{1-3}$alkylR$^{10}$, —OCH$_3$, —OCHF$_2$, —OCF$_3$, —OC$_{2-3}$alkylR$^{10}$, halo, oxo and —CN); or d) —$(CH_2)_q$-phenyl;
$R^4$ is —H, $C_{1-4}$alkyl, cyclopropyl, —$CH_2$OR$^{11}$ or —$CH_2CH_2$OR$^{11}$;

$R^5$ and $R^6$ are each independently selected from —H, $C_{1-3}$alkyl and $C_{2-4}$alkyl$OC_{0-3}$alkyl;

$R^9$ is —$NR^{12}R^{13}$, fluoro, —CN, —$CH_2CN$, —$CO_2R^{11}$, —$C(O)C_{1-3}$alkyl, —OH, —$OCHF_2$, —$OCF_3$, —$O$—$C_{2-6}$alkyl$R^{10}$, —$OCH_3$, —$OCH_2CH_2NR^{12}R^{13}$, —$C_{1-6}$alkyl$R^{10}$, —$OC_{4-7}$heterocyclyl, —$OCH_2C_{4-7}$heterocyclyl, —$CH_2C_{4-7}$heterocyclyl, —$CH_2CH_2C_{4-7}$heterocyclyl, —$NHC(O)R^{11}$, —$SO_2R^{11}$ or —$SOR^{11}$;

$R^{10}$ is —H, —$OR^{11}$ or —$NR^{12}R^{13}$;

$R^{11}$ is —H or $C_{1-3}$alkyl;

$R^{12}$ and $R^{13}$ are each independently selected from —H and $C_{1-3}$alkyl; or $R^{12}$ and $R^{13}$ may join together with the nitrogen to which they are attached, to form a $C_{4-7}$heterocyclyl optionally containing a further heteroatom selected from nitrogen, oxygen and sulphur and optionally substituted by one or two substituents independently selected from $C_{1-3}$alkyl, —OH and fluoro;

m is an integer selected from 2, 3 and 4;

n is an integer selected from 0, 1, 2, 3 and 4; and q is an integer selected from 1 and 2.

Certain compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis. Accordingly, the invention is further directed to pharmaceutical compositions comprising a compound of formula (I), or a pharmaceutically acceptable salt thereof. The invention is still further directed to methods of treatment of diseases or conditions associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

Compounds of formula (I) and salts thereof are referred to herein as "compounds of the invention".

"BD2" refers to Binding Domain 2 of any of the BET family of proteins BRD2, BRD3, BRD4 or BRDT.

"Alkyl" refers to a saturated hydrocarbon chain having the specified number of carbon atoms. For example, the term "$C_{1-6}$alkyl" as used herein refers to a straight or branched alkyl group having from 1 to 6 carbon atoms, for example 1 to 3 carbon atoms. For example the term "$C_{0-3}$alkyl" refers to a straight or branched alkyl group having from 0 (i.e. is absent) to 3 carbon atoms, for example 0 to 2 carbon atoms. Representative branched alkyl groups have one, two or three branches. "Alkyl" includes, but is not limited to, methyl, ethyl, n-propyl, n-butyl, iso-butyl, iso-propyl, t-butyl, pentyl and hexyl.

"Cycloalkyl" refers to a saturated hydrocarbon ring or a saturated spiro-linked bicyclic hydrocarbon ring, having the specified number of member atoms in the ring. For example, the term "$C_{3-4}$cycloalkyl" as used herein refers to a cycloakyl group having from 3 to 4 member atoms, for example 3 member atoms. Examples of $C_{3-4}$cycloalkyl groups include, but are not limited to, cyclopropyl and cyclobutyl.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, "enantiomerically enriched" refers to products whose enantiomeric excess is greater than 50% ee, greater than 75% ee, and greater than 90% ee.

"Enantiomerically pure" as used herein refers to products whose enantiomeric excess is 99% or greater.

"Half-life" (or "half-lives") refers to the time required for half of a quantity of a substance to be converted to another chemically distinct species in vitro or in vivo.

"Halo" refers to a halogen radical, for example, fluoro, chloro, bromo, or iodo.

"Heteroaryl" refers to a cyclic or bicyclic group having the specified number of member atoms wherein at least a portion of the group is aromatic. The point of attachment to the rest of the molecule may be by any suitable carbon or nitrogen atom. For example, the term "$C_{5-6}$heteroaryl" as used herein refers to a heteroaryl group having 5 or 6 member atoms, including 1 or 2 heteroatoms independently selected from nitrogen, sulphur and oxygen. Examples of "$C_{5-6}$membered heteroaryl" groups include, but are not limited to, imidazolyl, pyrazolyl and pyridinyl. The term "$C_{9-11}$heteroaryl" as used herein refers to a bicyclic structure having 9, 10 or 11 member atoms, including 1 or 2 heteroatoms independently selected from nitrogen and oxygen. Examples of "$C_{9-11}$heteroaryl" groups include, but are not limited to, 2,3-dihydrobenzo[b][1,4]dioxinyl, 1H-benzo[d]imidazolyl, benzoimidazolyl, benzazepinyl, 2,3,4,5-tetrahydro-1H-benzo[d]azepinyl, quinoxalinyl, quinolinyl, indazolyl, indolyl, 1,2,3,4-tetrahydroquinolinyl, 1,2,3,4-tetrahydroisoquinolinyl, indolinyl, benzofuranyl, isoquinolinyl and 2,3-dihydrobenzofuranyl.

"Heteroatom" refers to a nitrogen, sulfur, or oxygen atom, for example a nitrogen atom or an oxygen atom.

"Heterocyclyl" refers to an aliphatic cyclic group having the specified number of member atoms. The point of attachment may be by any suitable carbon or nitrogen atom. For example the term "$C_{4-7}$heterocyclyl" as used herein refers to a heterocycle group having 4, 5, 6 or 7 member atoms including one heteroatom which is nitrogen and optionally containing a further heteroatom selected from nitrogen, oxygen and sulphur. Examples of "$C_{4-7}$heterocyclyl" groups include, but are not limited to azetidinyl, pyrrolidinyl, piperidinyl, piperazinyl, morpholinyl and azepanyl. Examples of "$C_6$heterocyclyl" groups include, but are not limited to, piperidinyl, piperazinyl and morpholinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable e.g. of sufficiently high purity.

"rac" refers to the racemic mixture of the compounds of formula (I). For example, "rac-(2S,3R,4R)" means a racemic mixture of the (2S,3R,4R) enantiomer and the (2R,3S,4S) enantiomer.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The compounds of the invention may exist in solvated or non-solvated form.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where diastereoisomers are represented and only the relative stereochemistry is referred to, the bold or hashed solid bond symbols (━/⋯⋯) are used. Where the absolute stereochemistry is known and the compound is a single enantiomer, the bold or hashed wedges symbols (━/⋯⋯) are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that the invention includes solvates, isomers and polymorphic forms of the compounds of formula (I) and salts thereof.

In a first aspect there are provided compounds of formula (I):

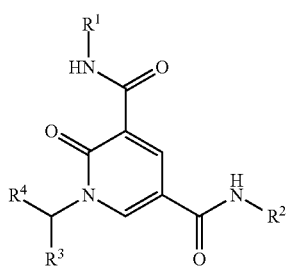
(I)

or a salt thereof wherein
$R^1$ is $C_{1-3}$alkyl or cyclopropyl;
$R_2$ is —$CH_3$, $C_{2-6}$alkyl optionally substituted by up to five fluoro, —$C_{2-6}$alkylOR$^5$, —$C_{2-6}$alkylNR$^5$R$^6$, —$(CH_2)_m SO_2 C_{1-3}$alkyl, —$(CH_2)_m C(O)NR^5R^6$, —$(CH_2)_m CN$, —$(CH_2)_m CO_2 R^5$, —$(CH_2)_m NHCO_2 C(CH_3)_3$ or —$(CH_2)_n C_{5-6}$heteroaryl wherein $C_{5-6}$heteroaryl is optionally substituted by one or two substituents independently selected from halo, $C_{1-4}$alkyl, $C_{3-4}$cycloalkyl and —OR$^5$;
$R^3$ is a) phenyl (which may be unsubstituted or substituted by one, two or three $R^9$ groups which may be the same or different); b) a $C_{5-6}$heteroaryl group (which may be unsubstituted or substituted by $C_{1-3}$alkyl, $C_{3-4}$cycloalkyl, $C_{1-3}$alkoxy or halo); c) a $C_{9-11}$heteroaryl group (which may be unsubsituted or substituted by one, two or three groups independently selected from —$C_{1-3}$alkylR$^{10}$, —OCH$_3$, —OCHF$_2$, —OCF$_3$, —OC$_{2-3}$alkylR$^{10}$, halo, oxo and —CN); or d) —$(CH_2)_q$-phenyl;
$R^4$ is —H, $C_{1-4}$alkyl, cyclopropyl, —CH$_2$OR$^{11}$ or —CH$_2$CH$_2$OR$^{11}$;
$R^5$ and $R^6$ are each independently selected from —H, $C_{1-3}$alkyl and $C_{2-4}$alkylOC$_{0-3}$alkyl;
$R^9$ is —NR$^{12}$R$^{13}$, fluoro, —CN, —CH$_2$CN, —CO$_2$R$^{11}$, —C(O)C$_{1-3}$alkyl, —OH, —OCHF$_2$, —OCF$_3$, —O—C$_{2-6}$alkylR$^{10}$, —OCH$_3$, —OCH$_2$CH$_2$NR$^{12}$R$^{13}$, —C$_{1-6}$alkylR$^{10}$, —OC$_{4-7}$heterocyclyl, —OCH$_2$C$_{4-7}$heterocyclyl, —CH$_2$C$_{4-7}$heterocyclyl, —CH$_2$CH$_2$C$_{4-7}$heterocyclyl, —NHC(O)R$^{11}$, —SO$_2$R$^{11}$ or —SOR$^{11}$;
$R^{10}$ is —H, —OR$^{11}$ or —NR$^{12}$R$^{13}$;
$R^{11}$ is —H or $C_{1-3}$alkyl;
$R^{12}$ and $R^{13}$ are each independently selected from —H and $C_{1-3}$alkyl; or $R^{12}$ and $R^{13}$ may join together with the nitrogen to which they are attached, to form a $C_{4-7}$heterocyclyl optionally containing a further heteroatom selected from nitrogen, oxygen and sulphur and optionally substituted by one or two substituents independently selected from $C_{1-3}$alkyl, —OH and fluoro;
m is an integer selected from 2, 3 and 4;
n is an integer selected from 0, 1, 2, 3 and 4; and
q is an integer selected from 1 and 2.

In one embodiment there is provided compounds of formula (I) or a salt thereof wherein
$R^1$ is $C_{1-3}$alkyl or cyclopropyl;
$R_2$ is —$CH_3$, $C_{2-6}$alkyl optionally substituted by up to five fluoro, —$C_{2-6}$alkylOR$^5$, —$C_{2-6}$alkylNR$^5$R$^6$, —$(CH_2)_m SO_2 C_{1-3}$alkyl, —$(CH_2)_m C(O)NR^5R^6$, —$(CH_2)_m CN$, —$(CH_2)_m CO_2 R^5$, —$(CH_2)_m NHCO_2 C(CH_3)_3$ or —$(CH_2)_n C_{5-6}$heteroaryl wherein $C_{5-6}$heteroaryl is optionally substituted by one or two substituents independently selected from halo, $C_{1-4}$alkyl, $C_{3-4}$cycloalkyl and —OR$^5$;
$R^3$ is a) phenyl (which may be unsubstituted or substituted by one, two or three $R^9$ groups which may be the same or different); b) a $C_{5-6}$heteroaryl group (which may be unsubstituted or substituted by $C_{1-3}$alkyl, $C_{3-4}$cycloalkyl, $C_{1-3}$alkoxy or halo); c) a $C_{9-11}$heteroaryl group (which may be unsubsituted or substituted by one, two or three groups independently selected from —$C_{1-3}$alkylR$^{10}$, —OCH$_3$, —OCHF$_2$, —OCF$_3$, —OC$_{2-3}$alkylR$^{10}$, halo, oxo and —CN); or d) —$(CH_2)_q$-phenyl;
$R^4$ is —H, $C_{1-4}$alkyl, cyclopropyl, —CH$_2$OR$^{11}$ or —CH$_2$CH$_2$OR$^{11}$;
$R^5$ and $R^6$ are each independently selected from —H, $C_{1-3}$alkyl and $C_{2-4}$alkylOC$_{0-3}$alkyl;
$R^7$ and $R^8$ are each independently selected from —H and $C_{1-3}$alkyl; or $R^7$ and $R^8$ may join together with the nitrogen to which they are attached, to form a $C_{4-7}$heterocyclyl optionally containing a further heteroatom selected from nitrogen, oxygen and sulphur and optionally substituted by one or two substituents independently selected from $C_{1-3}$alkyl, —OH and fluoro;

$R^9$ is —$NR^{12}R^{13}$, fluoro, oxo, —CN, —$CH_2CN$, —$CO_2R^{11}$, —$C(O)C_{1-3}$alkyl, —OH, —$OCHF_2$, —$OCF_3$, —O—$C_{2-6}$alkyl$R^{10}$, —$OCH_3$, —$OCH_2CH_2NR^{12}R^{13}$, —$OC_6$heterocyclyl, —$OCH_2C_6$heterocyclyl, —$CH_2C_6$heterocyclyl, —$CH_2CH_2C_6$heterocyclyl, —NHC(O)$R^{11}$, —$SO_2R^{11}$ or —$SOR^{11}$;

$R^{10}$ is —H, —$OR^{11}$ or —$NR^{12}R^{13}$;

$R^{11}$ is —H or $C_{1-3}$alkyl;

$R^{12}$ and $R^{13}$ are each independently selected from —H and $C_{1-3}$alkyl; or $R^{12}$ and $R^{13}$ may join together with the nitrogen to which they are attached, to form a $C_{4-7}$heterocyclyl optionally containing a further heteroatom selected from nitrogen, oxygen and sulphur and optionally substituted by one or two substituents independently selected from $C_{1-3}$alkyl, —OH and fluoro;

m is an integer selected from 2, 3 and 4;

n is an integer selected from 2, 3 and 4; and q is an integer selected from 1 and 2.

In one embodiment there are provided compounds of formula (Ia):

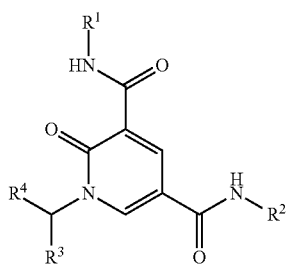

(Ia)

or a salt thereof
wherein
$R^1$ is methyl or cyclopropyl;

$R^2$ is methyl, ethyl, iso-propyl, n-propyl, butyl, —$CH_2CH_2CH(CH_3)_2$, —$CH_2CH(CH_3)_2$, —$CH_2CH_2CH_2C(O)NHCH_3$, —$CH_2CH_2CH_2NHCO_2C(CH_3)_3$, —$CH_2CH_2CH_2CO_2CH_3$, —$CH_2CH_2OH$, —$CH_2CH_2CH_2OH$, —$CH_2CH_2CH_2CN$, —$CH_2CH_2CN$, —$CH_2CH_2CH_2NH_2$, —$CH_2CH_2CF_3$, —$CH_2CH(CH_3)OH$, —$CH_2CH_2CH(CH_3)OH$, —$CH_2CH(CH_3)OCH_3$, —$CH_2CH_2OCH_3$, —$CH_2CH_2CH_2OCH_3$, —$CH_2CH_2CH_2CO_2H$, —$CH_2CH_2CH(CH_3)N(CH_3)_2$, —$CH_2CH_2CH_2N(CH_3)_2$, —$CH_2CH_2C(O)NHCH_3$, —$CH_2CH_2SO_2CH_3$, —$CH_2CH_2CH_2SO_2CH_3$, —$CH_2CH_2$-imidazolyl, —$CH_2CH_2$-pyridinyl or —$CH_2CH_2$-pyrazolyl;

$R^3$ is a) phenyl (which may be unsubstituted or substituted by one or two groups which may be the same or different selected from methyl, —$OCH_3$, —$OCH_2CH_2OH$, fluoro and —CN); or c) unsubstituted indolyl; and $R^4$ is —H or methyl;

In one embodiment $R^1$ is methyl, ethyl or cyclopropyl. In another embodiment $R^1$ is methyl.

In one embodiment $R^2$ is selected from methyl, ethyl, propyl, iso-propyl, butyl, —$CH_2CH_2CH(CH_3)_2$, —$CH_2CH(CH_3)_2$, —$CH_2CH_2OR^5$, —$CH_2CH_2CH_2OR^5$, —$CH_2CH(CH_3)OR^5$, —$CH_2CH_2CH(CH_3)OR^5$, —$CH_2CH_2CH(CH_3)NR^5R^6$, —$CH_2CH_2CH_2NR^5R^6$, —$(CH_2)_mSO_2CH_3$, —$(CH_2)_mC(O)NHCH_3$, —$(CH_2)_mCN$, —$(CH_2)_mCO_2R^5$, —$(CH_2)_mCF_3$ and —$(CH_2)_mNHCO_2C(CH_3)_3$. In another embodiment $R^2$ is —$C_{1-6}$alkyl selected from methyl, ethyl, propyl, iso-propyl, butyl, —$CH_2CH_2CH(CH_3)_2$ and —$CH_2CH(CH_3)_2$. In another embodiment $R^2$ is —$C_{1-6}$alkyl$OR^5$ selected from —$CH_2CH_2OR^5$, —$CH_2CH_2CH_2OR^5$, —$CH_2CH(CH_3)OR^5$ and —$CH_2CH_2CH(CH_3)OR^5$. In another embodiment $R^2$ is —$C_{1-6}$alkyl$NR^5R^6$ selected from —$CH_2CH_2CH(CH_3)NR^5R^6$ and —$CH_2CH_2CH_2NR^5R^6$. In another embodiment $R^2$ is —$(CH_2)_mSO_2CH_3$. In another embodiment $R^2$ is —$(CH_2)_mC(O)NHCH_3$. In another embodiment $R^2$ is —$(CH_2)_mCN$. In another embodiment $R^2$ is —$(CH_2)_mCO_2R^5$. In another embodiment $R^2$ is —$(CH_2)_mCF_3$. In another embodiment $R^2$ is —$(CH_2)_mNHCO_2C(CH_3)_3$. In another embodiment $R^2$ is —$(CH_2)_nC_{5-10}$heteroaryl wherein the $C_{5-10}$heteroaryl is imidazolyl, pyridinyl or pyrazolyl. In a further embodiment $R^2$ is selected from:

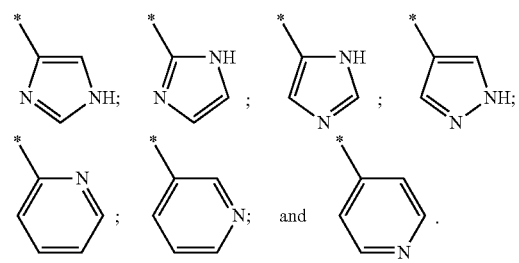

wherein * denotes the point of attachment to the alkyl residue.

In another embodiment there is provided compounds of formula (I) in which $R^2$ is —$(CH_2)_nC_{5-10}$heteroaryl wherein the $C_{5-10}$heteroaryl is imidazolyl, pyridinyl, pyrazolyl, pyridazinyl, isoxazolyl, thiazolyl or triazolyl said groups being optionally substituted by $C_{1-4}$alkyl.

In one embodiment $R^3$ is phenyl optionally substituted by one or two $R^9$ groups selected from fluoro, —CN, —$OCH_3$ and —$OC_{1-6}$alkyl$R^{10}$. In another embodiment $R^3$ is phenyl optionally substituted by one or two $R^9$ groups selected from fluoro, —CN, —$OCH_3$ and —$OCH_2CH_2OH$. In another embodiment $R^3$ is unsubstituted phenyl. In another embodiment $R^3$ is unsubstituted indolyl. In another embodiment $R^3$ is selected from:

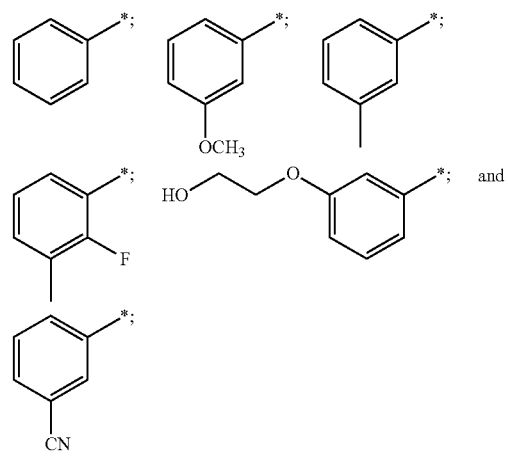

wherein * denotes the point of attachment to the alkyl residue.

In another embodiment $R_3$ is

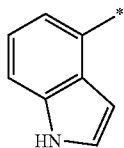

wherein * denotes the point of attachment to the alkyl residue.

In one embodiment $R^4$ is —H or methyl. In another embodiment $R^4$ is —H. In a further embodiment $R^4$ is methyl.

In one embodiment $R^5$ is —H or methyl. In another embodiment $R^5$ is —H. In a further embodiment $R^5$ is methyl.

In one embodiment $R^6$ is —H or methyl. In another embodiment $R^6$ is —H. In a further embodiment $R^6$ is methyl.

In one embodiment both $R^5$ and $R^6$ are —H. In another embodiment both $R^5$ and $R^6$ are methyl.

In one embodiment $R^7$ and $R^8$ are each independently selected from —H and methyl.

In another embodiment $R^7$ and $R^8$ join together with the nitrogen atom to which they are attached, to form a $C_{4-7}$heterocyclyl selected from azetidinyl, pyrrolidinyl, piperidinyl, piperazinyl, morpholinyl and azepanyl optionally substituted by one or two substituents independently selected from —$C_{1-3}$alkyl, —OH and fluorine.

In one embodiment $R^9$ is —$NR^{12}R^{13}$, fluoro, —CN, —$CH_2CN$, —$CO_2R^{11}$, —$C(O)C_{1-3}$alkyl, —OH, —$OCHF_2$, —$OCF_3$, —O—$C_{2-6}$alkyl$R^{10}$, —$OCH_3$, —$OCH_2CH_2NR^{12}R^{13}$, —$C_{1-6}$alkyl$R^{10}$, —$OC_6$heterocyclyl, —$OCH_2C_6$heterocyclyl, —$CH_2C_6$heterocyclyl, —$CH_2CH_2C_6$heterocyclyl, —$NHC(O)R^{11}$, —$SO_2R^{11}$ or —$SOR^{11}$.

In one embodiment $R^{10}$ is —H. In another embodiment $R^{10}$ is —$OR^{11}$. In a further embodiment $R^{10}$ is —$NR^{12}R^{13}$.

In one embodiment $R^{11}$ is —H or methyl. In another embodiment $R^{11}$ is —H. In a further embodiment $R^{11}$ is methyl.

In one embodiment $R^{12}$ and $R^{13}$ are each independently selected from —H and methyl.

In another embodiment $R^{12}$ and $R^{13}$ join together with the nitrogen atom to which they are attached, to form a $C_{4-7}$heterocyclyl selected from azetidinyl, pyrrolidinyl, piperidinyl, piperazinyl, morpholinyl and azepanyl optionally substituted by one or two substituents selected from —$C_{1-3}$alkyl, —OH and fluorine.

In one embodiment m is 2 or 3. In another embodiment m is 2. In a further embodiment m is 3.

In one embodiment n is 2 or 3. In another embodiment n is 2. In a further embodiment n is 3.

It is to be understood that the present invention covers all combinations of substituent groups described hereinabove.

Compounds of the invention include the compounds of Examples 1 to 58 and salts thereof.

In one embodiment there is provided the compounds of Examples 1 to 49 and salts thereof.

In one embodiment the compound of formula (I) is
1-benzyl-$N^5$-ethyl-$N^3$-methyl-2-oxo-1,2-dihydropyridine-3,5-dicarboxamide;
1-benzyl-$N^3$-methyl-2-oxo-$N^5$-propyl-1,2-dihydropyridine-3,5-dicarboxamide;
1-benzyl-$N^5$-butyl-$N^3$-methyl-2-oxo-1,2-dihydropyridine-3,5-dicarboxamide;
1-benzyl-$N^5$-isopentyl-$N^3$-methyl-2-oxo-1,2-dihydropyridine-3,5-dicarboxamide;
1-benzyl-$N^3$-methyl-$N^5$-(4-(methylamino)-4-oxobutyl)-2-oxo-1,2-dihydropyridine-3,5-dicarboxamide;
tert-butyl (3-(1-benzyl-5-(methylcarbamoyl)-6-oxo-1,6-dihydropyridine-3-carboxamido)propyl)carbamate;
1-benzyl-$N^3$-methyl-2-oxo-$N^5$-(3,3,3-trifluoropropyl)-1,2-dihydropyridine-3,5-dicarboxamide;
$N^5$-(2-(1H-imidazol-5-yl)ethyl)-1-benzyl-$N^3$-methyl-2-oxo-1,2-dihydropyridine-3,5-dicarboxamide;
methyl 4-(1-benzyl-5-(methylcarbamoyl)-6-oxo-1,6-dihydropyridine-3-carboxamide)butanoate;
1-benzyl-$N^3$-methyl-2-oxo-$N^5$-(2-(pyridin-2-yl)ethyl)-1,2-dihydropyridine-3,5-dicarboxamide;
$N^5$-(3-(1H-imidazol-2-yl)propyl)-1-benzyl-$N^3$-methyl-2-oxo-1,2-dihydropyridine-3,5-dicarboxamide;
$N^5$-(2-(1H-pyrazol-4-yl)ethyl)-1-benzyl-$N^3$-methyl-2-oxo-1,2-dihydropyridine-3,5-dicarboxamide;
$N^5$-(2-(1H-pyrazol-4-yl)ethyl)-$N^3$-methyl-1-(3-methylbenzyl)-2-oxo-1,2-dihydropyridine-3,5-dicarboxamide;
$N^5$-ethyl-$N^3$-methyl-1-(3-methylbenzyl)-2-oxo-1,2-dihydropyridine-3,5-dicarboxamide;
(R)—$N^5$-(2-(1H-pyrazol-4-yl)ethyl)-$N^3$-methyl-2-oxo-1-(1-phenylethyl)-1,2-dihydropyridine-3,5-dicarboxamide;
(R)—$N^5$-ethyl-$N^3$-methyl-2-oxo-1-(1-phenylethyl)-1,2-dihydropyridine-3,5-dicarboxamide;
$N^5$-(2-(1H-pyrazol-4-yl)ethyl)-1-(3-methoxybenzyl)-$N^3$-methyl-2-oxo-1,2-dihydropyridine-3,5-dicarboxamide;
$N^5$-ethyl-1-(3-methoxybenzyl)-$N^3$-methyl-2-oxo-1,2-dihydropyridine-3,5-dicarboxamide;
$N^5$-(2-(1H-imidazol-4-yl)ethyl)-1-(3-(2-hydroxyethoxy)benzyl)-$N^3$-methyl-2-oxo-1,2-dihydropyridine-3,5-dicarboxamide;
$N^5$-ethyl-1-(3-(2-hydroxyethoxy)benzyl)-$N^3$-methyl-2-oxo-1,2-dihydropyridine-3,5-dicarboxamide;
$N^5$-(2-(1H-pyrazol-4-yl)ethyl)-1-(3-(2-hydroxyethoxy)benzyl)-$N^3$-methyl-2-oxo-1,2-dihydropyridine-3,5-dicarboxamide;
$N^5$-ethyl-1-(2-fluoro-3-methylbenzyl)-$N^3$-methyl-2-oxo-1,2-dihydropyridine-3,5-dicarboxamide;
$N^5$-(2-(1H-pyrazol-4-yl)ethyl)-1-(2-fluoro-3-methylbenzyl)-$N^3$-methyl-2-oxo-1,2-dihydropyridine-3,5-dicarboxamide;
$N^5$-(2-(1H-imidazol-4-yl)ethyl)-1-((1H-indol-4-yl)methyl)-$N^3$-methyl-2-oxo-1,2-dihydropyridine-3,5-dicarboxamide;
1-((1H-indol-4-yl)methyl)-$N^5$-ethyl-$N^3$-methyl-2-oxo-1,2-dihydropyridine-3,5-dicarboxamide;
1-((1H-indol-4-yl)methyl)-$N^5$-(2-(1H-pyrazol-4-yl)ethyl)-$N^3$-methyl-2-oxo-1,2-dihydropyridine-3,5-dicarboxamide;
1-benzyl-$N^3$,$N^5$-dimethyl-2-oxo-1,2-dihydropyridine-3,5-dicarboxamide;
1-benzyl-$N^5$-isobutyl-$N^3$-methyl-2-oxo-1,2-dihydropyridine-3,5-dicarboxamide;
1-benzyl-$N^5$-(2-methoxypropyl)-$N^3$-methyl-2-oxo-1,2-dihydropyridine-3,5-dicarboxamide;
1-benzyl-$N^5$-isopropyl-$N^3$-methyl-2-oxo-1,2-dihydropyridine-3,5-dicarboxamide;
1-benzyl-$N^5$-(2-hydroxypropyl)-$N^3$-methyl-2-oxo-1,2-dihydropyridine-3,5-dicarboxamide;
1-benzyl-$N^5$-(3-hydroxypropyl)-$N^3$-methyl-2-oxo-1,2-dihydropyridine-3,5-dicarboxamide;
1-benzyl-$N^5$-(3-(dimethylamino)butyl)-$N^3$-methyl-2-oxo-1,2-dihydropyridine-3,5-dicarboxamide;
1-benzyl-$N^3$-methyl-2-oxo-$N^5$-(2-(pyridin-4-yl)ethyl)-1,2-dihydropyridine-3,5-dicarboxamide;

1-benzyl-N³-methyl-N⁵-(3-(methylamino)-3-oxopropyl)-2-oxo-1,2-dihydropyridine-3,5-dicarboxamide;
1-benzyl-N⁵-(3-cyanopropyl)-N³-methyl-2-oxo-1,2-dihydropyridine-3,5-dicarboxamide;
1-benzyl-N⁵-(2-cyanoethyl)-N³-methyl-2-oxo-1,2-dihydropyridine-3,5-dicarboxamide;
N⁵-(3-aminopropyl)-1-benzyl-N³-methyl-2-oxo-1,2-dihydropyridine-3,5-dicarboxamide;
1-benzyl-N⁵-(3-hydroxybutyl)-N³-methyl-2-oxo-1,2-dihydropyridine-3,5-dicarboxamide;
1-benzyl-N³-methyl-2-oxo-N⁵-(2-(pyridin-3-yl)ethyl)-1,2-dihydropyridine-3,5-dicarboxamide;
1-benzyl-N⁵-(2-methoxyethyl)-N³-methyl-2-oxo-1,2-dihydropyridine-3,5-dicarboxamide;
1-benzyl-N⁵-(3-methoxypropyl)-N³-methyl-2-oxo-1,2-dihydropyridine-3,5-dicarboxamide;
1-(3-cyanobenzyl)-N³,N⁵-dimethyl-2-oxo-1,2-dihydropyridine-3,5-dicarboxamide;
4-(1-benzyl-5-(methylcarbamoyl)-6-oxo-1,6-dihydropyridine-3-carboxamido)butanoic acid;
1-benzyl-N³-methyl-N⁵-(2-(methylsulfonyl)ethyl)-2-oxo-1,2-dihydropyridine-3,5-dicarboxamide;
1-benzyl-N⁵-(2-hydroxyethyl)-N³-methyl-2-oxo-1,2-dihydropyridine-3,5-dicarboxamide;
1-benzyl-N⁵-(3-(dimethylamino)propyl)-N³-methyl-2-oxo-1,2-dihydropyridine-3,5-dicarboxamide;
1-benzyl-N³-methyl-N⁵-(3-(methylsulfonyl)propyl)-2-oxo-1,2-dihydropyridine-3,5-dicarboxamide;
N⁵-(2-(1H-imidazol-4-yl)ethyl)-1-(2-fluoro-3-methylbenzyl)-N³-methyl-2-oxo-1,2-dihydropyridine-3,5-dicarboxamide;
N⁵-(2-(1H-pyrazol-5-yl)ethyl)-1-benzyl-N³-methyl-2-oxo-1,2-dihydropyridine-3,5-dicarboxamide;
1-benzyl-N³-methyl-N⁵-(1-methyl-1H-pyrazol-3-yl)-2-oxo-1,2-dihydropyridine-3,5-dicarboxamide;
1-benzyl-N³-methyl-N⁵-(2-(1-methyl-1H-pyrazol-4-yl)ethyl)-2-oxo-1,2-dihydropyridine-3,5-dicarboxamide;
1-benzyl-N³-methyl-N⁵-(1-methyl-1H-pyrazol-4-yl)-2-oxo-1,2-dihydropyridine-3,5-dicarboxamide;
1-benzyl-N³-methyl-N⁵-(2-(4-methyl-4H-1,2,4-triazol-3-yl)ethyl)-2-oxo-1,2-dihydropyridine-3,5-dicarboxamide;
1-benzyl-N³-methyl-N⁵-(2-(4-methylthiazol-5-yl)ethyl)-2-oxo-1,2-dihydropyridine-3,5-dicarboxamide;
1-benzyl-N³-methyl-2-oxo-N⁵-(2-(thiazol-4-yl)ethyl)-1,2-dihydropyridine-3,5-dicarboxamide;
1-benzyl-N⁵-(2-(isoxazol-4-yl)ethyl)-N³-methyl-2-oxo-1,2-dihydropyridine-3,5-dicarboxamide; and
1-benzyl-N³-methyl-2-oxo-N⁵-(pyridazin-4-yl)-1,2-dihydropyridine-3,5-dicarboxamide or a salt thereof.

In one embodiment the compound of formula (I) is 1-benzyl-N³-methyl-2-oxo-N⁵-propyl-1,2-dihydropyridine-3,5-dicarboxamide or a salt thereof. In another embodiment the compound of formula (I) is 1-benzyl-N³-methyl-2-oxo-N⁵-propyl-1,2-dihydropyridine-3,5-dicarboxamide or a pharmaceutically acceptable salt thereof. In another embodiment the compound of formula (I) is 1-benzyl-N³-methyl-2-oxo-N⁵-propyl-1,2-dihydropyridine-3,5-dicarboxamide. In a further embodiment the compound of formula (I) is a pharmaceutically acceptable salt of 1-benzyl-N3-methyl-2-oxo-N5-propyl-1,2-dihydropyridine-3,5-dicarboxamide.

In one embodiment the compound of formula (I) is

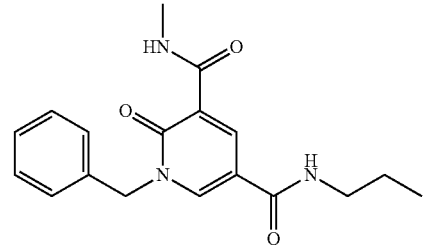 [SMILES: CCCNC(=O)c1cc(C(=O)NC)c(=O)n(Cc2ccccc2)c1]

or a salt thereof. In another embodiment the compound of formula (I) is

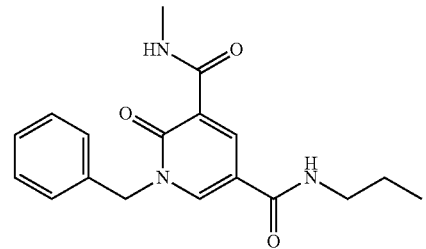 [SMILES: CCCNC(=O)c1cc(C(=O)NC)c(=O)n(Cc2ccccc2)c1]

or a pharmaceutically acceptable salt thereof. In another embodiment the compound of formula (I) is

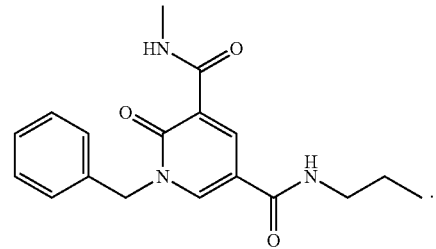 [SMILES: CCCNC(=O)c1cc(C(=O)NC)c(=O)n(Cc2ccccc2)c1]

In a further embodiment the compound of formula (I) is a pharmaceutically acceptable salt of

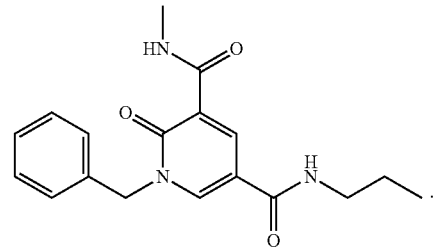 [SMILES: CCCNC(=O)c1cc(C(=O)NC)c(=O)n(Cc2ccccc2)c1]

In one embodiment the compound of formula (I) is N⁵-(2-(1H-pyrazol-4-yl)ethyl)-N³-methyl-1-(3-methylbenzyl)-2-oxo-1,2-dihydropyridine-3,5-dicarboxamide or a salt thereof. In another embodiment the compound of formula (I) is N⁵-(2-(1H-pyrazol-4-yl)ethyl)-N³-methyl-1-(3-methylbenzyl)-2-oxo-1,2-dihydropyridine-3,5-dicarboxamide or a pharmaceutically acceptable salt thereof. In another embodiment the compound of formula (I) is N⁵-(2-(1H-pyrazol-4-yl)ethyl)-N³-methyl-1-(3-methylbenzyl)-2-oxo-1,2-dihydropyridine-3,5-dicarboxamide. In a further embodiment the compound of formula (I) is a pharmaceutically acceptable salt of N⁵-(2-(1H-pyrazol-4-yl)ethyl)-N³-methyl-1-(3-methylbenzyl)-2-oxo-1,2-dihydropyridine-3,5-dicarboxamide.

In one embodiment the compound of formula (I) is

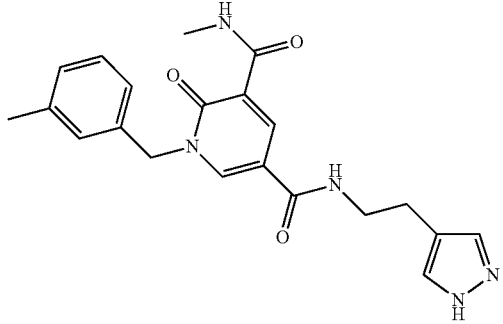 [SMILES: CNC(=O)c1cc(C(=O)NCCc2cn[nH]c2)cn(Cc2cccc(C)c2)c1=O]

or a salt thereof. In another embodiment the compound of formula (I) is

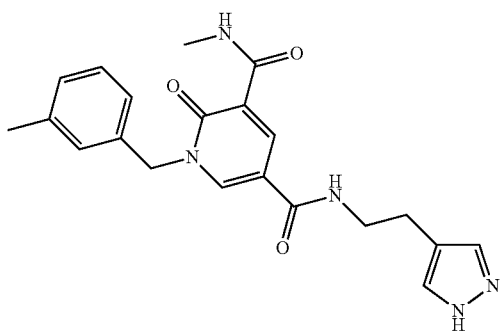 [SMILES: CNC(=O)c1cc(C(=O)NCCc2cn[nH]c2)cn(Cc2cccc(C)c2)c1=O]

or a pharmaceutically acceptable salt thereof. In another embodiment the compound of formula (I) is

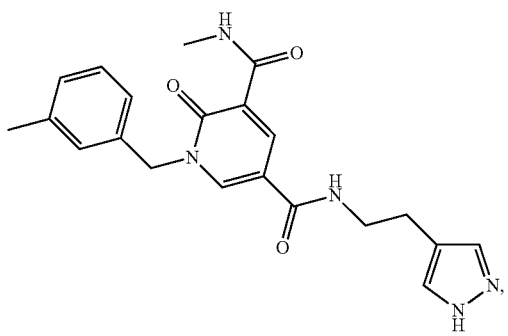 [SMILES: CNC(=O)c1cc(C(=O)NCCc2cn[nH]c2)cn(Cc2cccc(C)c2)c1=O]

In a further embodiment the compound of formula (I) is a pharmaceutically acceptable salt of

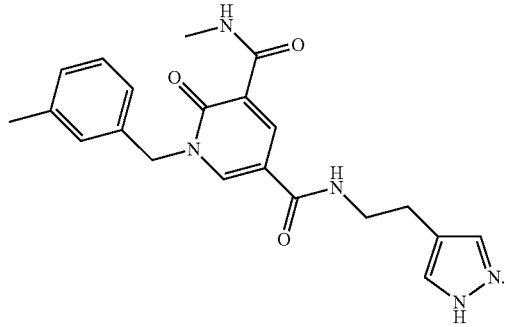 [SMILES: CNC(=O)c1cc(C(=O)NCCc2cn[nH]c2)cn(Cc2cccc(C)c2)c1=O]

In one embodiment the compound of formula (I) is N⁵-ethyl-1-(3-(2-hydroxyethoxy)benzyl)-N³-methyl-2-oxo-1,2-dihydropyridine-3,5-dicarboxamide or a salt thereof. In another embodiment the compound of formula (I) is N⁵-ethyl-1-(3-(2-hydroxyethoxy)benzyl)-N³-methyl-2-oxo-1,2-dihydropyridine-3,5-dicarboxamide or a pharmaceutically acceptable salt thereof. In another embodiment the compound of formula (I) is N⁵-ethyl-1-(3-(2-hydroxyethoxy)benzyl)-N³-methyl-2-oxo-1,2-dihydropyridine-3,5-dicarboxamide. In a further embodiment the compound of formula (I) is a pharmaceutically acceptable salt of N⁵-ethyl-1-(3-(2-hydroxyethoxy)benzyl)-N³-methyl-2-oxo-1,2-dihydropyridine-3,5-dicarboxamide.

In one embodiment the compound of formula (I) is

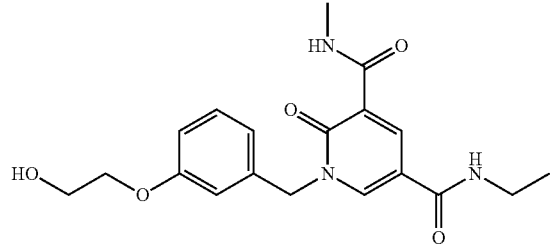 [SMILES: CCNC(=O)c1cc(C(=O)NC)c(=O)n(Cc2cccc(OCCO)c2)c1]

or a salt thereof. In another embodiment the compound of formula (I) is

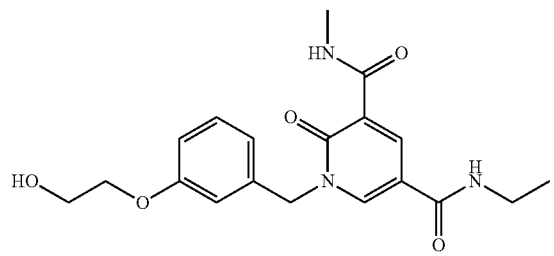 [SMILES: CCNC(=O)c1cc(C(=O)NC)c(=O)n(Cc2cccc(OCCO)c2)c1]

or a pharmaceutically acceptable salt thereof. In another embodiment the compound of formula (I) is

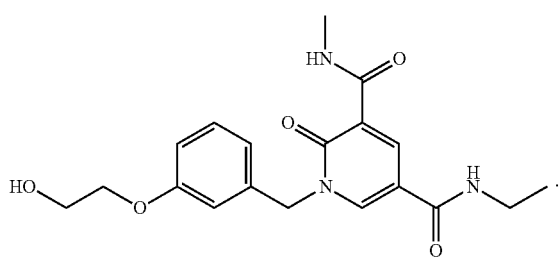 [SMILES: CCNC(=O)c1cc(C(=O)NC)c(=O)n(Cc2cccc(OCCO)c2)c1]

In a further embodiment the compound of formula (I) is a pharmaceutically acceptable salt of

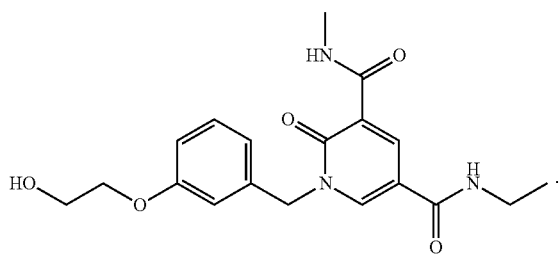

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, renal fibrosis, post-operative stricture, keloid scar formation, scleroderma (including morphea) or cardiac fibrosis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilrn's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colarectal cancer.

Bromodomain inhibitors may be useful in the treatment of diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain which comprises contacting the bromodomain with a compound of formula (I) or a pharmaceutically acceptable salt thereof.

As used herein the reference to the "treatment" of a particular disease or condition includes the prevention or prophylaxis of such a disease or condition.

Pharmaceutical Compositions/Routes of Administration/Dosages

Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. The pharmaceutical composition can be used in the treatment of any of the conditions described herein.

In a further aspect the invention is directed to pharmaceutical compositions for the treatment or prophylaxis of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The pharmaceutical compositions of the invention typically contain one compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subjectcompliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral dministration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other theraputically active agent. Preferably, combination therapies according to the present invention comprise the administration of at least one compound of formula (I) or a pharmaceutically acceptable salt thereof, and at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

General Synthetic Routes

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in any of the Schemes below:

Scheme 1:

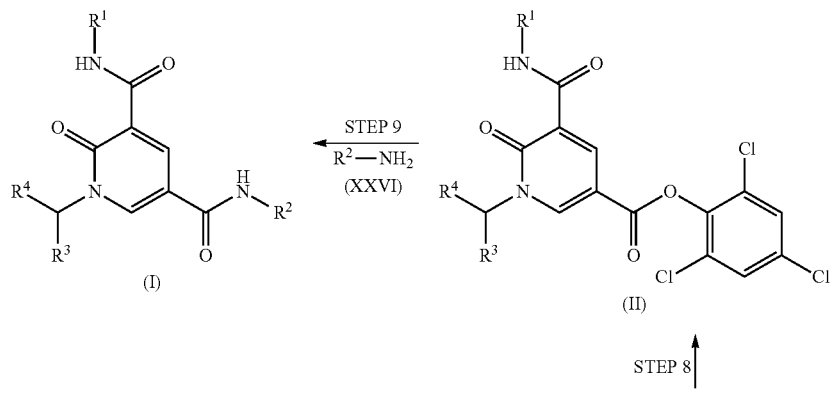

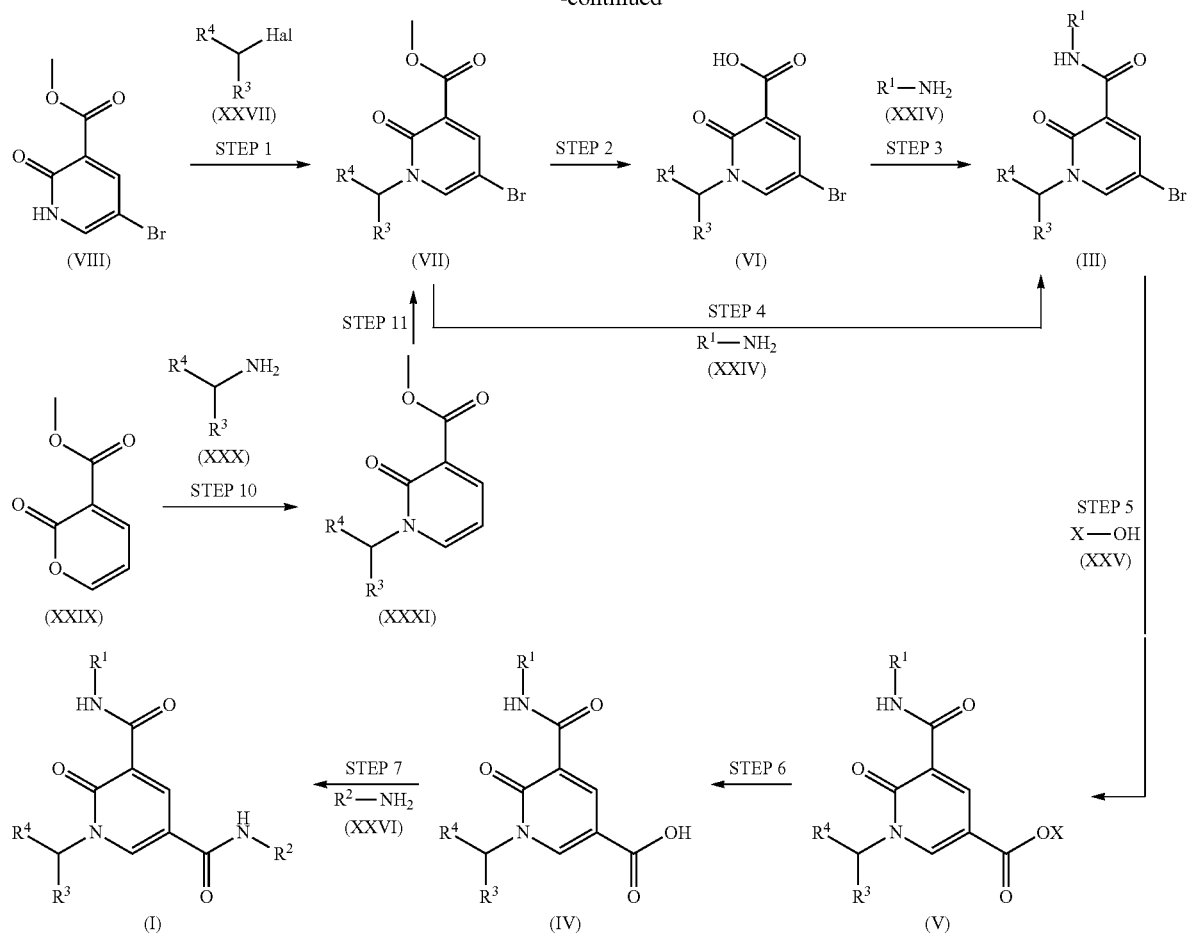

wherein $R^1$, $R^2$, $R^3$ and $R^4$ are as described above, Hal is chlorine or bromine and X is a $C_{1-6}$alkyl group.

In respect of the steps shown in Scheme 1 above the following reaction conditions may be utilised:

Step 1: is an alkylation and may be carried out using an alkyl or benzyl halide of formula $R^4CH(R^3)Hal$, such as an alkylbromide of formula $R^4CH(R^3)Br$, in the presence of an inorganic base, such as sodium hydride, in a suitable solvent, preferably an aprotic solvent, such as DMF, THF or 2-MeTHF, at a suitable temperature, such as 0° C.

Step 2: is base hydrolysis and may be carried out using any suitable inorganic base, such as LiOH, in a suitable solvent or solvent mixture, such as a mixture of methanol and THF, at a suitable temperature, such as room temperature.

Step 3: is an amide coupling reaction consisting of two steps. Step 3a, to produce the acid chloride, may be carried out using a chlorinating agent, such as oxalyl chloride, in the presence of a suitable catalyst, such as DMF, in a suitable solvent, such as DCM, at a suitable temperature, such as room temperature. Step 3b may be carried out using an amine reagent, $R^1$—$NH_2$, optionally in the presence of a tertiary amine, such as triethylamine, in a suitable solvent, such as THF, at a suitable temperature, such as 0° C.

Step 4: is an amine displacement reaction and may be carried out using an amine reagent, $R^1$—$NH_2$, in a suitable solvent or solvent mixture, such as a mixture of water and methanol, at a suitable temperature, such as 50° C.

Step 5: is a carbonylation reaction and may be carried out using an alcohol reagent, XOH (X is a $C_{1-6}$alkyl group), in the presence of a tertiary amine, such as triethylamine, in the presence of a palladium catalyst, such as palladium acetate, in the presence of a phosphine ligand, such as dppb, in the presence of carbon monoxide, in a suitable solvent, such as DMSO, at a suitable temperature, such as 100° C.

Step 6: is a hydrolysis step and may be carried out using an inorganic base, such as NaOH or LiOH, in a suitable solvent or solvent mixture, such as methanol and THF, at a suitable temperature, such as room temperature.

Step 7: is an amide coupling reaction and may be carried out using an amine reagent, $R^2$—$NH_2$, in the presence of a suitable tertiary amine, such as triethylamine or DIPEA, in the presence of a suitable amide coupling reactant, such as HATU, in a suitable solvent, such as DCM or DMF, at a suitable temperature, such as room temperature.

Step 8: is a carbonylation reaction and may be carried out using a metal carbonyl complex, such as dicobalt octacarbonyl, in the presence of a phosphine ligand, such as Xantphos, in the presence of a suitable palladium catalyst, such as palladium (II) acetate, in the presence of a nucleophilic catalyst, such as DMAP, in the presence of a suitable solvent, such as THF, at a suitable temperature, such as 80° C.

Step 9: is a displacement reaction and may be carried out using an amine reagent, $R^2$—$NH_2$, in the presence of a nucleophilic catalyst, such as DMAP, in the presence of a tertiary amine, such as triethylamine, in the presence of a suitable solvent, such as THF, at a suitable temperature, such as 45° C.

Step 10: is a pyridone formation and may be carried out using an alkyl or benzyl amine, such as $R^4CH(R^3)NH_2$, in a suitable solvent or solvent mixture, such as DMF and THF, with the addition of a suitable amide coupling reagent, such as EDC, a suitable nucleophilic catalyst, such as DMAP, and a suitable temperature, such as room temperature.

Step 11: is a bromination reaction and may be carried out using a suitable brominating reactant, such as NBS, in a suitable solvent, such as 2-MeTHF, at a suitable temperature, such as room temperature.

presence of a suitable catalyst, such as DMF, in a suitable solvent, such as DCM, at a suitable temperature, such as room temperature.

Step 2: is an amine displacement reaction, and may be carried out using an amine reagent, $R^1$—$NH_2$, in the presence of a tertiary amine, such as triethylamine, in a suitable solvent, such as THF, at a suitable temperature, such as 0° C.

Step 3: is a carbonylation reaction and may be carried out using an alcohol reagent, YOH (Y is a $C_{1-6}$alkyl group), in the presence of a tertiary amine, such as triethylamine, in the presence of a palladium catalyst, such as palladium (II) acetate, in the presence of a phosphine ligand, such as Scheme 2:

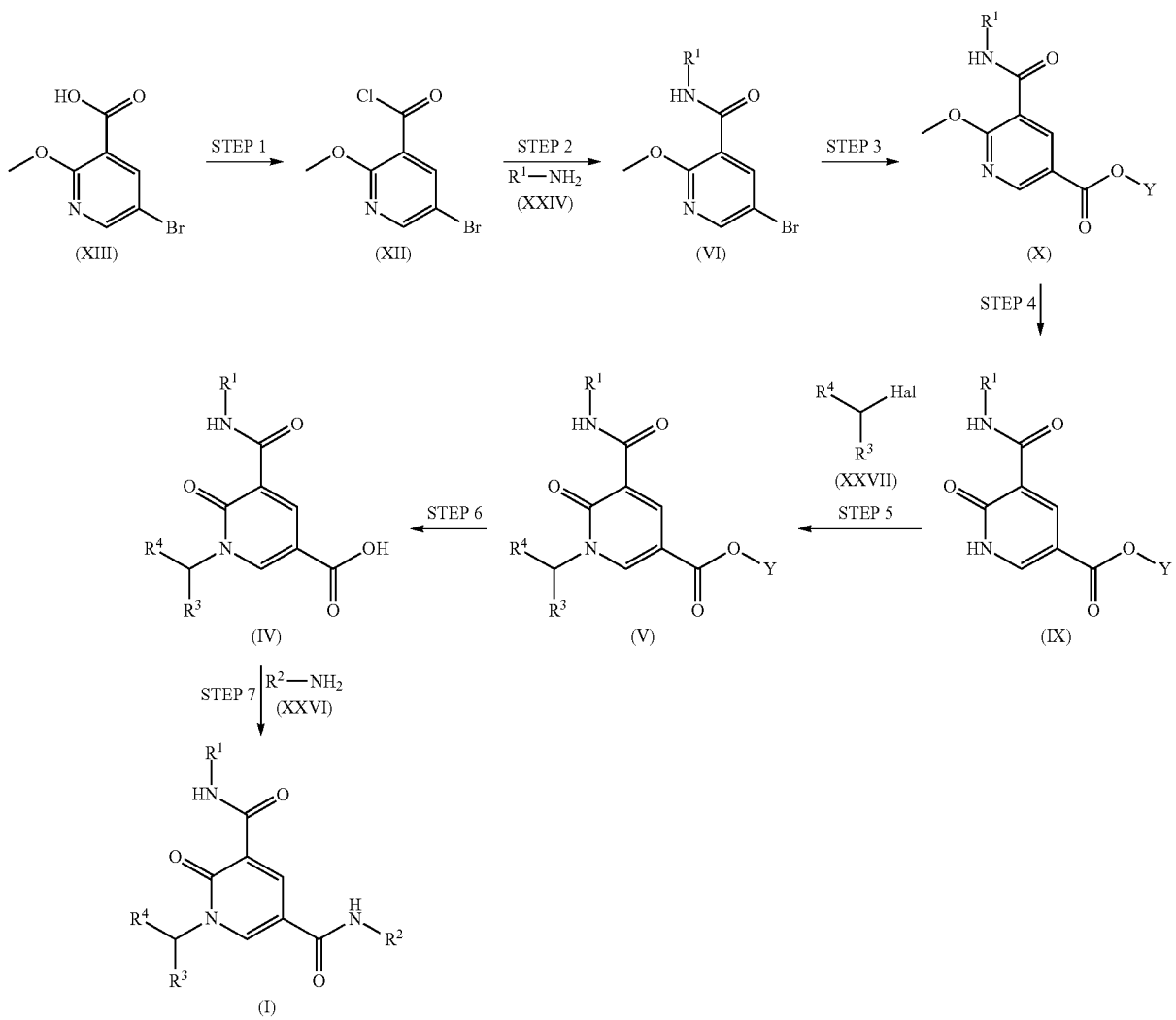

wherein $R^1$, $R^2$, $R^3$ and $R^4$ are as described above, Y is a $C_{1-6}$alkyl group and Hal is bromine or chlorine.

In respect of the steps shown in Scheme 2 above the following reaction conditions may be utilised:

Step 1: is an acid chloride formation, and may be carried out using a chlorinating agent, such as oxalyl chloride, in the dppb, in the presence of carbon monoxide, in a suitable solvent, such as DMSO, at a suitable temperature, such as 100° C.

Step 4: is a demethylation reaction and may be carried out using a demethylating agent, such as NaI with TMS-Cl, in a suitable solvent, such as acetonitrile, at a suitable temperature, such as room temperature.

Step 5: is an alkylation and may be carried out using an alkyl or benzyl halide such as a $R^4CH(R^3)Br$ or $R^4CH(R^3)Cl$, in the presence of an inorganic base, such as potassium carbonate, in a suitable solvent, such as DMF, at a suitable temperature, such as 90° C.

Step 6: is a hydrolysis step and may be carried out using an inorganic base, such as NaOH or LiOH, in a suitable solvent or solvent mixture, such as methanol and THF or 1,4-dioxane and water, at a suitable temperature, such as room temperature.

Step 7: is an amide coupling reaction and may be carried out using an amine reagent, $R^2$—$NH_2$, in the presence of a suitable tertiary amine, such as triethylamine or DIPEA, in the presence of an amide coupling reactant, such as HATU, in a suitable solvent, such as DCM or DMF, at a suitable temperature, such as room temperature.

Scheme 3:

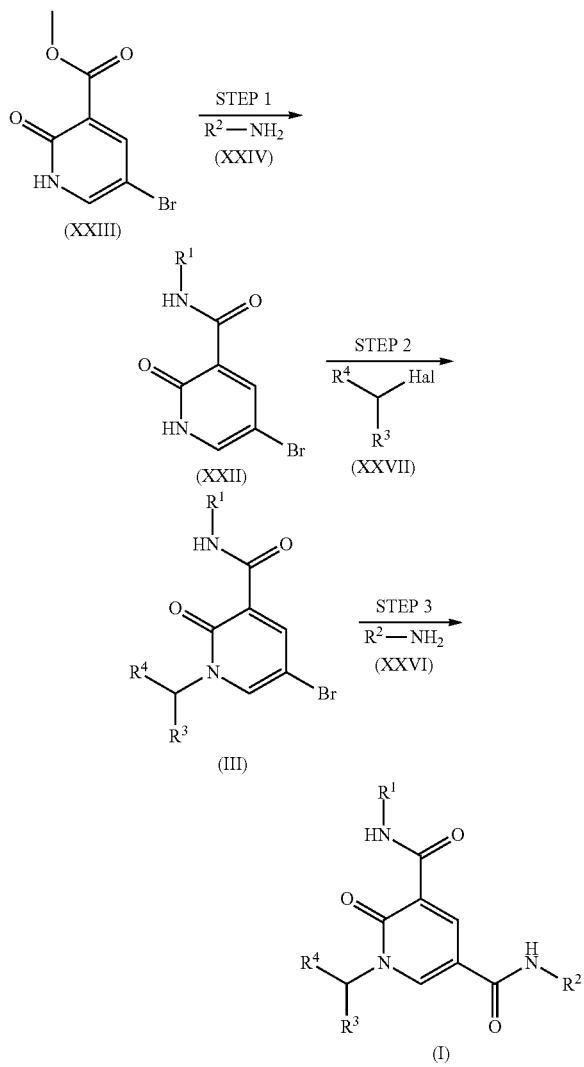

wherein $R^1$, $R^2$, $R^3$ and $R^4$ are as described above and Hal is chorine or bromine.

In respect of the steps shown in Scheme 3 above the following reaction conditions may be utilised:

Step 1: is an amine displacement reaction and may be carried out using an amine reagent, $R^1$—$NH_2$, in a suitable solvent, such as THF, at a suitable temperature, such as under reflux.

Step 2: is an alkylation and may be carried out using an alkyl or benzyl halide such as a $R^4CH(R^3)Br$ or $R^4CH(R^3)Cl$, in the presence of an inorganic base, such as potassium carbonate, in a suitable solvent, such as methanol or DMF, at a suitable temperature, such as 65° C. or 90° C.

Step 3: is an amino carbonylation reaction and may be carried out using an amine reagent such as $R^2$—$NH_2$, a metal carbonyl complex, such as dicobalt octacarbonyl, in the presence of a phosphine ligand, such as Xantphos or Catacxium A, in the presence of a suitable palladium catalyst, such as palladium (II) acetate, in the presence of a suitable nucleophilic catalyst, such as DMAP, in the presence of a suitable solvent, such as 1,4 dioxane or THF, at a suitable temperature, such as 80° C.

Compounds of Formulae (VIII), (XIII), (XX), (XXIII) and (XXIX) are commercially available from, for example, Sigma Aldrich, Fluorochem, Apollo Scientific or Combi-Blocks. Compounds of formulae $R^1$—$NH_2$, XOH, $R^2$—$NH_2$, $R^4CH(R^3)OH$, $R^3CH(R^3)NH_2$ and $R^4CH(R^3)Hal$ are either commercially available from the suppliers mentioned above or can by made by methods well known in the art or described herein.

Accordingly, in one embodiment there is provided a process for the preparation of a compound of formula (I) by the reaction of a compound of formula (II) with an amine of formula (XXVI)

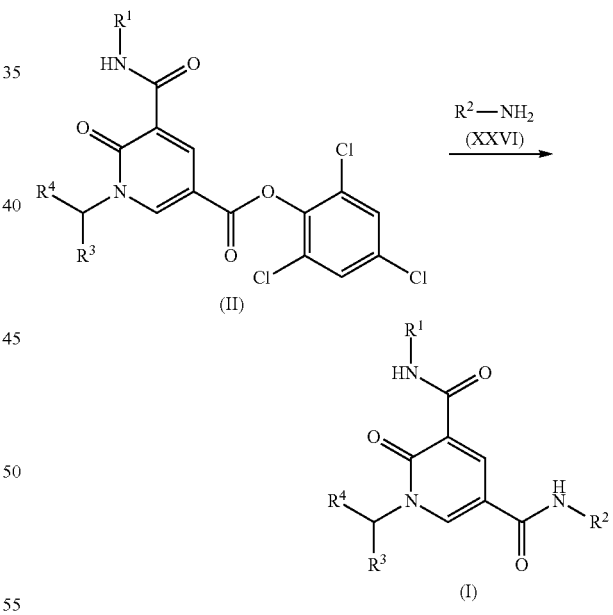

wherein $R^1$, $R^2$, $R^3$ and $R^4$ are as hereinbefore defined; in the presence of a nucleophilic catalyst, such as DMAP, in the presence of a tertiary amine, such as triethylamine, in the presence of a suitable solvent, such as THF, at a suitable temperature, such as 45° C. This step may be followed by removal of any protecting group, if required, followed by preparation of a salt, if required.

In a second embodiment there is provided a process for the preparation of a compound of formula (I) by the reaction of a compound of formula (III) with an amine of formula (XXVI)

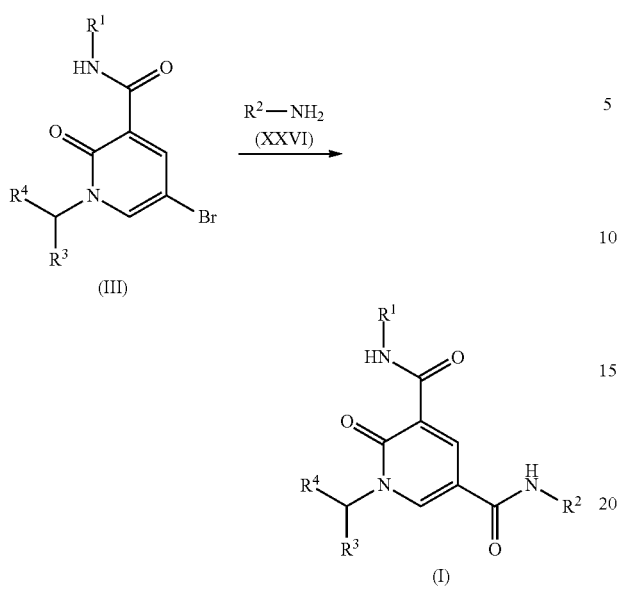

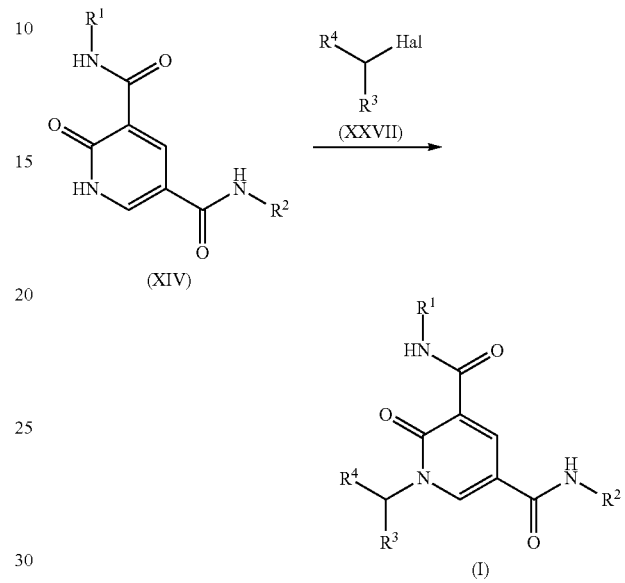

wherein $R^1$, $R^2$, $R^3$ and $R^4$ are as hereinbefore defined; in the presence of a metal carbonyl complex, such as dicobalt octacarbonyl, in the presence of a phosphine ligand, such as Xantphos or Catacxium A, in the presence of a suitable nucleophilic catalyst, such as DMAP, in the presence of a suitable solvent, such as 1,4 dioxane or THF, at a suitable temperature, such as 80° C. This step may be followed by removal of any protecting group, if required, followed by preparation of a salt, if required.

In a third embodiment there is provided a process for the preparation of a compound of formula (I) by the reaction of a compound of formula (IV) with an amine of formula (XXVI)

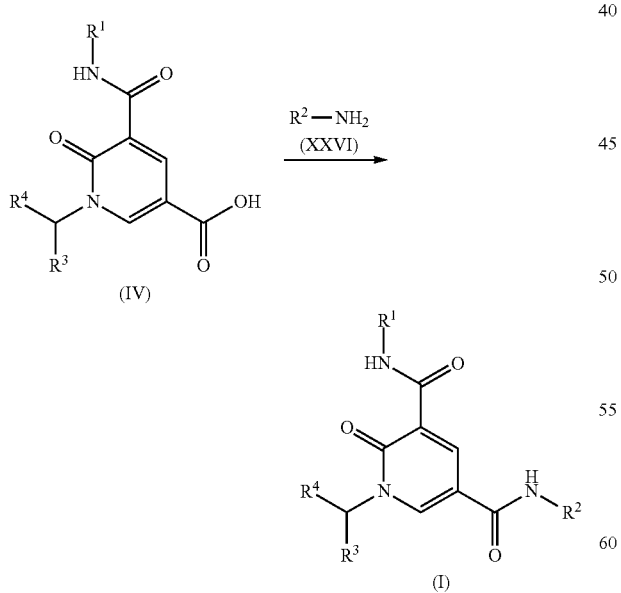

wherein $R^1$, $R^2$, $R^3$ and $R^4$ are as hereinbefore defined; in the presence of an amide coupling reagent, such as HATU, a tertiary amine, such as triethylamine or DIPEA, in the presence of a suitable solvent, such as DCM or DMF, at a suitable temperature, such as room temperature. This step may be followed by removal of any protecting group, if required, followed by preparation of a salt, if required.

In a fourth embodiment there is provided a process for the preparation of a compound of formula (I) by the reaction of a compound of formula (XIV) with a compound of formula (XXVII)

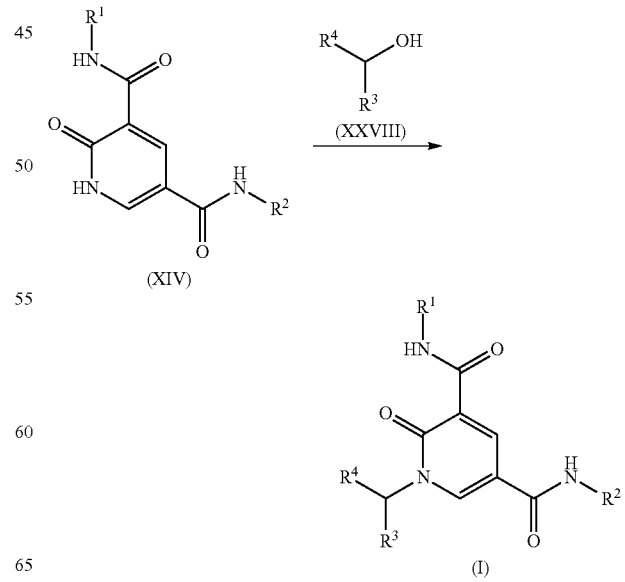

wherein $R^1$, $R^2$, $R^3$ and $R^4$ are as hereinbefore defined and Hal is chlorine or bromine; in the presence of an inorganic base, such as potassium carbonate, in a suitable solvent, such as DMF, at a suitable temperature, such as 90° C. This step may be followed by removal of any protecting group, if required, followed by preparation of a salt, if required.

In a fifth embodiment there is provided a process for the preparation of a compound of formula (I) by the reaction of a compound of formula (XIV) with a compound of formula (XXVIII)

$R^1$, $R^2$, $R^3$ and $R^4$ are as hereinbefore defined; in the presence of a Mitsunobu reagent, such as 2-(tributylphosphoranylidene)acetonitrile or DIAD in the presence of a phosphine, such as triphenyl phosphine, in a suitable solvent, such as toluene, at a suitable temperature, such as 120° C. or room temperature. This step may be followed by removal of any protecting group, if required, followed by preparation of a salt, if required.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006), incorporated herein by reference as it relates to such procedures.

Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by acid mediated cleavage (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—C(O)CF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LC-MS.

EXAMPLES

General Experimental details

All temperatures referred to are in ° C.

The names of the following compounds have been obtained using the compound naming programme "ACD Name Pro 6.02" or ChemDraw Ultra 12.0.

Abbreviations

AcOH acetic acid
BBr$_3$ boron tribromide
BOC/Boc tert-butyloxycarbonyl
BuLi butyllithium
Cs$_2$CO$_3$ cesium carbonate
CHCl$_3$ chloroform
Cobalt carbonyl dicobalt octacarbonyl
CV column volume
D6-DMSO deuterated dimethylsulfoxide
DCM dichloromethane
DIAD diisopropyl azodicarboxylate
DIPEA diisopropylethylamine
DMAP 4-dimethylaminopyridine
DMF dimethylformamide
DMSO dimethylsulfoxide
DPPA diphenylphosphoryl azide
EDC 1-ethyl-3-(3-dimethylaminopropyl)carbodiimide
Et$_3$N triethylamine
EtOAc ethyl acetate
h hour(s)
HATU O-(7-azabenzotriazol-1-yl)-N,N,N',N'-tetramethyluronium hexafluorophosphate
HCl hydrochloric acid
HCO$_2$H formic acid
IPA isopropyl alcohol
Isolera Biotage Flash purification system
K$_2$CO$_3$ potassium carbonate
KOH potassium hydroxide
LCMS liquid chromatography-mass spectrometry
LiOH lithium hydroxide
M molar (concentration)
MDAP mass directed autoprep
MeCN acetonitrile
MeI methyl iodide
MeOH methanol
min minute(s)
MTBE methyl tert-butyl ether
N normal (concentration)
N$_2$ nitrogen
Na$_2$CO$_3$ sodium carbonate
NaI sodium iodide
NaH sodium hydride
Na(OAc)$_3$BH sodium triacetoxy borohydride
Na$_2$SO$_4$ sodium sulphate
NBS N-bromosuccinimide
NEt$_3$ triethylamine
NMP N-methyl-2-pyrrolidone
Pd/C palladium on carbon
PPh$_3$ triphenylphosphine
RBF round bottomed flask
Rt retention time
rt room temperature
sat saturated
SCX Isolute strong cation exchange sorbent SPE
SNAP Biotage (silica) flash chromatography cartridge
SP4 Biotage Flash purification system
SPE solid phase extraction
TBME tert-butyl methyl ether
Tf$_2$O trifluoromethanesulfonic anhydride
TFA trifluoroacetic acid
THF tetra hydrofuran
TMSCl/TMS-Cl trimethylsilyl chloride
TLC Thin layer chromatography
UPLC ultra performance liquid chromatograpy
XantPhos 1,1'-(9,9-dimethyl-9H-xanthene-4,5-diyl)bis[1,1-diphenylphosphine
LCMS Methodology
Formic Method
LC Conditions The UPLC analysis was conducted on an Acquity UPLC CSH C18 column (50 mm×2.1 mm, i.d. 1.7 μm packing diameter) at 40° C.

The solvents employed were:

A=0.1% v/v solution of formic acid in water

B=0.1% v/v solution of formic acid in acetonitrile

The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions

MS: Waters ZQ

Ionisation mode: Alternate-scan positive and negative electrospray

Scan range: 100 to 1000 AMU

Scan time: 0.27 sec

Inter scan delay: 0.10 sec

High pH Method

LC Conditions

The UPLC analysis was conducted on an Acquity UPLC CSH C18 column (50 mm×2.1 mm, i.d. 1.7 μm packing diameter) at 40° C.

The solvents employed were:

A=10 mM ammonium hydrogen carbonate in water adjusted to pH10 with ammonia solution B=acetonitrile The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions

MS: Waters ZQ

Ionisation mode: Alternate-scan positive and negative electrospray

Scan range: 100 to 1000 AMU

Scan time: 0.27 sec

Inter scan delay: 0.10 sec

TFA Method

LC Conditions

The UPLC analysis was conducted on an Acquity UPLC CSH C18 column (50 mm×2.1 mm, i.d. 1.7 μm packing diameter) at 40° C.

The solvents employed were:

A=0.1% v/v solution of trifluoroacetic acid in water

B=0.1% v/v solution of trifluoroacetic acid in acetonitrile

The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.

MS Conditions

MS: Waters ZQ

Ionisation mode: Alternate-scan positive and negative electrospray

Scan range: 100 to 1000 AMU

Scan time: 0.27 sec

Inter scan delay: 0.10 sec

General MDAP Purification Methods

Listed below are examples of mass-directed autopreparative chromatography (MDAP) methods that have been used or may be used in compound purification.

MDAP (High pH). The HPLC analysis was conducted on an Xselect CSH C18 column (150 mm×30 mm i.d. 5 μm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (Formic). The HPLC analysis was conducted on an Xselect CSH C18 column (150 mm×30 mm i.d. 5 μm packing diameter) at ambient temperature, eluting with 0.1% formic acid in water (Solvent A) and 0.1% formic acid in acetonitrile (Solvent B) using an elution gradient of between 0 and 100% solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (TFA). The HPLC analysis was conducted on an Xselect CSH C18 column (150 mm×30 mm i.d. 5 μm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

NMR

Spectra were run on either a 400 MHz or 600 MHz NMR machine at either 302 K or for VT spectra at 392-393 K.

Intermediate 1: 2,4,6-Trichlorophenyl Formate

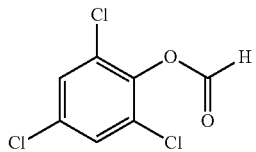 [SMILES: O=COc1c(Cl)cc(Cl)cc1Cl]

Formic acid (57.3 mL, 1519 mmol) and acetic anhydride (115 mL, 1216 mmol) were stirred and heated to 60° C. for 1.5 h then allowed to cool to ambient temperature. The resulting solution was poured into a flask containing 2,4,6-trichlorophenol (30 g, 152 mmol, commercially available from, for example, Sigma-Aldrich) and sodium acetate (12.46 g, 152 mmol). The mixture was stirred for 3.5 h, diluted with toluene (300 mL), washed with water (2×200 mL), dried with sodium sulphate, filtered and evaporated to dryness in vacuo to afford white needle-like crystals (32.45 g).

LCMS (2 min Formic): Rt=1.15 min, [M+Na]$^+$=249.8.

Intermediate 2: Methyl 1-tosyl-1H-indole-4-carboxylate

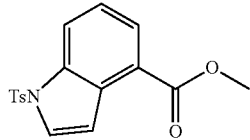 [SMILES: COC(=O)c1cccc2c1ccn2S(=O)(=O)c1ccc(C)cc1]

Methyl 1H-indole-4-carboxylate (750 mg, 4.28 mmol, commercially available from, for example, Sigma-Aldrich) was dissolved in DMF (13.591 mL) at 0° C. under nitrogen. Sodium hydride (205 mg, 5.14 mmol, 60% dispersion in mineral oil) was added in portions. The reaction was stirred at 0° C. for 10 min before warming to rt and stirring for 30 min. Tosyl-Cl (979 mg, 5.14 mmol) was added and the reaction mixture was stirred at rt for 10 min. The reaction was cooled to 0° C. and quenched by the dropwise addition of water (3.86 mL, 214 mmol), before pouring onto saturated aqueous lithium chloride (140 mL). The product was extracted with ethyl acetate (3×30 mL) and the combined organic portions were dried through a hydrophobic frit and evaporated in vacuo to yield the crude product (2056 mg). The residue was dry loaded onto a 50 g SNAP silica cartridge and purified via Biotage SP4 flash chromaotography, eluting from 0-25% ethyl acetate/cyclohexane. The relevant fractions were combined and evaporated in vacuo to yield the pure product—methyl 1-tosyl-1H-indole-4-carboxylate (1039 mg, 3.15 mmol, 73.7% yield) as a white solid.

LCMS (2 min Formic): Rt=1.29 min, [ME]$^+$=330.0.

Intermediate 3: (1-Tosyl-1H-indol-4-yl)methanol

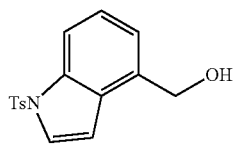 [SMILES: Cc1ccc(S(=O)(=O)n2ccc3c(CO)cccc32)cc1]

A solution of methyl 1-tosyl-1H-indole-4-carboxylate (1016 mg, 3.08 mmol) in DCM (30.361 mL) was cooled to −78° C. and DIBAL-H (1M in toluene, 13.57 mL, 13.57 mmol) was added dropwise over 1 h. The reaction mixture was stirred for a further 1.5 h, followed by a further 40 min. The reaction was quenched with methanol (0.125 mL, 3.08 mmol) when still at −78° C. and then allowed to warm to ambient temperature. The reaction was diluted with saturated Rochelle's salt solution (60 mL) and stirred for 16 h. The layers were separated, and the aqueous phase was extracted with dichloromethane (2×50 mL). The combined organic layers were dried through a hydrophobic frit and evaporated in vacuo to yield the crude product (913 mg). The residue was loaded in dichloromethane onto a 50 g SNAP cartridge and purified via Biotage SP4, eluting from 15-75% ethyl acetate/cyclohexane. The relevant fractions were combined and evaporated in vacuo to yield the pure product—(1-tosyl-1H-indol-4-yl)methanol (901 mg, 2.84 mmol, 92% yield) as a white solid.

LCMS (2 min Formic): Rt=1.07 min, [M+Na]$^+$=324.0.

Intermediate 4: 4-(Bromomethyl)-1-tosyl-1H-indole

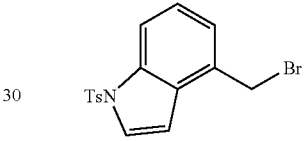

(1-Tosyl-1H-indol-4-yl)methanol (500 mg, 1.659 mmol) and HBr (3995 μL, 48% in water, 33.2 mmol) were heated at 80° C. monitoring by LCMS. Initial LCMS indicated formation of product and the reaction was heated for a further 4 h. The reaction mixture was poured onto water (10 mL) and the product was extracted with dichloromethane (3×20 mL). The combined organic portions were dried through a hydrophobic frit and evaporated in vacuo to yield the crude product—4-(bromomethyl)-1-tosyl-1H-indole (564 mg, 1.316 mmol, 79% yield) as a purple solid which was used without further purification.

LCMS (2 min Formic): Rt=1.35 min, [M−H]$^-$=362.0, 364.0.

Intermediate 5: 5-Bromo-2-methoxynicotinoyl chloride

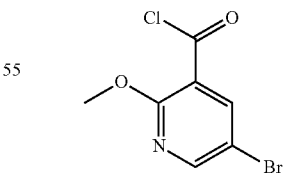

5-Bromo-2-methoxynicotinic acid (15 g, 64.6 mmol, commercially available from, for example Apollo Scientific) was suspended in DCM (100 mL) and then oxalyl chloride (16.98 mL, 194 mmol) was added, followed by DMF (5.01 mL, 64.6 mmol) and the mixture was stirred for 18 h at rt. The solvent was evaporated in vacuo and the residue was redissolved in DCM (100 mL) and evaporated to dryness to give 5-bromo-2-methoxynicotinoyl chloride (16.33 g, 65.2 mmol, 101% yield) which was used in the next step immediately.

¹H NMR (400 MHz, CDCl₃) δ ppm 8.49 (d, J=2.7 Hz, 1H) 8.44 (d, J=2.4 Hz, 1H) 4.06 (s, 3H).

Intermediate 6:
5-Bromo-2-methoxy-N-methylnicotinamide

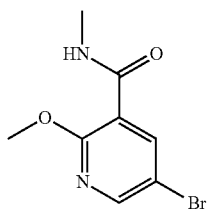

5-Bromo-2-methoxynicotinoyl chloride (16 g, 63.9 mmol) was dissolved in 2-methyltetrahydrofuran (100 mL) and Et₃N (8.90 mL, 63.9 mmol) was added, followed by methanamine (31.9 mL, 2M in THF, 63.9 mmol) and the mixture was stirred for 3 h at rt, then added to water (200 mL) and extracted with EtOAc (200 mL). The organic layer was washed with brine (200 mL), dried and evaporated in vacuo to give 5-bromo-2-methoxy-N-methylnicotinamide (14.8 g, 60.4 mmol, 95% yield) as a pale yellow solid.

LCMS (2 min High pH): Rt=0.83 min, [MH]⁺=245.1, 247.1.

Intermediate 7: Methyl
6-methoxy-5-(methylcarbamoyl)nicotinate

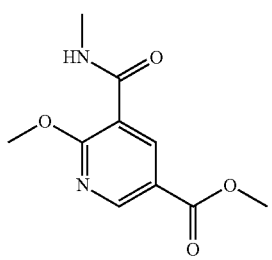

Carbon monoxide was gently bubbled through a mixture of 5-bromo-2-methoxy-N-methylnicotinamide (10.6 g, 43.3 mmol), xantphos (1.502 g, 2.60 mmol), triethylamine (12.06 mL, 87 mmol), palladium(II) acetate (0.486 g, 2.163 mmol) and methanol (17.50 mL, 433 mmol) in DMF (150 mL) until a yellow/green suspension resulted. The suspension was held under a balloon of carbon monoxide and heated to 60° C. for 5 h. LCMS showed significant SM, so the reaction was left overnight (16 h). The reaction mixture was then allowed to cool to rt. The solution was diluted with water (300 mL) and extracted with EtOAc (3×300 mL), and the combined organics back extracted with brine (3×100 mL). The combined organics were then dried (Na₂SO₄) and evaporated in vacuo to a brown solid. The residue was dissolved in DCM, loaded on to a 340 g Biotage silica SNAP column and eluted with 20→80% EtOAc/cyclohexane. The product containing fractions were evaporated in vacuo to a yellow solid—methyl 6-methoxy-5-(methylcarbamoyl)nicotinate (4 g, 17.84 mmol, 41.2% yield)

As the yield was lower than expected, the retained aqueous layer was analysed by LCMS and found to contain further product. This was therefore further extracted with DCM (3×100 mL), the combined organics were dried (Na₂SO₄) and concentrated in vacuo (for a prolonged period to remove DMF). The aqueous layer was re-analysed by LCMS and found to no longer contain product. The crude product from the organic phase, a yellow solid was taken up in DCM and added to a SNAP silica cartridge (100 g) and eluted with 20→80% EtOAc/cyclohexane The product containing fractions were evaporated in vacuo to a yellow solid—methyl 6-methoxy-5-(methylcarbamoyl)nicotinate (1.9 g, 8.47 mmol, 19.59% yield)

LCMS (2 min Formic): Rt=0.67 min, [MH]+=225.1.
1H NMR (400 MHz, DMSO-d6) δ ppm 8.82 (d, J=2.2 Hz, 1H) 8.55 (d, J=2.4 Hz, 1H) 8.30 (br. d, J=3.9 Hz, 1H) 4.05 (s, 3H) 3.87 (s, 3H) 2.82 (d, J=4.6 Hz, 3H).

Intermediate 8: Butyl
6-methoxy-5-(methylcarbamoyl)nicotinate

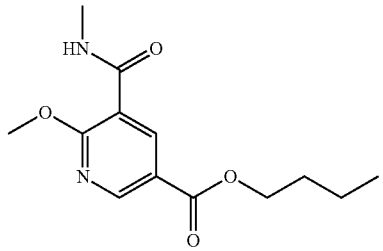 [SMILES: CCCCOC(=O)c1cnc(OC)c(C(=O)NC)c1]

(9,9-Dimethyl-9H-xanthene-4,5-diyl)bis(diphenylphosphine) (2.479 g, 4.28 mmol), triethylamine (18.58 g, 184 mmol), diacetoxypalladium (0.962 g, 4.28 mmol) and 5-bromo-2-methoxy-N-methylnicotinamide (15 g, 61.2 mmol) were combined in a 500 mL RBF, then DMF (100 mL) and 1-butanol (28.0 mL, 306 mmol) were added and the mixture was purged with carbon monoxide for 10 min, then a balloon containing around 1.5 liter of CO was added and the mixture was heated overnight at 90° C. The mixture was then cooled, diluted with water (500 mL) and extracted with EtOAc (2×500 mL). The organics were washed with water (200 mL), dried and evaporated in vacuo and the resulting black oil was purified by chromatography on a 340 g silica column eluting with 0-100% EtOAc/cyclohexane to give butyl 6-methoxy-5-(methylcarbamoyl)nicotinate (11 g, 41.3 mmol, 67.5% yield) as a pale yellow crystalline solid.

LCMS (2 min High pH): Rt=1.04 min, [MH]⁺=267.2.

Intermediate 9: Methyl 5-(methylcarbamoyl)-6-oxo-1,6-dihydropyridine-3-carboxylate

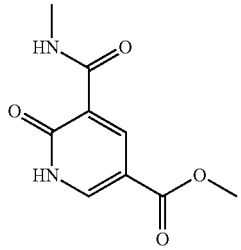

Sodium iodide (4.88 g, 32.6 mmol) was added to a solution of methyl 6-methoxy-5-(methylcarbamoyl)nicotinate (3.65 g, 16.28 mmol) in acetonitrile (100 mL) and this solution was stirred for 10 min under nitrogen. TMS-Cl (10.40 mL, 81 mmol) was added dropwise, and the reaction mixture was stirred at rt for 1 h. The reaction was quenched with water (100 mL) and the mixture was extracted five times with a mix of DCM/MeOH and the combined organic phase was dried over a hydrophobic frit and evaporated under vacuum. The crude material was dissolved in DCM and loaded onto a 100 g SNAP silica cartridge and eluted with 0-100% ethanol in EtOAc. The appropriate fractions were evaporated under vaccuum, and the desired product was obtained—methyl 5-(methylcarbamoyl)-6-oxo-1,6-dihydropyridine-3-carboxylate (1.5 g, 7.14 mmol, 43.8% yield).

LCMS (2 min Formic): Rt=0.47 min, [MH]+=211.1.

1H NMR (400 MHz, DMSO-d6) δ ppm 10.25 (br. s, 1H) 9.55 (br. d, J=4.4 Hz, 1H) 8.63 (d, J=2.7 Hz, 1H) 8.32 (d, J=2.7 Hz, 1H) 3.80 (s, 3H) 2.82 (d, J=4.9 Hz, 3H).

Intermediate 10: Butyl 5-(methylcarbamoyl)-6-oxo-1,6-dihydropyridine-3-carboxylate

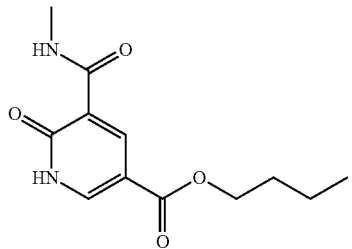 [SMILES: CCCCOC(=O)c1c[nH]c(=O)c(C(=O)NC)c1]

TMSCl (15.84 mL, 124 mmol) and sodium iodide (18.58 g, 124 mmol) were added to a solution of butyl 6-methoxy-5-(methylcarbamoyl)nicotinate (11 g, 41.3 mmol) in acetonitrile (200 mL) at rt, and the mixture was stirred for 1 h, then evaporated in vacuo and the residue partitioned between EtOAc (200 mL) and saturated sodium thiosulphate solution (200 mL). The organic layer was washed with brine, dried and evaporated in vacuo to give butyl 5-(methylcarbamoyl)-6-oxo-1,6-dihydropyridine-3-carboxylate (6.5 g, 25.8 mmol, 62.4% yield) as a pale yellow solid.

LCMS (2 min High pH): Rt=0.66 min, [MH]+=253.2.

Intermediate 11: (R)-Methyl 2-oxo-1-(1-phenylethyl)-1,2-dihydropyridine-3-carboxylate

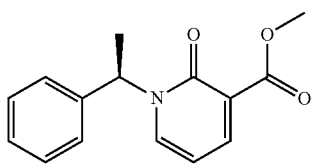 [SMILES: COC(=O)c1cccn([C@H](C)c2ccccc2)c1=O]

(R)-1-Phenylethanamine (8.93 mL, 70.2 mmol) was added to a stirred solution of methyl 2-oxo-2H-pyran-3-carboxylate (10.3 g, 66.8 mmol, commercially available from, for example, Sigma-Aldrich) in a mixture of dry DMF (43 mL) and dry THF (173 mL). The resulting dark red solution was stirred for 30 min, under N₂. EDC (16.66 g, 87 mmol) and DMAP (0.506 g, 4.14 mmol) were added and the resulting suspension stirred over the weekend. The reaction mixture was evaporated in vacuo to a brown slurry. The residue was partitioned between EtOAc and water and the aqueous layer removed. The organic layer was washed (3×2 M aq. HCl, 1× brine), dried over MgSO₄ and filtered through silica eluting with EtOAc. The filtrate was evaporated in vacuo to give the product as a brown oil (12.94 g).

LCMS (2 min TFA): Rt=0.84 min, [MH]+=258.1

Intermediate 12: (R)-Methyl 5-bromo-2-oxo-1-(1-phenylethyl)-1,2-dihydropyridine-3-carboxylate

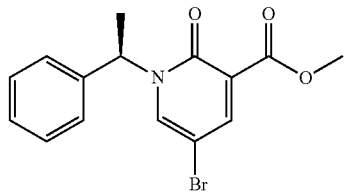 [SMILES: COC(=O)c1cc(Br)cn([C@H](C)c2ccccc2)c1=O]

NBS (10.74 g, 60.4 mmol) was added in one portion to a dark brown solution of (R)-methyl 2-oxo-1-(1-phenylethyl)-1,2-dihydropyridine-3-carboxylate (12.94 g, 50.3 mmol). The initial suspension became a light brown solution and was stirred for 15 min whereupon it was a dark brown solution. The reaction mixture was washed [3× sat. aq. NaHCO₃ (40 mL), 1× aq. 10% sodium thiosulfate (20 mL), 1× brine (10 mL)], dried over MgSO₄ and evaporated in vacuo to a black oil. The residue was dissolved in toluene (40 mL), filtered through celite, washing with toluene (80 mL) and evaporated in vacuo to give the product (19.62 g) as a black oil.

LCMS (2 min TFA): Rt=1.02 min, [MH]+=336.0 & 337.9.

Intermediate 13: Methyl 1-benzyl-5-bromo-2-oxo-1,2-dihydropyridine-3-carboxylate

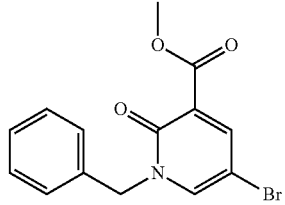 [SMILES: COC(=O)c1cc(Br)cn(Cc2ccccc2)c1=O]

Sodium hydride (5.17 g, 60% dispersion in mineral oil, 129 mmol) was added to a solution of methyl 5-bromo-2-oxo-1,2-dihydro-3-pyridinecarboxylate (25 g, 108 mmol, commercially available from, for example, Fluorochem) in DMF (200 mL) and THF (200 mL) at 0° C. and the mixture was stirred for 30 min, giving a dense suspension. Benzyl bromide (14.10 mL, 119 mmol) was added and the mixture stirred for a further 2 h, allowing to warm to rt, then the resulting clear brown solution was added to water (400 mL) and extracted with EtOAc (2×300 mL). The combined organics were washed with water (2×200 mL), dried and evaporated in vacuo to give methyl 1-benzyl-5-bromo-2-oxo-1,2-dihydropyridine-3-carboxylate (31 g, 96 mmol, 89% yield) as a beige solid. This material was carried through to the next step without purification.

LCMS (2 min High pH): Rt=0.98 min, [MH]⁺=322.0 & 324.1.

1H NMR (400 MHz, CHCl₃-d) δ ppm 8.16 (d, J=2.9 Hz, 1H) 7.62 (d, J=2.9 Hz, 1H) 7.30-7.43 (m, 5H) 5.15 (s, 2H) 3.92 (s, 3H).

Intermediate 14: 1-Benzyl-5-bromo-2-oxo-1,2-dihydropyridine-3-carboxylic acid

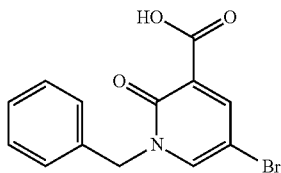 [SMILES: O=C(O)c1cc(Br)cn(Cc2ccccc2)c1=O]

Lithium hydroxide (6.91 g, 289 mmol) in water (200 mL) was added to a mixture of methyl 1-benzyl-5-bromo-2-oxo-1,2-dihydropyridine-3-carboxylate (31 g, 96 mmol), THF (200 mL) and methanol (200 mL) and the mixture was stirred at rt for 2 h, then evaporated in vacuo to about half volume, giving a dense suspension. This was diluted with water (200 mL) and acidified with acetic acid to pH 5, then extracted with EtOAc (2×300 mL). The combined organics were dried over sodium sulphate and evaporated in vacuo to give an off-white solid. The product was suspended in ether (200 mL), sonicated, diluted with cyclohexane (100 mL) and collected by filtration to give 1-benzyl-5-bromo-2-oxo-1,2-dihydropyridine-3-carboxylic acid (23 g, 74.6 mmol, 78% yield).

LCMS (2 min Formic): Rt=1.01 min, [MH]⁺=308.0 & 310.1.

1H NMR (400 MHz, CHCl₃-d) d ppm 14.02 (br. s., 1H) 8.55 (d, J=2.7 Hz, 1H) 7.73 (d, J=2.7 Hz, 1H) 7.40-7.47 (m, 3H) 7.31-7.37 (m, 2H) 5.25 (s, 2H).

Intermediate 15: 1-Benzyl-5-bromo-N-methyl-2-oxo-1,2-dihydropyridine-3-carboxamide

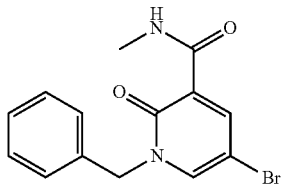 [SMILES: CNC(=O)c1cc(Br)cn(Cc2ccccc2)c1=O]

1-Benzyl-5-bromo-2-oxo-1,2-dihydropyridine-3-carboxylic acid (28 g, 91 mmol) was suspended in DCM (300 mL) and oxalyl chloride (23.86 mL, 273 mmol) and DMF (0.352 mL, 4.54 mmol) were added, then the mixture was stirred for 2 h at rt. The solvent was evaporated in vacuo to give a brown residue, which was then dissolved in THF (300 mL) and Et₃N (12.67 mL, 91 mmol) was added. The mixture was cooled in an ice bath, then methanamine (91 mL, 2M in THF, 182 mmol) was added dropwise over 30 min and the mixture stirred for a further 1 h at 0° C. The solvent was evaporated in vacuo and the solid residue was partitioned between water (300 mL) and DCM (300 mL), the organic layer was washed with brine, dried and evaporated in vacuo to give 1-benzyl-5-bromo-N-methyl-2-oxo-1,2-dihydropyridine-3-carboxamide (27.6 g, 86 mmol, 95% yield) as a brown solid.

LCMS (2 min Formic): Rt=0.97 min, [MH]⁺=321.0 & 323.1.

1H NMR (400 MHz, CHCl₃-d) δ ppm 9.57 (br. s., 1H) 8.60 (d, J=2.9 Hz, 1H) 7.62 (d, J=2.9 Hz, 1H) 7.34-7.48 (m, 3H) 7.29-7.33 (m, 2H) 5.20 (s, 2H) 3.00 (d, J=4.9 Hz, 3H).

Intermediate 16: (R)-5-Bromo-N-methyl-2-oxo-1-(1-phenylethyl)-1,2-dihydropyridine-3-carboxamide

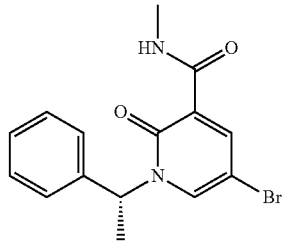 [SMILES: CNC(=O)c1cc(Br)cn([C@H](C)c2ccccc2)c1=O]

Methylamine solution (74 mL, 40% aq., 855 mmol) was added to a solution of (R)-methyl 5-bromo-2-oxo-1-(1-phenylethyl)-1,2-dihydropyridine-3-carboxylate (19.2 g, 40.0 mmol) in methanol (133 mL). The resulting solution was heated to 50° C. with a balloon fitted to the top of a condensor. The reaction mixture was stirred for 90 min. The reaction mixture was evaporated in vacuo to a black gum that was suspended in EtOAc. The suspension was filtered through silica eluting with EtOAc and the filtrate evaporated to give the product (13.1 g) as a brown gum.

LCMS (2 min TFA): Rt=1.01 min, [MH]⁺=335.1 & 337.1.

Intermediate 17: 2,4,6-Trichlorophenyl 1-benzyl-5-(methylcarbamoyl)-6-oxo-1,6-dihydropyridine-3-carboxylate

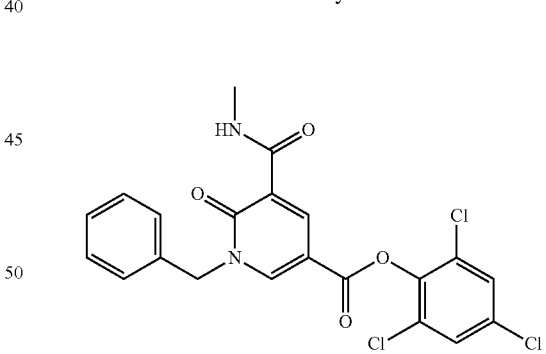

1-Benzyl-5-bromo-N-methyl-2-oxo-1,2-dihydropyridine-3-carboxamide (2 g, 6.23 mmol), Xantphos (0.360 g, 0.623 mmol), palladium acetate (0.070 g, 0.311 mmol) and Et₃N (1.302 mL, 9.34 mmol) were combined in a three necked flask equipped with a dropping funnel and a condensor with a nitrogen bubbler on the top. Toluene (30 mL) was added and the mixture was heated at 80° C. under nitrogen for 20 min, then a solution of 2,4,6-trichlorophenyl formate (2.106 g, 9.34 mmol) in toluene (20 mL) was added dropwise over 30 min and heating continued for 2 h. The reaction mixture was diluted with EtOAc (50 mL) and washed with water (50 mL) and brine (50 mL), dried and evaporated in vacuo to give an orange oil. This was dissolved in DCM (10 mL) and loaded onto a 50 g silica column, then eluted with 0-50% EtOAc/cyclohexane and the product-containing fractions evaporated in vacuo to give 2,4,6-trichlorophenyl 1-benzyl-5-(methylcarbamoyl)-6-oxo-1,6-dihydropyridine-3-carboxylate (2.52 g, 5.41 mmol, 87% yield) as a beige solid LCMS (2 min Formic): Rt=1.36 min, [MH]$^+$=465, 467.

Intermediate 18: Ethyl 1-benzyl-5-(methylcarbamoyl)-6-oxo-1,6-dihydropyridine-3-carboxylate

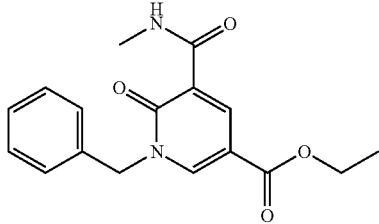 [SMILES: CCOC(=O)c1cc(C(=O)NC)c(=O)n(Cc2ccccc2)c1]

1-Benzyl-5-bromo-N-methyl-2-oxo-1,2-dihydropyridine-3-carboxamide (23 g, 71.6 mmol), DMSO (60 mL), ethanol (70 g, 1519 mmol), Et$_3$N (19.96 mL, 143 mmol), dppb (3.05 g, 7.16 mmol) and palladium acetate (1.608 g, 7.16 mmol) were placed in a steel Parr vessel, which was then purged with carbon monoxide by filling to 50 psi, then releasing the pressure, then refilled to 50 psi and heated overnight at 100° C. The mixture was diluted with water (200 mL) and extracted with EtOAc (2×300 mL), the organic layer washed with water (2×300 mL), then dried and evaporated in vacuo and the residue was triturated with ether (200 mL) and the solid collected by filtration to give ethyl 1-benzyl-5-(methylcarbamoyl)-6-oxo-1,6-dihydropyridine-3-carboxylate (21.2 g, 67.4 mmol, 94% yield).

LCMS (2 min Formic): Rt=0.99 min, [MH]$^+$=315.2.

1H NMR (400 MHz, CHCl$_3$-d) δ ppm 9.37 (br. s., 1H) 9.03 (d, J=2.4 Hz, 1H) 8.38 (d, J=2.7 Hz, 1H) 7.34-7.42 (m, 3H) 7.28-7.34 (m, 2H) 5.25 (s, 2H) 4.35 (q, J=7.1 Hz, 2H) 2.99 (d, J=4.9 Hz, 3H) 1.37 (t, J=7.2 Hz, 3H).

Intermediate 19: 1-Benzyl-5-(methylcarbamoyl)-6-oxo-1,6-dihydropyridine-3-carboxylic acid

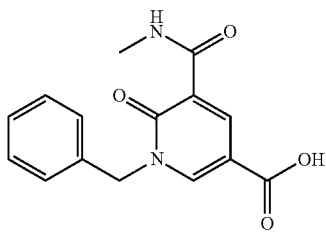 [SMILES: CNC(=O)c1cc(C(=O)O)cn(Cc2ccccc2)c1=O]

Sodium hydroxide (99 mL, 199 mmol) was added to a solution of ethyl 1-benzyl-5-(methylcarbamoyl)-6-oxo-1,6-dihydropyridine-3-carboxylate (20.8 g, 66.2 mmol) in a mixture of methanol (100 mL) and THF (100 mL) and the resulting solution was stirred for 2 h at rt, then evaporated in vacuo to approximately 100 mL volume. The mixture was diluted with water (200 mL), then filtered to remove a dark grey solid, the filtrate was washed with MTBE (200 mL), then acidified to pH 4 with 2M HCl and the resulting suspension stirred for 2 h, then filtered and the product washed with water, then dried in the vacuum oven to give 1-benzyl-5-(methylcarbamoyl)-6-oxo-1,6-dihydropyridine-3-carboxylic acid (15.2 g, 53.1 mmol, 80% yield).

LCMS (2 min High pH): Rt=0.58 min, [MH]$^+$=287.2.

1H NMR (400 MHz, DMSO-d6) δ ppm 13.19 (br. s., 1H) 9.14-9.34 (m, 1H) 8.88 (d, J=2.7 Hz, 1H) 8.70 (d, J=2.7 Hz, 1H) 7.25-7.42 (m, 5H) 5.33 (s, 2H) 2.82 (d, J=4.6 Hz, 3H).

Intermediate 20: Methyl 1-(3-methylbenzyl)-5-(methylcarbamoyl)-6-oxo-1,6-dihydropyridine-3-carboxylate

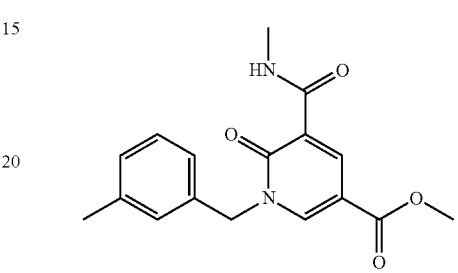

Methyl 5-(methylcarbamoyl)-6-oxo-1,6-dihydropyridine-3-carboxylate (500.2 mg, 2.380 mmol), 1-(bromomethyl)-3-methylbenzene (0.354 mL, 2.62 mmol) and potassium carbonate (140 mg, 1.013 mmol) were stirred in anhydrous DMF (10 mL) at rt under nitrogen for 4 h. The reaction mixture was concentrated in vacuo before being partitioned between water (20 mL) and ethyl acetate (20 mL). The aqueous phase was extracted with further ethyl acetate (2×20 mL) and the combined organic phases were dried by filtering through a cartridge fitted with a hydrophobic frit. The solvent was evaporated and dried in vacuo to give the desired product, as a pale yellow gum (588.2 mg). The product was used in the subsequent reaction without further purification.

LCMS (2 min Formic): Rt=1.00 min, [MH]+=315.2

Intermediate 21: 1-(3-Methylbenzyl)-5-(methylcarbamoyl)-6-oxo-1,6-dihydropyridine-3-carboxylic acid

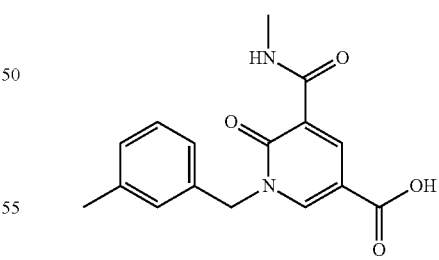

A mixture of methyl 1-(3-methylbenzyl)-5-(methylcarbamoyl)-6-oxo-1,6-dihydropyridine-3-carboxylate (583.9 mg, 1.858 mmol) and lithium hydroxide (92.4 mg, 3.86 mmol) in THF (10 mL) and water (5.00 mL) was stirred at rt under nitrogen for 16.75 h. The mixture was then acidified to pH 0 with a 2M solution of hydrochloric acid (2 mL). Water (30 mL) was added and the resulting precipitate extracted with ethyl acetate (20 mL). The layers were separated and the aqueous layer further extracted with ethyl acetate (2×20 mL). The organic layers were combined and filtered through a cartridge containing a hydrophobic frit before being concentrated in vacuo. The residue was applied to a 25 g SNAP silica cartridge as a suspension in ethyl acetate. The precipitate remaining on the top of the cartridge was removed and retained as a portion of the desired product. The cartridge was eluted with a gradient of 0-7.5% ethanol (with 0.3% acetic acid) in ethyl acetate. The required fractions were combined with the previously obtained solid, evaporated and dried in vacuo to give the desired product as a white solid (355.4 mg).

LCMS (2 min Formic): Rt=0.88 min, [MH]$^+$=301.2.

Intermediate 22: (R)-Methyl 5-(methylcarbamoyl)-6-oxo-1-(1-phenylethyl)-1,6-dihydropyridine-3-carboxylate

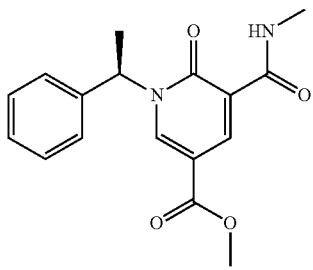 [SMILES: CNC(=O)c1cc(C(=O)OC)cn([C@H](C)c2ccccc2)c1=O]

Xantphos (1.65 g, 2.85 mmol) and palladium(II) acetate (0.877 g, 3.91 mmol) were added to a solution of (R)-5-bromo-N-methyl-2-oxo-1-(1-phenylethyl)-1,2-dihydropyridine-3-carboxamide (13.1 g, 39.1 mmol), triethylamine (16.34 mL, 117 mmol) and methanol (15.81 mL, 391 mmol) in DMF (220 mL). Carbon monoxide was sparged through the mixture until a brown suspension formed. The reaction was held under a balloon of carbon monoxide and heated to 60° C. for 4 h. The reaction mixture was cooled to rt and sparged with $N_2$ to remove any residual carbon monoxide. The reaction mixture was filtered through celite, rinsing with EtOAc and the filtrate evaporated in vacuo to a black slurry. The residue was partitioned between EtOAc (350 mL) and water (100 mL). The aqueous layer was removed, the organic layer washed (2× water [50 mL], 1× brine [50 mL]), dried over $MgSO_4$ and evaporated in vacuo to a black gum. The gum was dissolved in toluene (60 mL) and loaded on to a Biotage 340 g silica column. The column was eluted with cyclohexane:EtOAc (20→66%). The product containing fractions were evaporated to give the product (7.43 g) as a brown gum.

LCMS (2 min TFA): Rt=0.94 min, [MH]$^+$=315.2.

Intermediate 23: (R)-5-(Methylcarbamoyl)-6-oxo-1-(1-phenylethyl)-1,6-dihydropyridine-3-carboxylic acid

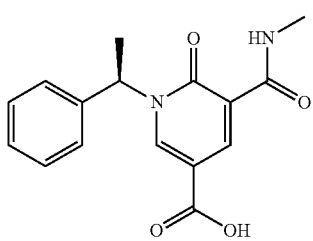 [SMILES: CNC(=O)c1cc(C(=O)O)cn([C@H](C)c2ccccc2)c1=O]

Sodium hydroxide (1.891 g, 47.3 mmol) was added to a solution of (R)-methyl 5-(methylcarbamoyl)-6-oxo-1-(1-phenylethyl)-1,6-dihydropyridine-3-carboxylate (7.43 g, 23.64 mmol) in methanol (70 mL). Water was added to the stirred suspension and the resulting solution stirred overnight. The reaction mixture was evaporated in vacuo to a pale brown solid and acidified with 2M aq. HCl (100 mL). Acetone (10 mL) was added and the suspension stirred for 15 min and filtered. The filtercake was washed [water: acetone (1:1, 20 mL), acetone (20 mL)] and dried in vacuo to give the product (6.40 g) as a beige solid.

LCMS (2 min TFA): Rt=0.82 min, [MH]$^+$=301.0.

Intermediate 24: Methyl 1-(3-methoxybenzyl)-5-(methylcarbamoyl)-6-oxo-1,6-dihydropyridine-3-carboxylate

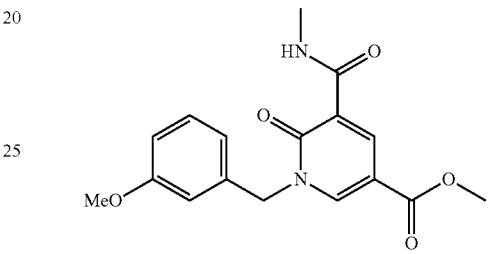

Methyl 5-(methylcarbamoyl)-6-oxo-1,6-dihydropyridine-3-carboxylate (580 mg, 2.76 mmol), 1-(bromomethyl)-3-methoxybenzene (0.580 mL, 4.14 mmol), potassium carbonate (770 mg, 5.57 mmol) and DMF (5 mL) were stirred at 90° C. for 1 h. This was washed with LiCl (20 mL), partitioned between EtOAc (40 mL) and water (40 mL), the aqueous phase was extracted with EtOAc (2×40 mL), dried over a hydrophobic frit and concentrated to give a colourless oil. This was purified by chromatography on $SiO_2$ (Biotage SNAP 100 g cartridge, eluting with 0-100% EtOAc/cyclohexane). The appropriate fractions were concentrated to give methyl 1-(3-methoxybenzyl)-5-(methylcarbamoyl)-6-oxo-1,6-dihydropyridine-3-carboxylate (683 mg, 1.861 mmol, 67.4% yield) as a white solid.

LCMS (2 min Formic): Rt=0.91 min, [MH]+=331.0.

1H NMR (400 MHz, DMSO-d6) δ ppm 9.22 (br. d, J=4.6 Hz, 1H) 8.93 (d, J=2.7 Hz, 1H) 8.70 (d, J=2.7 Hz, 1H) 7.27 (t, J=7.9 Hz, 1H) 6.92 (m, J=1.7 Hz, 1H) 6.84-6.90 (m, 2H) 5.30 (s, 2H) 3.84 (s, 3H) 3.73 (s, 3H) 2.83 (s, 3H).

Intermediate 25: 1-(3-Methoxybenzyl)-5-(methylcarbamoyl)-6-oxo-1,6-dihydropyridine-3-carboxylic acid

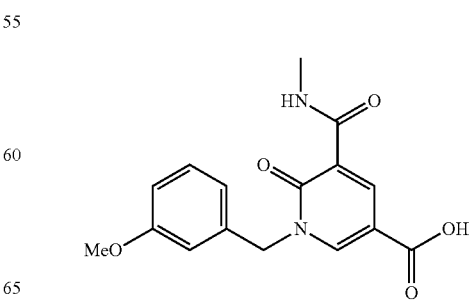

Methyl 1-(3-methoxybenzyl)-5-(methylcarbamoyl)-6-oxo-1,6-dihydropyridine-3-carboxylate (670 mg, 2.028 mmol), lithium hydroxide (146 mg, 6.08 mmol), 1,4-dioxane (3 mL) and water (3 mL) were stirred at rt for 30 min. Acetic acid (1 mL, 17.47 mmol) was added and the solution was partitioned between EtOAc (20 mL) and water (20 mL), the aqueous phase was extracted with EtOAc (2×20 mL), dried over a hydrophobic frit and concentrated to give 1-(3-methoxybenzyl)-5-(methylcarbamoyl)-6-oxo-1,6-dihydropyridine-3-carboxylic acid (641 mg, 1.824 mmol, 90% yield) as a white solid.

LCMS (2 min Formic): Rt=0.81 min, [MH]+=317.0.

1H NMR (400 MHz, DMSO-d6) δ ppm 13.09 (br. s, 1H) 9.26 (br. q, J=4.4, 4.4, 4.4 Hz, 1H) 8.84 (d, J=2.7 Hz, 1H) 8.70 (d, J=2.4 Hz, 1H) 7.27 (t, J=7.9 Hz, 1H) 6.91-6.94 (m, 1H) 6.84-6.90 (m, 2H) 5.29 (s, 2H) 3.73 (s, 3H) 2.82 (d, J=4.9 Hz, 3H).

Intermediate 26: Methyl 1-(3-hydroxybenzyl)-5-(methylcarbamoyl)-6-oxo-1,6-dihydropyridine-3-carboxylate

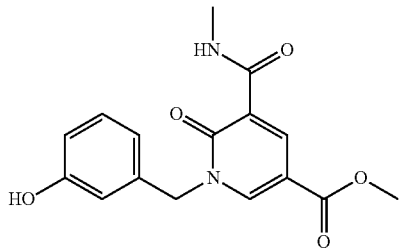

Methyl 1-(3-methoxybenzyl)-5-(methylcarbamoyl)-6-oxo-1,6-dihydropyridine-3-carboxylate (0.990 g, 3.00 mmol) in DCM (5 mL) was cooled to 0° C. under N₂ and BBr₃ (15 mL, 1 M in DCM, 15 mmol) was added dropwise and the reaction stirred for 1.5 h. The reaction was quenched with water (30 mL), extracted with DCM (2×30 mL), the aqueous layer was then extracted with EtOAc (2×30 mL). The combined organic layers were dried over a hydrophobic frit and concentrated to give 675 mg of a yellow solid. This was purified by chromatography on SiO₂ (Biotage SNAP 50 g cartridge, eluting with 40-100% EtOAc/cyclohexane). The appropriate fractions were concentrated to give methyl 1-(3-hydroxybenzyl)-5-(methylcarbamoyl)-6-oxo-1,6-dihydropyridine-3-carboxylate (473 mg, 1.346 mmol, 44.9% yield) as a white solid.

LCMS (2 min Formic): Rt=0.74 min, [MH]+=317.0.

1H NMR (400 MHz, DMSO-d6) δ ppm 9.46 (br. s, 1H) 9.23 (br. d, J=4.6 Hz, 1H) 8.90 (d, J=2.7 Hz, 1H) 8.70 (d, J=2.7 Hz, 1H) 7.05-7.20 (m, 1H) 6.65-6.76 (m, 3H) 5.26 (s, 2H) 3.78-3.90 (m, 3H) 2.82 (d, J=4.9 Hz, 3H).

Intermediate 27: Methyl 1-(3-(2-hydroxyethoxy)benzyl)-5-(methylcarbamoyl)-6-oxo-1,6-dihydropyridine-3-carboxylate

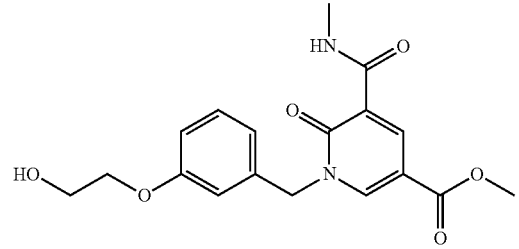 [SMILES: CNC(=O)c1cc(C(=O)OC)cn(Cc2cccc(OCCO)c2)c1=O]

Methyl 1-(3-hydroxybenzyl)-5-(methylcarbamoyl)-6-oxo-1,6-dihydropyridine-3-carboxylate (450 mg, 1.423 mmol), 1,3-dioxolan-2-one (475 mg, 5.39 mmol), potassium carbonate (600 mg, 4.34 mmol) and DMF (10 mL) were heated at 90° C. for 5 h. The solution was partitioned between EtOAc (40 mL) and LiCl soln. (40 mL), the aqueous phase was extracted with EtOAc (2×40 mL), dried over a hydrophobic frit and concentrated to give 900 mg of a yellow oil. This was purified by chromatography on SiO₂ (Biotage SNAP 10 g cartridge, eluting with 0-100% (25% EtOH in EtOAc)/cyclohexane). The appropriate fractions were concentrated to give methyl 1-(3-(2-hydroxyethoxy)benzyl)-5-(methylcarbamoyl)-6-oxo-1,6-dihydropyridine-3-carboxylate (446 mg, 1.114 mmol, 78% yield) as a colourless oil.

LCMS (2 min Formic): Rt=0.74 min, [MH]+=361.1.

1H NMR (400 MHz, DMSO-d6) δ ppm 9.22 (br. q, J=4.9, 4.9, 4.9 Hz, 1H) 8.94 (d, J=2.7 Hz, 1H) 8.70 (d, J=2.4 Hz, 1H) 7.25 (t, J=7.8 Hz, 1H) 6.82-6.94 (m, 3H) 5.30 (s, 2H) 4.81 (t, J=5.6 Hz, 1H) 3.95 (t, J=5.0 Hz, 2H) 3.84 (s, 3H) 3.69 (q, J=5.3 Hz, 2H) 2.82 (d, J=4.6 Hz, 3H).

Intermediate 28: 1-(3-(2-Hydroxyethoxy)benzyl)-5-(methylcarbamoyl)-6-oxo-1,6-dihydropyridine-3-carboxylic acid

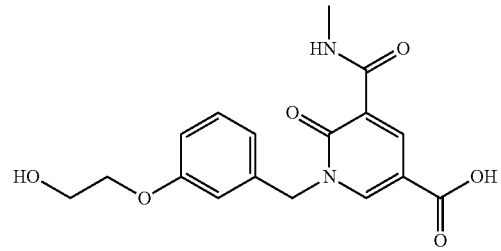 [SMILES: CNC(=O)c1cc(C(=O)O)cn(Cc2cccc(OCCO)c2)c1=O]

Methyl 1-(3-(2-hydroxyethoxy)benzyl)-5-(methylcarbamoyl)-6-oxo-1,6-dihydropyridine-3-carboxylate (440 mg, 1.221 mmol), lithium hydroxide (86 mg, 3.59 mmol), 1,4-dioxane (3 mL) and water (3 mL) were stirred at rt for 1 h. Acetic acid (1 mL, 17.47 mmol) was added and the solution was partitioned between EtOAc (20 mL) and water (20 mL), the aqueous phase was extracted with EtOAc (2×20 mL), dried over a hydrophobic frit and concentrated to give 1-(3-(2-hydroxyethoxy)benzyl)-5-(methylcarbannoyl)-6-oxo-1,6-dihydropyridine-3-carboxylic acid (343 mg, 0.891 mmol, 73.0% yield) as a white solid.

LCMS (2 min Formic): Rt=0.66 min, [MH]+=347.0.

1H NMR (400 MHz, DMSO-d6) δ ppm 9.27 (br. q, J=4.2, 4.2, 4.2 Hz, 1H) 8.85 (d, J=2.4 Hz, 1H) 8.71 (d, J=2.4 Hz, 1H) 7.27 (t, J=7.8 Hz, 1H) 6.80-6.99 (m, 3H) 5.30 (s, 2H) 4.82 (t, J=5.5 Hz, 1H) 3.96 (app. t, J=5.0 Hz, 2H) 3.70 (ABq, J=5.1 Hz, 2H) 2.83 (d, J=4.9 Hz, 3H).

Intermediate 29: Butyl 1-(2-fluoro-3-methylbenzyl)-5-(methylcarbamoyl)-6-oxo-1,6-dihydropyridine-3-carboxylate

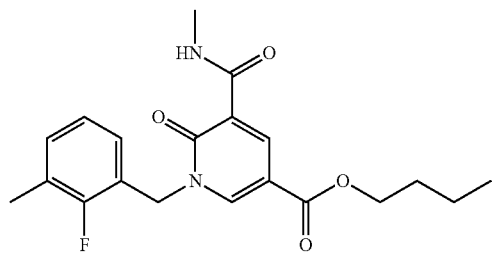 [SMILES: CCCCOC(=O)c1cc(C(=O)NC)c(=O)n(Cc2cccc(C)c2F)c1]

A stirred suspension of butyl 5-(methylcarbannoyl)-6-oxo-1,6-dihydropyridine-3-carboxylate (695.9 mg, 2.76 mmol) and potassium carbonate (769.4 mg, 5.57 mmol) in DMF (4 mL) at rt had a solution of 1-(bromomethyl)-2-fluoro-3-methylbenzene (607.4 mg, 2.99 mmol) in DMF (6 mL) added to it. The mixture was stirred at rt under nitrogen for 73 h before being partitioned between water (20 mL) and ethyl acetate (25 mL). The organic phase was washed with further water (20 mL) and the combined aqueous phases back-extracted with ethyl acetate (25 mL). The combined organic phases were dried by filtering through a cartridge fitted with a hydrophobic frit and the solvent was evaporated in vacuo to give a pale yellow oil which crystallised upon standing overnight to a pale yellow solid. The solid was purified by being re-dissolved in dichloromethane (ca. 5 mL) and applied to a 50 g SNAP silica cartridge which was eluted with a gradient of 20-60% ethyl acetate in cyclohexane. The required fractions were combined and evaporated in vacuo to give the desired product as a white solid (958.7 mg).

LCMS (2 min Formic): Rt=1.26 min, [MH]+=375.2.

Intermediate 30: 1-(2-Fluoro-3-methylbenzyl)-5-(methylcarbamoyl)-6-oxo-1,6-dihydropyridine-3-carboxylic acid

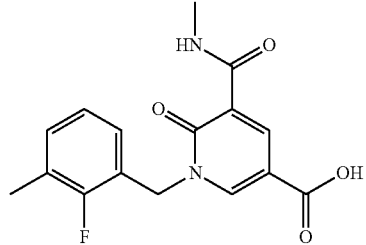 [SMILES: CNC(=O)c1cc(C(=O)O)cn(Cc2cccc(C)c2F)c1=O]

To a stirred solution of butyl 1-(2-fluoro-3-methylbenzyl)-5-(methylcarbamoyl)-6-oxo-1,6-dihydropyridine-3-carboxylate (953.7 mg, 2.55 mmol) in acetonitrile (10 mL) and THF (10 mL) under nitrogen was added lithium hydroxide (1.0 M aqueous solution) (5.1 mL, 5.10 mmol) and the mixture was stirred at rt for 2.5 h. The volatiles were evaporated from the mixture in vacuo and the residue dried in vacuo before being partitioned between 2 M aqueous hydrochloric acid (20 mL) and ethyl acetate (150 mL) [solid was poorly soluble in both phases]. The aqueous phase was extracted with further ethyl acetate (75 mL) and the combined organic phases washed with water (20 mL) and saturated brine solution (30 mL). The organic phase was dried by filtering through a cartridge fitted with a hydrophobic frit and the solvent evaporated in vacuo. The solid residue was triturated twice with methanol (10 mL+5 mL) and the solid dried in vacuo to give the desired product as a white solid (621.7 mg).

LCMS (2 min Formic): Rt=0.90 min, [MH]+=319.1.

Intermediate 31: Butyl 5-(methylcarbamoyl)-6-oxo-1-((1-tosyl-1H-indol-4-yl)methyl)-1,6-dihydropyridine-3-carboxylate

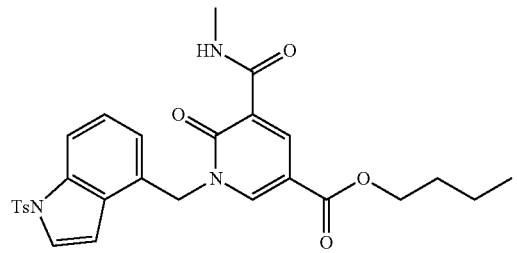 [SMILES: CCCCOC(=O)c1cc(C(=O)NC)c(=O)n(Cc2cccc3c2ccn3S(=O)(=O)c2ccc(C)cc2)c1]

To a solution of butyl 5-(methylcarbannoyl)-6-oxo-1,6-dihydropyridine-3-carboxylate (447 mg, 1.772 mmol) in DMF (11.8 mL) was added potassium carbonate (490 mg, 3.54 mmol) and 4-(bromomethyl)-1-tosyl-1H-indole (1033 mg, 2.84 mmol). The mixture was stirred at rt for 2 h. The reaction was quenched with water (1.596 mL, 89 mmol) and poured onto water (100 mL) and saturated aqueous lithium chloride (20 mL). The aqueous phase was extracted with ethyl acetate (3×30 mL) and the combined organics were washed with brine (10 mL), dried through a hydrophobic frit and evaporated in vacuo to yield the crude product (1.74 g). The residue was loaded in dichloromethane onto a 50 g SNAP silica cartridge and purified via Biotage SP4 flash chromatography, eluting from 20-100% ethyl acetate/cyclohexane. The relevant fractions were combined and evaporated in vacuo to yield the pure product—butyl 5-(methylcarbamoyl)-6-oxo-1-((1-tosyl-1H-indol-4-yl)methyl)-1,6-dihydropyridine-3-carboxylate (907 mg, 1.609 mmol, 91% yield) as a white solid.

LCMS (2 min Formic): Rt=1.34 min, [MH]+=536.1.

Intermediate 32: 1-((1H-Indol-4-yl)methyl)-5-(methylcarbamoyl)-6-oxo-1,6-dihydropyridine-3-carboxylic acid

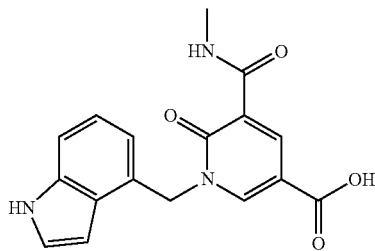 [SMILES: CNC(=O)c1cc(C(=O)O)cn(Cc2cccc3[nH]ccc23)c1=O]

To a solution of butyl 5-(methylcarbamoyl)-6-oxo-1-((1-tosyl-1H-indol-4-yl)methyl)-1,6-dihydropyridine-3-carboxylate (821 mg, 1.533 mmol) in methanol (1.703 mL) and THF (3.406 mL) stirred under nitrogen at rt was added solid cesium carbonate (3995 mg, 12.26 mmol) in one charge. The reaction mixture was stirred at 70° C. for 3 h. The reaction mixture was concentrated in vacuo, before diluting with 1,4-dioxane (1.703 mL) and water (1.703 mL). The mixture was stirred at 70° C. for 4.5 h. The reaction mixture was poured onto saturated sodium bicarbonate (30 mL) and extracted with ethyl acetate (3×10 mL). The aqueous phase was acidified with 2M HCl and extracted with ethyl acetate (8×30 mL). Following extraction, a solid precipitate remained in the organic phase which was filtered off to give some desired crude product (251 mg). The filtrate from workup was dried through a hydrophobic frit and evaporated in vacuo to yield a brown solid. The solid was triturated with ether (30 mL) and filtered to give further product (539 mg). This residue was suspended in water (20 mL) and brought to pH 4 with 2M HCl. The suspension was filtered, washed with water (2×5 mL) and diethyl ether (2×10 mL). The collected solid (213 mg) was suspended in dichloromethane (10 mL) and combined with the previous batch of crude product. The combined suspension was sonicated and blown down under a stream of nitrogen and dried in vacuo to give the final product 1-((1H-indol-4-yl)methyl)-5-(methylcarbamoyl)-6-oxo-1,6-dihydropyridine-3-carboxylic acid (432 mg, 1.222 mmol, 80% yield).

LCMS (2 min Formic): Rt=0.77 min, [MH]$^+$=326.2.

EXAMPLES

Example 1: 1-Benzyl-N$^5$-ethyl-N$^3$-methyl-2-oxo-1,2-dihydropyridine-3,5-dicarboxamide

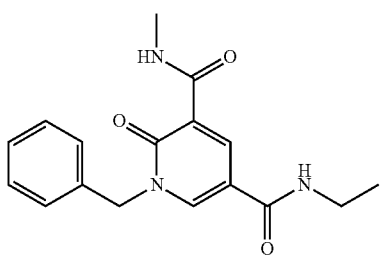 [SMILES: CCNC(=O)c1cc(C(=O)NC)c(=O)n(Cc2ccccc2)c1]

To a solution of 1-benzyl-5-(methylcarbamoyl)-6-oxo-1,6-dihydropyridine-3-carboxylic acid (250 mg, 0.873 mmol) in DMF (2.5 mL) was added HATU (365 mg, 0.961 mmol) followed by DIPEA (0.305 mL, 1.747 mmol). The resulting reaction mixture was stirred at rt under N$_2$ for 15 min. Ethanamine (2M in THF) (0.873 mL, 1.747 mmol) was then added and the reaction stirred for ~1 h. The reaction mixture was diluted with EtOAc (10 mL) and water (10 mL) and the layers separated. The aqueous layer was extracted with further EtOAc (2×20 mL) and the combined organics back extracted with water (2×10 mL) and brine (10 mL). The organics were dried (Na$_2$SO$_4$) and concentrated in vacuo. The crude product was taken up in DCM and purified by SP4 flash chromatography (10→50% (25% EtOH/EtOAc)/cyclohexane). The appropriate fractions were collected and concentrated in vacuo to afford the desired product as a cream solid—1-benzyl-N5-ethyl-N3-methyl-2-oxo-1,2-dihydropyridine-3,5-dicarboxamide (242 mg, 0.772 mmol, 88% yield).

LCMS (2 min Formic): Rt=0.80 min, [MH]$^+$=314.1.

Example 2: 1-Benzyl-N$^3$-methyl-2-oxo-N$^5$-propyl-1,2-dihydropyridine-3,5-dicarboxamide

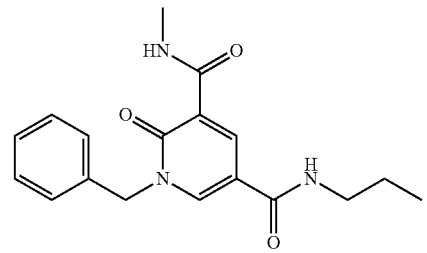 [SMILES: CCCNC(=O)c1cc(C(=O)NC)c(=O)n(Cc2ccccc2)c1]

2,4,6-Trichlorophenyl 1-benzyl-5-(methylcarbamoyl)-6-oxo-1,6-dihydropyridine-3-carboxylate (50 mg, 0.107 mmol), propan-1-amine (0.02 mL, 0.243 mmol), N,N-dimethylpyridin-4-amine (5 mg, 0.041 mmol), triethylamine (0.05 mL, 0.359 mmol) and THF (1 mL) were stirred at 45° C. under N$_2$ for 1 h. The white suspension formed was concentrated to give 80 mg of a white solid. This was purified by chromatography on SiO$_2$ (Biotage SNAP 10 g cartridge, eluting with 0-100% ethyl acetate/cyclohexane). The desired fractions were concentrated to give 1-benzyl-N3-methyl-2-oxo-N5-propyl-1,2-dihydropyridine-3,5-dicarboxamide (33 mg, 0.091 mmol, 84% yield) as a white solid LCMS (2 min Formic): Rt=0.92 min, [MH]$^+$=328.

1H NMR (400 MHz, MeOH-d4) δ ppm 8.85 (d, J=2.7 Hz, 1H) 8.56 (d, J=2.9 Hz, 1H) 7.23-7.43 (m, 5H) 5.32 (s, 2H) 3.27-3.33 (obs, 2H) 2.95 (s, 3H) 1.61 (sxt, J=7.3 Hz, 2H) 0.96 (t, J=7.3 Hz, 3H).

Example 3: 1-Benzyl-N$^5$-butyl-N$^3$-methyl-2-oxo-1,2-dihydropyridine-3,5-dicarboxamide

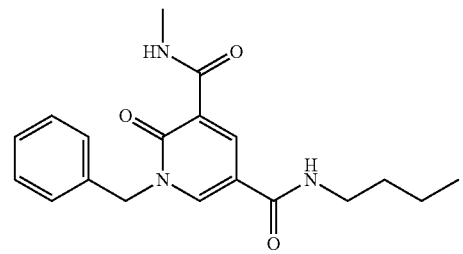 [SMILES: CCCCNC(=O)c1cc(C(=O)NC)c(=O)n(Cc2ccccc2)c1]

2,4,6-Trichlorophenyl 1-benzyl-5-(methylcarbamoyl)-6-oxo-1,6-dihydropyridine-3-carboxylate (51 mg, 0.110 mmol), N,N-dimethylpyridin-4-amine (2.68 mg, 0.022 mmol), butan-1-amine (0.03 mL, 0.304 mmol), triethylamine (0.06 mL, 0.430 mmol) and THF (1 mL) were stirred at 45° C. under $N_2$ for 3 h. The solution was concentrated to give ~90 mg of an off white residue which was purified by chromatography on $SiO_2$ (Biotage SNAP 10 g cartridge, eluting with 0-50% (25% EtOH in EtOAc)/cyclohexane). The desired fractions were concentrated to give 1-benzyl-N5-butyl-N3-methyl-2-oxo-1,2-dihydropyridine-3,5-dicarboxamide (35 mg, 0.092 mmol, 84% yield) as a white solid.

LCMS (2 min Formic): Rt=0.96 min, $[MH]^+=342$.

Example 4: 1-Benzyl-N5-isopentyl-N3-methyl-2-oxo-1,2-dihydropyridine-3,5-dicarboxamide

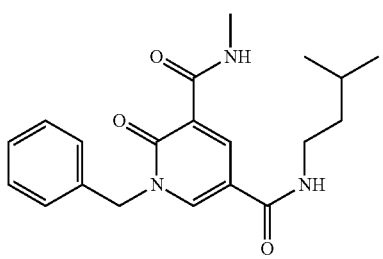 [SMILES: CNC(=O)c1cc(C(=O)NCCC(C)C)cn(Cc2ccccc2)c1=O]

Triethylamine (0.060 mL, 0.429 mmol), DMAP (6.56 mg, 0.054 mmol), 2,4,6-trichlorophenyl 1-benzyl-5-(methylcarbamoyl)-6-oxo-1,6-dihydropyridine-3-carboxylate (50 mg, 0.107 mmol) and 3-methylbutan-1-amine (18.72 mg, 0.215 mmol) were dissolved in THF (1.5 mL) and stirred at 45° C. under nitrogen for 1 h. The reaction was concentrated under vacuum, loaded in DCM and purified by Biotage Isolera SNAP 25 g silica flash chromatography using a gradient of 0-100% cyclohexane/ethyl acetate. The product containing fractions were combined and purified by MDAP (High pH), the product containing fractions were combined and concentrated under vacuum to give the product (6 mg).

LCMS (2 min Formic): Rt=1.04 min, $[MH]^+=356.3$

Example 5

1-Benzyl-$N^3$-methyl-$N^5$-(4-(methylamino)-4-oxobutyl)-2-oxo-1,2-dihydropyridine-3,5-dicarboxamide

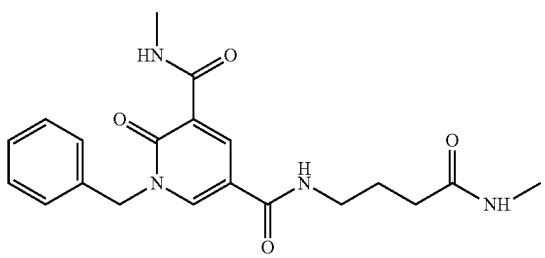 [SMILES: CNC(=O)CCCNC(=O)c1cc(C(=O)NC)c(=O)n(Cc2ccccc2)c1]

1-Benzyl-5-bromo-N-methyl-2-oxo-1,2-dihydropyridine-3-carboxamide (150 mg, 0.467 mmol), cobalt carbonyl (39.9 mg, 0.117 mmol), DMAP (114 mg, 0.934 mmol), palladium (II) acetate (5.24 mg, 0.023 mmol), 4-amino-N-methylbutanamide hydrochloride (86 mg, 0.560 mmol, commercially available from, for example, ChemBridge) and xantphos (13.51 mg, 0.023 mmol) were added to a micowave vial. The vial was sealed and THF (3 mL) added and heated in a Biotage Initiator microwave at 80° C. for 40 min. The resulting mixture was diluted with water (20 mL) and extracted with ethyl acetate (20 mL). The organic layer was dried, concentrated under vacuum, dissolved in DMSO and purified further by MDAP (High pH) and the product containing fractions combined and concentrated under vacuum to give the product (63 mg) as a white solid.

LCMS (2 min Formic): Rt=0.72 min, $[MH]^+=385.4$.

Example 6: tert-Butyl (3-(1-benzyl-5-(methylcarbamoyl)-6-oxo-1,6-dihydropyridine-3-carboxamido)propyl)carbamate

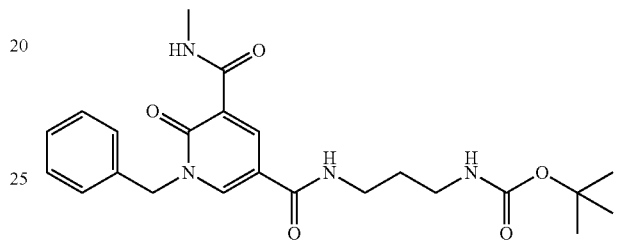

1-Benzyl-5-(methylcarbamoyl)-6-oxo-1,6-dihydropyridine-3-carboxylic acid (120 mg, 0.419 mmol) was taken up in DMF (2 mL) and HATU (175 mg, 0.461 mmol) followed by DIPEA (0.146 mL, 0.838 mmol) were added. The reaction mixture was allowed to stir for 5 min, then tert-butyl (3-aminopropyl)carbamate (0.073 mL, 0.419 mmol, commercially available from, for example, Sigma-Aldrich) was added and the reaction allowed to stir for 1 h. The solution was concentrated under vacuum and redissolved in ethyl acetate (15 mL) and washed with citric acid (1 M, 3×10 mL), saturated $NaHCO_3$ (3×10 mL), water (10 mL) and brine (10 mL). The solution was dried and concentrated under vacuum. The orange solid was purified by Biotage Isolera flash chromatography using a SNAP 10 g silica cartridge and a gradient of 0-100% ethyl acetate/cyclohexane. The appropriate fractions were combined and concentrated under vacuum to give the desired product (120 mg, 0.271 mmol, 64.7% yield) as a white solid.

LCMS (2 min Formic): Rt=0.98 min, $[MH]^+=443.2$.

Example 7: 1-Benzyl-$N^3$-methyl-2-oxo-$N^5$-(3,3,3-trifluoropropyl)-1,2-dihydropyridine-3,5-dicarboxamide

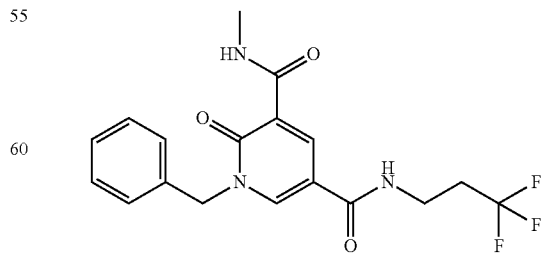

1-Benzyl-5-(methylcarbamoyl)-6-oxo-1,6-dihydropyridine-3-carboxylic acid (50 mg, 0.175 mmol) was taken up in DMF (2 mL) and HATU (73.0 mg, 0.192 mmol) followed by DIPEA (0.061 mL, 0.349 mmol) were added. The reaction mixture was allowed to stir for 5 min, then 3,3,3-trifluoropropan-1-amine (0.017 mL, 0.175 mmol) was added and the reaction allowed to stir overnight. Further 3,3,3-trifluoropropan-1-amine (0.017 mL, 0.175 mmol) was added and the solution allowed to stir for 1 h. HATU (73.0 mg, 0.192 mmol) was added and the reaction allowed to stir for 1 h. The reaction mixture was concentrated under vacuum and purified by MDAP (High pH). The appropriate fractions were combined and concentrated under vacuum to give the desired product (60 mg, 0.157 mmol, 90% yield).

LCMS (2 min Formic): Rt=0.94 min, [MH]$^+$=382.1.

Example 8: $N^5$-(2-(1H-Imidazol-5-yl)ethyl)-1-benzyl-$N^3$-methyl-2-oxo-1,2-dihydropyridine-3,5-dicarboxamide

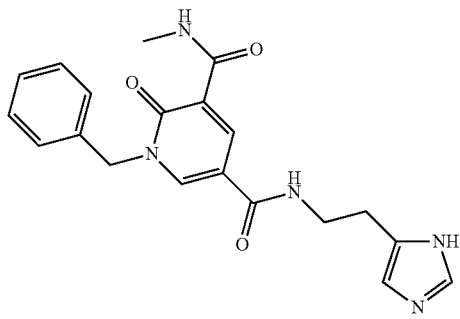 [SMILES: CNC(=O)c1cc(C(=O)NCCc2cnc[nH]2)cn(Cc2ccccc2)c1=O]

To a solution of HATU (83.8 mg, 0.220 mmol), 2-(1H-imidazol-5-yl)ethanamine (41.2 mg, 0.371 mmol, commercially available from, for example, Sigma-Aldrich) and 1-benzyl-5-(methylcarbannoyl)-6-oxo-1,6-dihydropyridine-3-carboxylic acid (52.8 mg, 0.184 mmol) in DMF (1 mL) was added DIPEA (64 µL, 0.369 mmol). The mixture was stirred at rt for 3 h. Further HATU (79.9 mg, 0.210 mmol) and DIPEA (64 µL, 0.369 mmol) were added and stirring continued for 1.25 h before being concentrated under a stream of nitrogen. The solution was diluted to a volume of 1 mL using methanol and was directly purified by MDAP (formic). The required fractions were evaporated under a stream of nitrogen before being dissolved in a 1:1 mixture of dichloromethane/methanol (3×4 mL), combined and concentrated under a stream of nitrogen and dried in vacuo to give the desired product as a colourless solid—N5-(2-(1H-imidazol-5-yl)ethyl)-1-benzyl-N3-methyl-2-oxo-1,2-dihydropyridine-3,5-dicarboxamide (46.5 mg, 0.123 mmol, 66.5% yield).

LCMS (2 min Formic): Rt=0.51 min, [MH]+=380.4.

Example 9: Methyl 4-(1-benzyl-5-(methylcarbamoyl)-6-oxo-1,6-dihydropyridine-3-carboxamido)butanoate

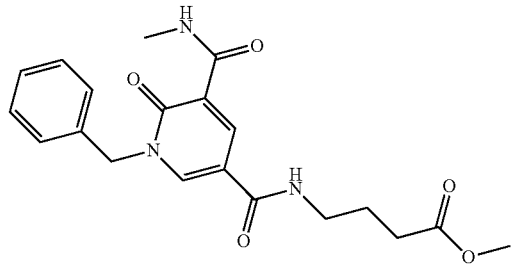 [SMILES: CNC(=O)c1cc(C(=O)NCCCC(=O)OC)cn(Cc2ccccc2)c1=O]

To a solution of 1-benzyl-5-(methylcarbannoyl)-6-oxo-1,6-dihydropyridine-3-carboxylic acid (48.2 mg, 0.168 mmol), methyl 4-aminobutanoate, hydrochloride (41.1 mg, 0.268 mmol) and HATU (80.1 mg, 0.211 mmol) in DMF (1 mL), was added DIPEA (0.059 mL, 0.337 mmol). The mixture was stirred at rt for 2 h before being concentrated under a stream of nitrogen. The solution was made up to 1 mL with methanol and directly purified by MDAP (formic). The required fraction was evaporated under a stream of nitrogen before being dissolved in a 1:1 mixture of dichloromethane/methanol (4 mL), concentrated under a stream of nitrogen and dried in vacuo to give the desired product as a white solid—methyl 4-(1-benzyl-5-(methylcarbamoyl)-6-oxo-1,6-dihydropyridine-3-carboxannido)butanoate (45.4 mg, 0.118 mmol, 70.0% yield).

LCMS (formic) [MH]$^+$=0.85 min, [MH]$^+$=386.3.

Example 10: 1-Benzyl-$N^3$-methyl-2-oxo-$N^5$-(2-(pyridin-2-yl)ethyl)-1,2-dihydropyridine-3,5-dicarboxamide

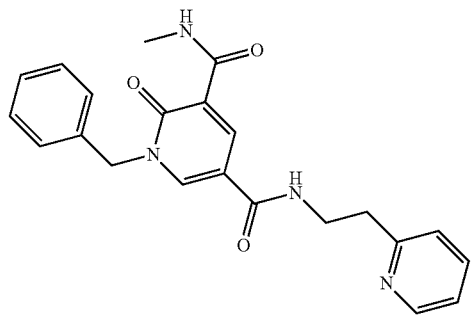 [SMILES: CNC(=O)c1cc(C(=O)NCCc2ccccn2)cn(Cc2ccccc2)c1=O]

To a solution of 1-benzyl-5-(methylcarbannoyl)-6-oxo-1,6-dihydropyridine-3-carboxylic acid (50.8 mg, 0.177 mmol), 2-(pyridin-2-yl)ethanamine (0.042 mL, 0.355 mmol, commercially available from, for example, Sigma-Aldrich) and HATU (82.1 mg, 0.216 mmol) in DMF (1 mL) was added DIPEA (0.062 mL, 0.355 mmol). The mixture was stirred at rt for 2 h before being concentrated under a stream of nitrogen. The residue was made up to 1 mL with methanol and directly purified by MDAP (formic). The required fraction was evaporated under a stream of nitrogen before being dissolved in a 1:1 mixture of dichloromethane/methanol (4 mL), concentrated under a stream of nitrogen and dried in vacuo to give the desired product as a white solid—1-benzyl-N3-methyl-2-oxo-N5-(2-(pyridin-2-yl)ethyl)-1,2-dihydropyridine-3,5-dicarboxamide (49.4 mg, 0.127 mmol, 71.3% yield).

LCMS (2 min formic): Rt=0.55 min, [MH]$^+$=391.3.

Example 11: N$^5$-(3-(1H-Imidazol-2-yl)propyl)-1-benzyl-N$^3$-methyl-2-oxo-1,2-dihydropyridine-3,5-dicarboxamide

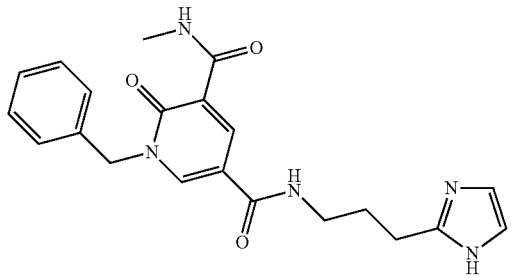 [SMILES: CNC(=O)c1cc(C(=O)NCCCc2ncc[nH]2)cn(Cc2ccccc2)c1=O]

To a solution of 1-benzyl-5-(methylcarbannoyl)-6-oxo-1,6-dihydropyridine-3-carboxylic acid (52.7 mg, 0.184 mmol), 3-(1H-imidazol-2-yl)propan-1-amine (47.7 mg, 0.381 mmol) and HATU (85.2 mg, 0.224 mmol) in DMF (1 mL) was added DIPEA (0.064 mL, 0.368 mmol). The mixture was stirred at rt for 1.75 h. Further DIPEA (0.064 mL, 0.368 mmol) and HATU (82.3 mg, 0.216 mmol) were added and stirring continued for 0.75 h. The reaction mixture was concentrated under a stream of nitrogen, made up to 1 mL with methanol and directly purified by MDAP (formic). The required fractions were individually evaporated under a stream of nitrogen before being dissolved in a 1:1 mixture of dichloromethane/methanol (2×4 mL), combined, concentrated under a stream of nitrogen and dried in vacuo to give the desired product as a white solid—N5-(3-(1H-imidazol-2-yl)propyl)-1-benzyl-N3-methyl-2-oxo-1,2-dihydropyridine-3,5-dicarboxamide (35.9 mg, 0.091 mmol, 49.6% yield).

LCMS (2 min formic): Rt=0.53 min, [MH]$^+$=394.3.

Example 12: —N$^5$-(2-(1H-Pyrazol-4-yl)ethyl)-1-benzyl-N$^3$-methyl-2-oxo-1,2-dihydropyridine-3,5-dicarboxamide

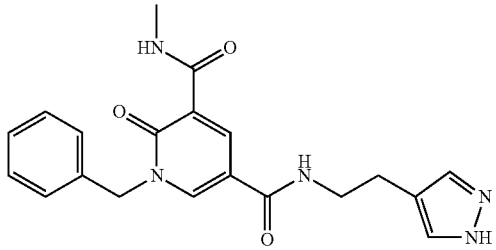 [SMILES: CNC(=O)c1cc(C(=O)NCCc2cn[nH]c2)cn(Cc2ccccc2)c1=O]

1-Benzyl-5-(methylcarbamoyl)-6-oxo-1,6-dihydropyridine-3-carboxylic acid (50 mg, 0.175 mmol) was taken up in DMF (2 mL) and HATU (73.0 mg, 0.192 mmol) followed by DIPEA (0.183 mL, 1.048 mmol) were added. The reaction mixture was allowed to stir for 5 min, then 2-(1H-pyrazol-4-yl)ethanamine (19.41 mg, 0.175 mmol, commercially available from, for example, Fluorochem) was added and the reaction allowed to stir for 1 h. The reaction mixture was concentrated under vacuum and purified by MDAP (High pH). The appropriate fractions were combined and concentrated under vacuum to give the desired product (42 mg, 0.111 mmol, 63.4% yield) as a white solid.

LCMS (2 min Formic): Rt=0.74 min, [MH]$^+$=380.2

Example 13: N$^5$-(2-(1H-Pyrazol-4-yl)ethyl)-N$^3$-methyl-1-(3-methylbenzyl)-2-oxo-1,2-dihydropyridine-3,5-dicarboxamide

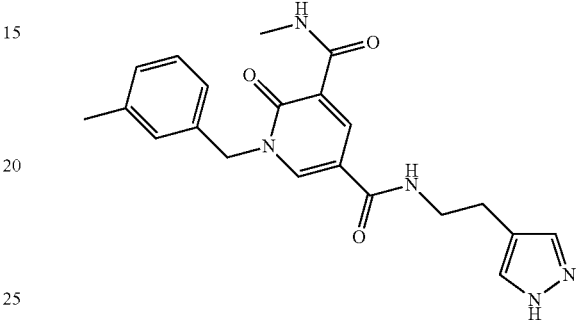

To a solution of 1-(3-methylbenzyl)-5-(methylcarbamoyl)-6-oxo-1,6-dihydropyridine-3-carboxylic acid (104.7 mg, 0.349 mmol), 2-(1H-pyrazol-4-yl)ethanamine, dihydrochloride (81.8 mg, 0.444 mmol, commercially available from, for example, Fluorochem) and HATU (162 mg, 0.426 mmol) in DMF (3 mL) was added DIPEA (0.244 mL, 1.395 mmol). The mixture was stirred at rt for 1.5 h before being concentrated under a stream of nitrogen. The residue was made up to 2 mL with a 1:1 mixture of DMSO/methanol and directly purified by MDAP (formic). The required fractions were individually concentrated under a stream of nitrogen before being dissolved in a 1:1 mixture of dichloromethane/methanol (2×4 mL), combined, concentrated under a stream of nitrogen and dried in vacuo to give the desired product as a white solid—N5-(2-(1H-pyrazol-4-yl)ethyl)-N3-methyl-1-(3-methylbenzyl)-2-oxo-1,2-dihydropyridine-3,5-dicarboxamide (58.5 mg, 0.149 mmol, 42.6% yield)

LCMS (2 min formic) Rt=0.82 min, [MH]$^+$=394.3.

1H NMR (400 MHz, DMSO-d6) δ ppm 9.38 (br. q, J=4.4, 4.4, 4.4 Hz, 1H) 8.83 (d, J=2.7 Hz, 1H) 8.71 (d, J=2.7 Hz, 1H) 8.66 (br. t, J=5.5, 5.5 Hz, 1H) 7.48 (s, 2H) 7.25 (t, J=7.6 Hz, 1H) 7.09-7.16 (m, 3H) 5.26 (s, 2H) 3.36-3.45 (m, 2H) 2.84 (d, J=4.9 Hz, 3H) 2.69 (t, J=7.3 Hz, 2H) 2.29 (s, 3H).

Example 14: N$^5$-Ethyl-N$^3$-methyl-1-(3-methylbenzyl)-2-oxo-1,2-dihydropyridine-3,5-dicarboxamide

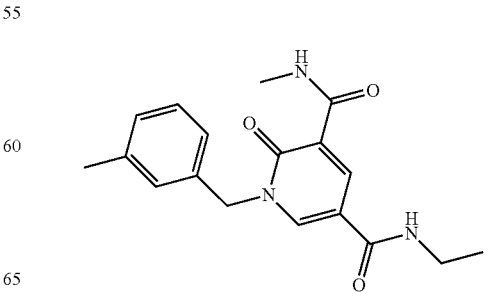

To a solution of 1-(3-methylbenzyl)-5-(methylcarbamoyl)-6-oxo-1,6-dihydropyridine-3-carboxylic acid (120.7 mg, 0.402 mmol) and HATU (184.8 mg, 0.486 mmol) in DMF (3 mL) was added ethanamine (2M solution in THF) (0.402 mL, 0.804 mmol) and DIPEA (0.140 mL, 0.804 mmol). The mixture was stirred at rt for 1.5 h before being concentrated under a stream of nitrogen. The residue was made up to 2 mL with a 1:1 mixture of DMSO/methanol and directly purified by MDAP (formic). The required fractions were individually concentrated under a stream of nitrogen before being dissolved in a 1:1 mixture of dichloromethane/methanol (2×4 mL), combined, concentrated under a stream of nitrogen and dried in vacuo to give the desired product as a white solid—N5-ethyl-N3-methyl-1-(3-methylbenzyl)-2-oxo-1,2-dihydropyridine-3,5-dicarboxamide (114.1 mg, 0.349 mmol, 87% yield)

LCMS (2 min formic): Rt=0.89 min, [MH]$^+$=328.2

1H NMR (400 MHz, DMSO-d6) δ ppm 9.34-9.42 (m, 1H) 8.82 (d, J=2.9 Hz, 1H) 8.70 (d, J=2.7 Hz, 1H) 8.56 (t, J=5.3 Hz, 1H) 7.24 (t, J=7.6 Hz, 1H) 7.07-7.16 (m, 3H) 5.25 (s, 2H) 3.21-3.29 (obs, 2H) 2.83 (d, J=4.9 Hz, 3H) 2.28 (s, 3H) 1.11 (t, J=7.2 Hz, 3H)

Examples 15-16: Amide array of (R)-5-(methylcarbamoyl)-6-oxo-1-(1-phenylethyl)-1,6-dihydropyridine-3-carboxylic acid (intermediate XX)

To a stock solution of (R)-5-(methylcarbamoyl)-6-oxo-1-(1-phenylethyl)-1,6-dihydropyridine-3-carboxylic acid (30 mg, 0.1 mmol) and HATU (380 mg) in DMF (5 mL) was added DIPEA (520 μL). The mixture was shaken and sonicated to aid dispersion. The mixture was aliquoted (0.5 mL) to a set of preweighed amines (0.100 mmol) in micronic vials. These were capped and shaken and left to stand at rt for 18 h. The samples were purified by MDAP (High pH). The solvent was dried under a stream of nitrogen to give the required products. Example 15 had additional DIPEA (100 μL) added to the reaction mixture on addition of the DIPEA.

| Ex No. | Reagent Name | Structure | MW | Reagent Mass (g) | Reagent Volume (mL) | mmol |
|---|---|---|---|---|---|---|
| 15 | 2-(1H-pyrazol-4-yl)ethanamine | 2•HCl | 111.15 | 0.013 | — | 0.100 |
| 16 | ethanamine | 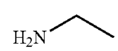 | 45.08 | 0.005 | — | 0.100 |

| Ex no. | Name | Structure | Mass (mg) | Yield (%) | [MH]+ | Rt (min) |
|---|---|---|---|---|---|---|
| 15 | (R)-N$^5$-(2-(1H-Pyrazol-4-yl)ethyl)-N$^3$-methyl-2-oxo-1-(1-phenylethyl)-1,2-dihydropyridine-3,5-dicarboxamide | 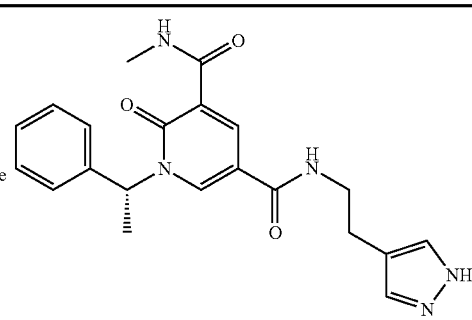 | 25.6 | 58.6 | 394.0 | 0.76 |
| 16 | (R)-N$^5$-Ethyl-N$^3$-methyl-2-oxo-1-(1-phenylethyl)-1,2-dihydropyridine-3,5-dicarboxamide | 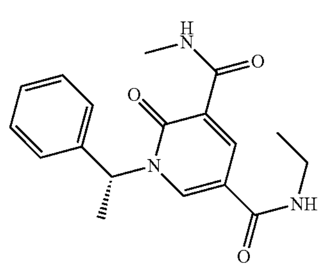 [SMILES: CCNC(=O)c1cc(C(=O)NC)c(=O)n([C@H](C)c2ccccc2)c1] | 20 | 55 | 328.0 | 0.83 |

All LCMS were conducted using 2 min Formic method.

Examples 17-18: Amide array of 1-(3-methoxybenzyl)-5-(methylcarbamoyl)-6-oxo-1,6-dihydropyridine-3-carboxylic acid To a stock solution of 1-(3-methoxybenzyl)-5-(methylcarbamoyl)-6-oxo-1,6-dihydropyridine-3-carboxylic acid (316 mg, 1 mmol) and HATU (380 mg) in DMF (5 mL) was added DIPEA (520 μL). The mixture was shaken and sonicated to aid dispersion. The mixture was aliquoted (0.55 mL) to a set of preweighed amines (as shown in table below). These were capped and shaken and left to stand at rt for 18 h. The samples were purified by MDAP (High pH). The solvent was dried under a stream of nitrogen to give the required products (as shown in table below).

Monomers

Examples 19-21: Amide array of 1-(3-(2-hydroxyethoxy)benzyl)-5-(methylcarbamoyl)-6-oxo-1,6-dihydropyridine-3-carboxylic acid To a stock solution of 1-(3-(2-hydroxyethoxy)benzyl)-5-(methylcarbannoyl)-6-oxo-1,6-dihydropyridine-3-carboxylic acid (337 mg, 0.97 mmol) and HATU (374 mg) in DMF (5.5 mL) was added DIPEA (550 μL). The solution was shaken and sonicated to aid dispersion and aliquoted (0.55 mL) to a set of preweighed amines (as shown in table below). Additional DIPEA (55 μL) was added to example 21 reaction mixture to compensate for the HCl salt of the amine monomer. The samples were injected as is and purified by MDAP (High pH). The solvent was dried under a stream of nitrogen to give the required products (as shown in table below).

| Ex No. | Reagent Name | Structure | MW | Reagent Mass (g) | Reagent Volume (mL) | mmol |
|---|---|---|---|---|---|---|
| 17 | 2-(1H-pyrazol-4-yl)ethanamine | 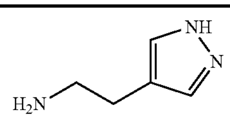 | 111.15 | 0.013 | — | 0.120 |
| 18 | ethanamine | 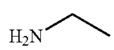 | 45.08 | 0.005 | — | 0.120 |

Examples

| Ex No. | Name | Structure | Mass (mg) | Yield (%) | [MH]+ | Rt (min) |
|---|---|---|---|---|---|---|
| 17 | $N^5$-(2-(1H-pyrazol-4-yl)ethyl)-1-(3-methoxybenzyl)-$N^3$-methyl-2-oxo-1,2-dihydropyridine-3,5-dicarboxamide | 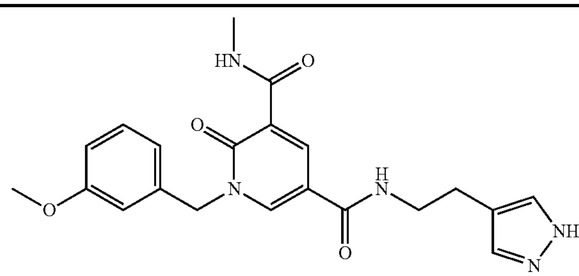 | 13.2 | 29.0 | 410 | 0.75 |
| 18 | $N^5$-ethyl-1-(3-methoxybenzyl)-$N^3$-methyl-2-oxo-1,2-dihydropyridine-3,5-dicarboxamide | 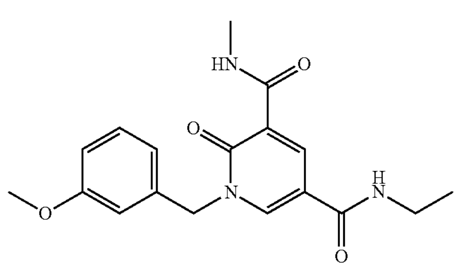 [SMILES: CCNC(=O)c1cc(C(=O)NC)c(=O)n(Cc2cccc(OC)c2)c1] | 22.1 | 57.9 | 344 | 0.82 |

All LCMS were conducted using 2 min Formic method.

Monomers

| Ex No. | Reagent Name | Structure | MW | Reagent Mass (g) | Reagent Volume (mL) | mmol |
|---|---|---|---|---|---|---|
| 19 | 2-(1H-imidazol-4-yl)ethanamine | 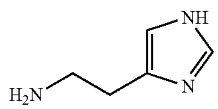 | 111.15 | 0.013 | — | 0.114 |
| 20 | ethanamine | 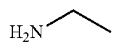 | 45.08 | 0.005 | — | 0.114 |
| 21 | 2-(1H-pyrazol-4-yl)ethanamine | 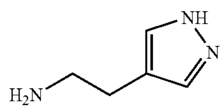 | 111.15 | 0.013 | — | 0.114 |

Examples

| Ex no. | Name | Structure | Mass (mg) | Yield (%) | [MH]+ | Rt (min) |
|---|---|---|---|---|---|---|
| 19 | $N^5$-(2-(1H-imidazol-4-yl)ethyl)-1-(3-(2-hydroxyethoxy)benzyl)-$N^3$-methyl-2-oxo-1,2-dihydropyridine-3,5-dicarboxamide | 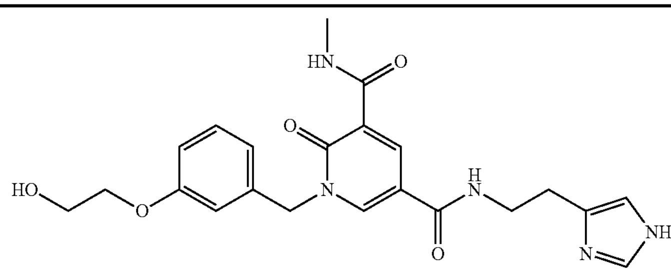 | 16.9 | 38.7 | 440 | 0.45 |
| 20 | $N^5$-Ethyl-1-(3-(2-hydroxyethoxy)benzyl)-$N^3$-methyl-2-oxo-1,2-dihydropyridine-3,5-dicarboxamide | 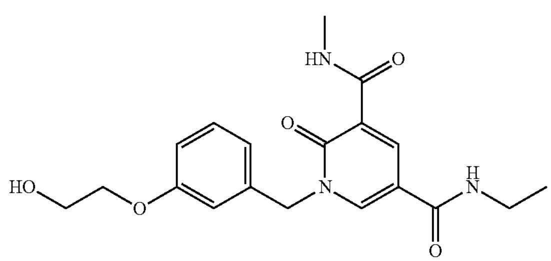 [SMILES: CCNC(=O)c1cc(C(=O)NC)c(=O)n(Cc2cccc(OCCO)c2)c1] | 15 | 40.4 | 374 | 0.67 |
| 21 | $N^5$-(2-(1H-pyrazol-4-yl)ethyl)-1-(3-(2-hydroxyethoxy)benzyl)-$N^3$-methyl-2-oxo-1,2-dihydropyridine-3,5-dicarboxamide | 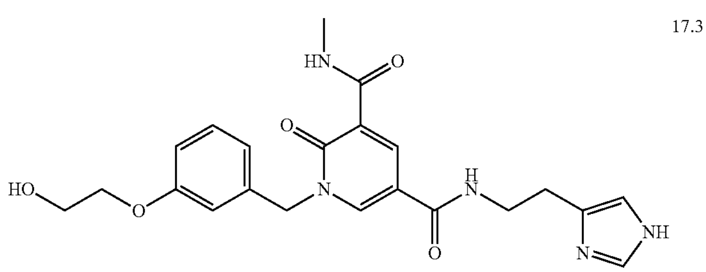 | 17.3 | 39.6 | 440 | 0.63 |

All LCMS were conducted using 2 min Formic method.

1H NMR for Example 20:

1H NMR (400 MHz, DMSO-d6) δ ppm 9.37 (br. q, J=4.5, 4.5, 4.5 Hz, 1H) 8.82 (d, J=2.7 Hz, 1H) 8.71 (d, J=2.7 Hz, 1H) 8.56 (br. t, J=5.3, 5.3 Hz, 1H) 7.26 (dd, J=9.0, 7.3 Hz, 1H) 6.84-6.92 (m, 3H) 5.26 (s, 2H) 4.81 (t, J=5.5 Hz, 1H) 3.95 (t, J=5.0 Hz, 2H) 3.69 (q, J=5.2 Hz, 2H) 3.21-3.29 (obs, 2H) 2.83 (d, J=4.9 Hz, 3H) 1.11 (t, J=7.2 Hz, 3H)

Examples 22-23: Amide array of 1-(2-fluoro-3-methylbenzyl)-5-(methylcarbamoyl)-6-oxo-1,6-dihydropyridine-3-carboxylic acid Monomers

| Ex No. | Reagent Name | Structure | MW | Reagent Mass (g) | Reagent Volume (mL) | mmol |
|---|---|---|---|---|---|---|
| 22 | Ethylamine (2M solution in THF) | H₂N— | 45.08 | — | 0.10 | 1.528 |
| 23 | 2-(1H-pyrazol-4-yl)ethanamine | H₂N— | 111.15 | 0.0133 | — | 0.120 |

To a stock solution of 1-(2-fluoro-3-methylbenzyl)-5-(methylcarbamoyl)-6-oxo-1,6-dihydropyridine-3-carboxylic acid (350 mg, 1.1 mmol) dissolved in DMF (5.5 mL) was added HATU (502 mg, 2.13 mmol) and DIPEA (570 µL, 3.3 mmol). The mixture was sonicated to aid dispersion and further DMF (5.5 mL) was added. An aliquot (1.0 mL) of this mixture was added to the appropriate amine (0.12 mmol) in DMF (0.3 mL) in a vial which was subsequently sealed, sonicated and left to stand at rt for 3 h. To the reaction containing the monomer amine used to prepare example 22 was added further HATU (0.046 g, 0.196 mmol), DIPEA (0.052 mL, 0.300 mmol) and ethylamine (2M solution in THF) (approx. 50 µL) and the mixture stirred at rt for 1 h. The samples were reduced to 1 mL, then injected as is and purified by MDAP (High pH). The solvent was removed using a plate dryer to give the required products.

Examples

| Ex No. | Name | Structure | Mass (mg) | Yield (%) | [MH]⁺ | Rt (min)* |
|---|---|---|---|---|---|---|
| 22 | N⁵-Ethyl-1-(2-fluoro-3-methylbenzyl)-N³-methyl-2-oxo-1,2-dihydropyridine-3,5-dicarboxamide | 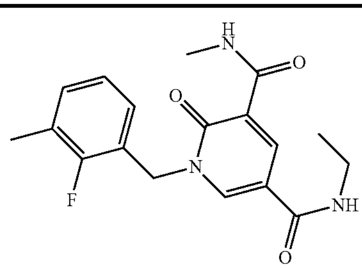 | 18.6 | 49 | 411 | 0.57 |
| 23 | N⁵-(2-(1H-Pyrazol-4-yl)ethyl)-1-(2-fluoro-3-methylbenzyl)-N³-methyl-2-oxo-1,2-dihydropyridine-3,5-dicarboxamide | 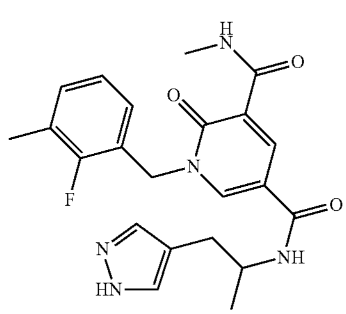 [SMILES: CNC(=O)c1cc(C(=O)NC(C)Cc2cn[nH]c2)cn(Cc2cccc(C)c2F)c1=O] | 17.0 | 37 | 412 | 0.82 |

Examples 24-26: Amide array of 1-((1H-Indol-4-yl)methyl)-5-(methylcarbamoyl)-6-oxo-1,6-dihydro-pyridine-3-carboxylic acid Monomers

| Ex No. | Reagent Name | Structure | MW | Reagent Mass (g) | Reagent Volume (mL) | mmol |
|---|---|---|---|---|---|---|
| 24 | 2-(1H-Imidazol-4-yl)ethanamine | 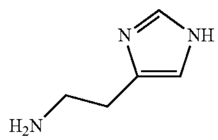 | 111.14 | 0.013 | — | 0.120 |
| 25 | Ethanamine | 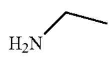 | 45.08 | — | 0.10 | 1.528 |
| 26 | 2-(1H-Pyrazol-4-yl)ethanamine | 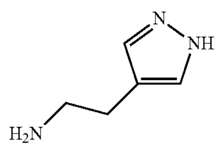 | 111.15 | 0.013 | — | 0.120 |

A stock solution of 1-((1H-indol-4-yl)methyl)-5-(methylcarbamoyl)-6-oxo-1,6-dihydropyridine-3-carboxylic acid (358 mg) was prepared in DMF (7.7 mL), along with HATU (502 mg), and DIPEA (0.57 mL), and was then capped and sonicated, before being aliquoted (0.7 mL) into vials containing the listed amine monomers (0.12 mmol). These were sealed and sonicated, then allowed to stand at rt for 18 h. (Note—for example 25 the solution was pipetted into an empty vial before ethanamine was added in excess (100 μL) to the vial due to its high volatility. The samples were then direcetly injected and purified by MDAP (High pH). The solvent was removed using a plate dryer to give the required products as indicated in the example table.

Examples

| Ex No. | Name | Structure | Mass (mg) | Yield (%) | [MH]+ | Rt (min)* |
|---|---|---|---|---|---|---|
| 24 | N⁵-(2-(1H-Imidazol-4-yl)ethyl)-1-((1H-indol-4-yl)methyl)-N³-methyl-2-oxo-1,2-dihydropyridine-3,5-dicarboxamide | 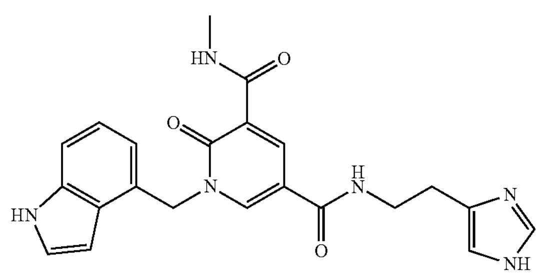 [SMILES: CNC(=O)c1cc(C(=O)NCCc2c[nH]cn2)cn(Cc2cccc3[nH]ccc23)c1=O] | 24 | 53 | 419 | 0.50 |
| 25 | 1-((1H-Indol-4-yl)methyl)-N⁵-ethyl-N³-methyl-2-oxo-1,2-dihydropyridine-3,5-dicarboxamide | 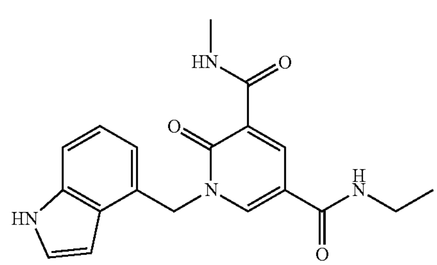 [SMILES: CCNC(=O)c1cc(C(=O)NC)c(=O)n(Cc2cccc3[nH]ccc23)c1] | 22 | 55 | 353 | 0.78 |

| Ex No. | Name | Structure | Mass (mg) | Yield (%) | [MH]+ | Rt (min)* |
|---|---|---|---|---|---|---|
| 26 | 1-((1H-Indol-4-yl)methyl)-N⁵-(2-(1H-pyrazol-4-yl)ethyl)-N³-methyl-2-oxo-1,2-dihydropyridine-3,5-dicarboxamide | 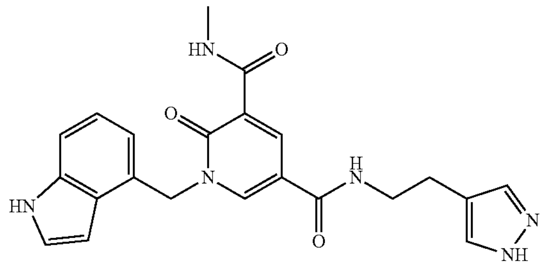 [SMILES: CNC(=O)c1cc(C(=O)NCCc2cn[nH]c2)cn(Cc2cccc3[nH]ccc23)c1=O] | 23 | 48 | 419 | 0.72 |

*All LCMS were conducted using 2 min Formic.

1H NMR for Example 25:
1H NMR (400 MHz, DMSO-d6) δ ppm 11.26 (br. s., 1H) 9.47 (br. q, J=4.3, 4.3, 4.3 Hz, 1H) 8.83 (d, J=2.7 Hz, 1H) 8.52-8.63 (m, 2H) 7.34-7.43 (m, 2H) 7.08 (t, J=7.7 Hz, 1H) 6.85 (d, J=7.1 Hz, 1H) 6.52 (d, J=1.0 Hz, 1H) 5.57 (s, 2H) 3.19-3.27 (m, 2H) 2.86 (d, J=4.6 Hz, 3H) 1.09 (t, J=7.2 Hz, 3H)

Examples 27-49

Examples 27-49 were prepared in an analogous manner to the previous examples.

| Ex No. | Name | Structure | [MH]+ | Rt (min)* |
|---|---|---|---|---|
| 27 | 1-Benzyl-N³,N⁵-dimethyl-2-oxo-1,2-dihydropyridine-3,5-dicarboxamide | 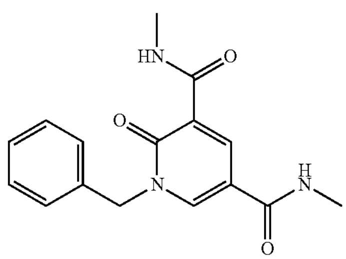 [SMILES: CNC(=O)c1cc(C(=O)NC)c(=O)n(Cc2ccccc2)c1] | 300.0 (formic) | 0.75 |
| 28 | 1-Benzyl-N⁵-isobutyl-N³-methyl-2-oxo-1,2-dihydropyridine-3,5-dicarboxamide | 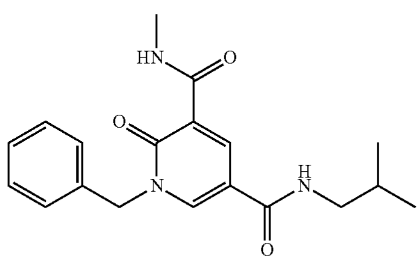 [SMILES: CNC(=O)c1cc(C(=O)NCC(C)C)cn(Cc2ccccc2)c1=O] | 342.1 (formic) | 0.98 |
| 29 | 1-Benzyl-N⁵-(2-methoxypropyl)-N³-methyl-2-oxo-1,2-dihydropyridine-3,5-dicarboxamide | 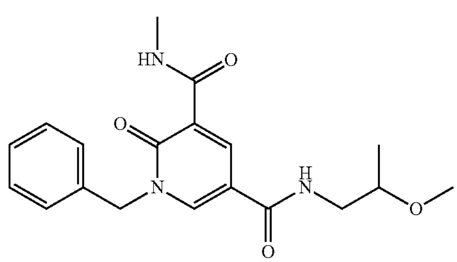 [SMILES: CNC(=O)c1cc(C(=O)NCC(C)OC)cn(Cc2ccccc2)c1=O] | 358.0 (formic) | 0.85 |

| Ex No. | Name | Structure | [MH]+ | Rt (min)* |
|---|---|---|---|---|
| 30 | 1-Benzyl-$N^5$-isopropyl-$N^3$-methyl-2-oxo-1,2-dihydropyridine-3,5-dicarboxamide | 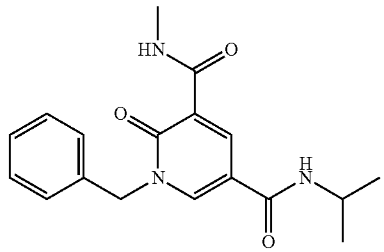 [SMILES: CNC(=O)c1cc(C(=O)NC(C)C)cn(Cc2ccccc2)c1=O] | 328.0 (formic) | 0.92 |
| 31 | 1-Benzyl-$N^5$-(2-hydroxypropyl)-$N^3$-methyl-2-oxo-1,2-dihydropyridine-3,5-dicarboxamide | 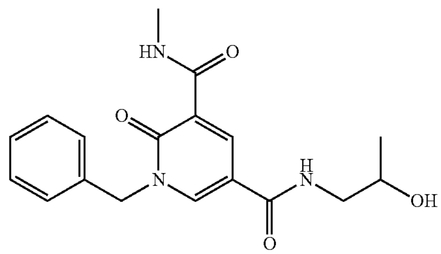 [SMILES: CNC(=O)c1cc(C(=O)NCC(C)O)cn(Cc2ccccc2)c1=O] | 344.0 (formic) | 0.73 |
| 32 | 1-Benzyl-$N^5$-(3-hydroxypropyl)-$N^3$-methyl-2-oxo-1,2-dihydropyridine-3,5-dicarboxamide | 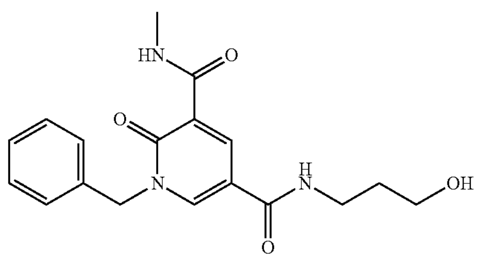 [SMILES: CNC(=O)c1cc(C(=O)NCCCO)cn(Cc2ccccc2)c1=O] | 344.1 (formic) | 0.72 |
| 33 | 1-Benzyl-$N^5$-(3-(dimethylamino)butyl)-$N^3$-methyl-2-oxo-1,2-dihydropyridine-3,5-dicarboxamide | 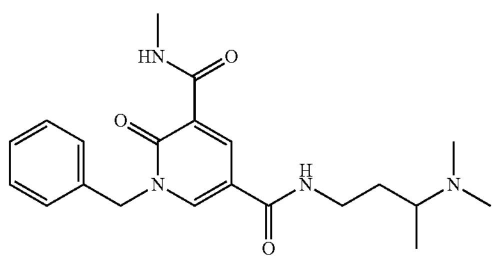 [SMILES: CNC(=O)c1cc(C(=O)NCCC(C)N(C)C)cn(Cc2ccccc2)c1=O] | 385.3 (formic) | 0.52 |
| 34 | 1-Benyl-$N^3$-methyl-2-oxo-$N^5$-(2-(pyridin-4-yl)ethyl)-1,2-dihydropyridine-3,5-dicarboxamide | 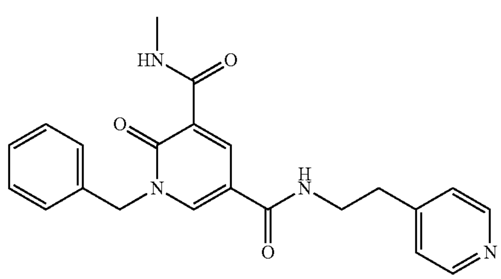 [SMILES: CNC(=O)c1cc(C(=O)NCCc2ccncc2)cn(Cc2ccccc2)c1=O] | 391.3 (formic) | 0.53 |
| 35 | 1-Benzyl-$N^3$-methyl-$N^5$-(3-(methylamino)-3-oxopropyl)-2-oxo-1,2-dihydropyridine-3,5-dicarboxamide | 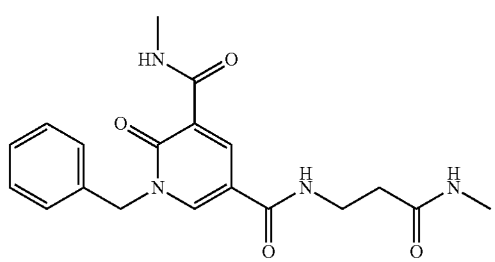 [SMILES: CNC(=O)CCNC(=O)c1cc(C(=O)NC)c(=O)n(Cc2ccccc2)c1] | 371.3 (formic) | 0.71 |

-continued

| Ex No. | Name | Structure | [MH]+ | Rt (min)* |
|---|---|---|---|---|
| 36 | 1-Benzyl-$N^5$-(3-cyanopropyl)-$N^3$-methyl-2-oxo-1,2-dihydropyridine-3,5-dicarboxamide | 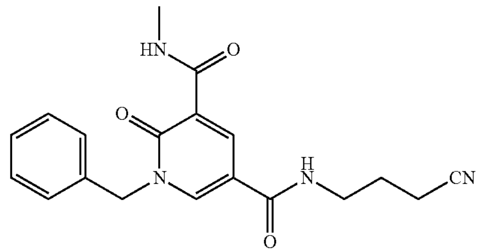 [SMILES: CNC(=O)c1cc(C(=O)NCCCC#N)cn(Cc2ccccc2)c1=O] | 353.3 (formic) | 0.80 |
| 37 | 1-Benzyl-$N^5$-(2-cyanoethyl)-$N^3$-methyl-2-oxo-1,2-dihydropyridine-3,5-dicarboxamide | 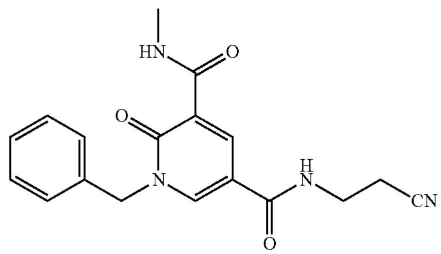 [SMILES: CNC(=O)c1cc(C(=O)NCCC#N)cn(Cc2ccccc2)c1=O] | 339.3 (formic) | 0.78 |
| 38 | $N^5$-(3-Aminopropyl)-1-benzyl-$N^3$-methyl-2-oxo-1,2-dihydropyridine-3,5-dicarboxamide | 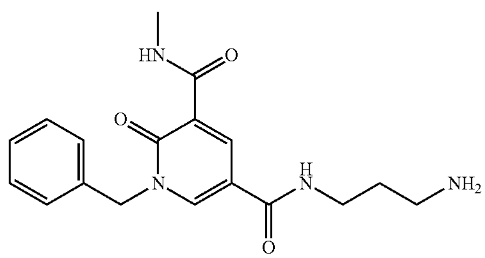 [SMILES: CNC(=O)c1cc(C(=O)NCCCN)cn(Cc2ccccc2)c1=O] | 343.1 (formic) | 0.50 |
| 39 | 1-Benzyl-$N^5$-(3-hydroxybutyl)-$N^3$-methyl-2-oxo-1,2-dihydropyridine-3,5-dicarboxamide | 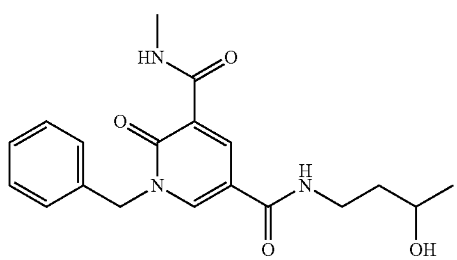 [SMILES: CNC(=O)c1cc(C(=O)NCCC(C)O)cn(Cc2ccccc2)c1=O] | 358.3 (High pH) | 0.79 |
| 40 | 1-Benzyl-$N^3$-methyl-2-oxo-$N^5$-(2-(pyridin-3-yl)ethyl)-1,2-dihydropyridine-3,5-dicarboxamide | 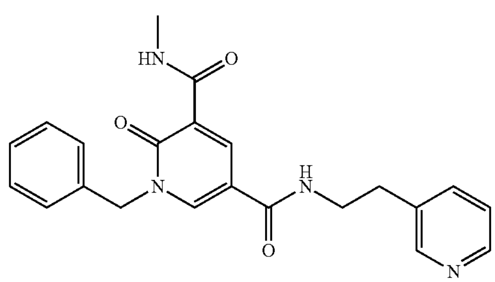 [SMILES: CNC(=O)c1cc(C(=O)NCCc2cccnc2)cn(Cc2ccccc2)c1=O] | 391.3 (formic) | 0.54 |
| 41 | 1-Benzyl-$N^5$-(2-methoxyethyl)-$N^3$-methyl-2-oxo-1,2-dihydropyridine-3,5-dicarboxamide | 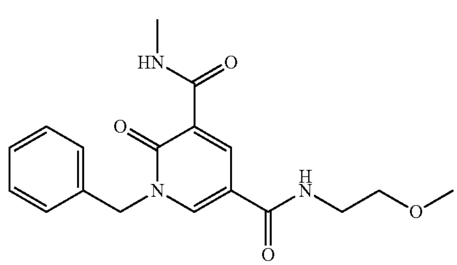 [SMILES: CNC(=O)c1cc(C(=O)NCCOC)cn(Cc2ccccc2)c1=O] | 344.3 (formic) | 0.78 |

-continued

| Ex No. | Name | Structure | [MH]+ | Rt (min)* |
|---|---|---|---|---|
| 42 | 1-Benzyl-$N^5$-(3-methoxypropyl)-$N^3$-methyl-2-oxo-1,2-dihydropyridine-3,5-dicarboxamide | 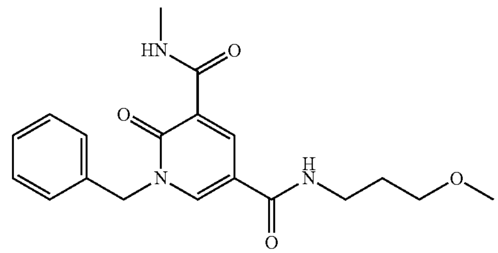 [SMILES: CNC(=O)c1cc(C(=O)NCCCOC)cn(Cc2ccccc2)c1=O] | 358.3 (formic) | 0.82 |
| 43 | 1-(3-Cyanobenzyl)-$N^3,N^5$-dimethyl-2-oxo-1,2-dihydropyridine-3,5-dicarboxamide | 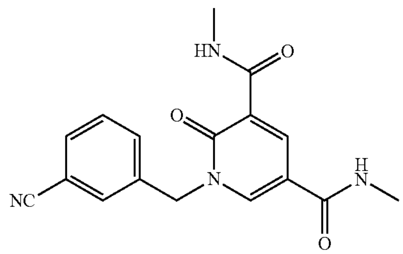 [SMILES: CNC(=O)c1cc(C(=O)NC)c(=O)n(Cc2cccc(C#N)c2)c1] | 325.2 (formic) | 0.70 |
| 44 | 4-(1-Benzyl-5-(methylcarbamoyl)-6-oxo-1,6-dihydropyridine-3-carboxamido)butanoic acid | 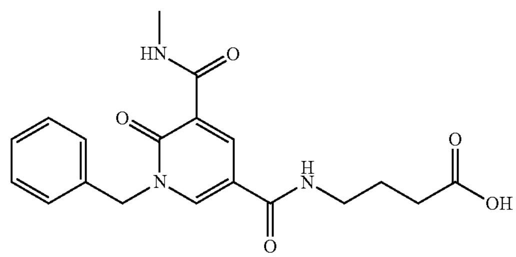 [SMILES: CNC(=O)c1cc(C(=O)NCCCC(=O)O)cn(Cc2ccccc2)c1=O] | 372.3 (formic) | 0.76 |
| 45 | 1-Benzyl-$N^3$-methyl-$N^5$-(2-(methylsulfonyl)ethyl)-2-oxo-1,2-dihydropyridine-3,5-dicarboxamide | 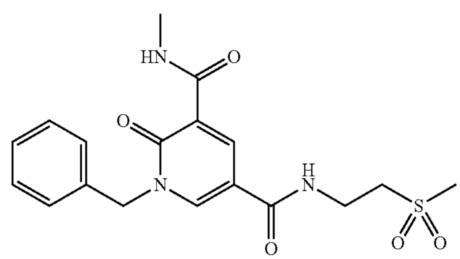 [SMILES: CNC(=O)c1cc(C(=O)NCCS(C)(=O)=O)cn(Cc2ccccc2)c1=O] | 392.3 (formic) | 0.74 |
| 46 | 1-Benzyl-$N^5$-(2-hydroxyethyl)-$N^3$-methyl-2-oxo-1,2-dihydropyridine-3,5-dicarboxamide | 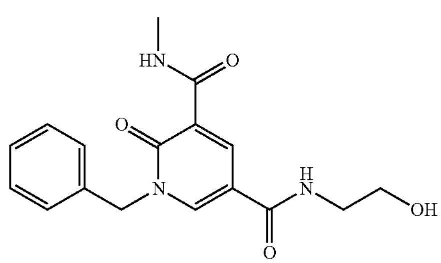 | 330.1 (formic) | 0.69 |
| 47 | 1-Benzyl-$N^5$-(3-(dimethylamino)propyl)-$N^3$-methyl-2-oxo-1,2-dihydropyridine-3,5-dicarboxamide | 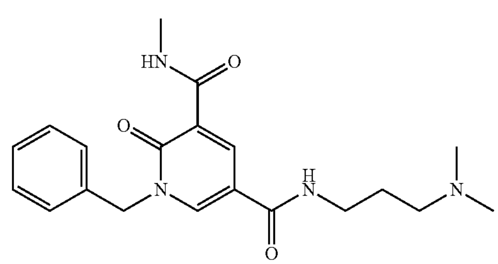 [SMILES: CNC(=O)c1cc(C(=O)NCCCN(C)C)cn(Cc2ccccc2)c1=O] | 371.2 (formic) | 0.51 |

-continued

| Ex No. | Name | Structure | [MH]+ | Rt (min)* |
|---|---|---|---|---|
| 48 | 1-Benzyl-$N^3$-methyl-$N^5$-(3-(methylsulfonyl)propyl)-2-oxo-1,2-dihydropyridine-3,5-dicarboxamide | 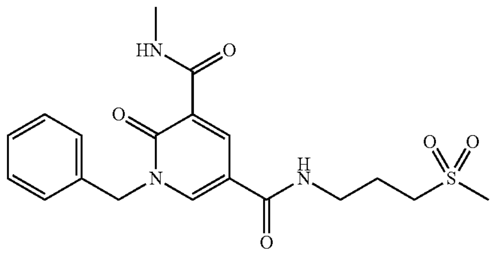 [SMILES: CNC(=O)c1cc(C(=O)NCCCS(C)(=O)=O)cn(Cc2ccccc2)c1=O] | 406.3 (formic) | 0.75 |
| 49 | $N^5$-(2-(1H-Imidazol-4-yl)ethyl)-1-(2-fluoro-3-methylbenzyl)-N3-methyl-2-oxo-1,2-dihydropyridine-3,5-dicarboxamide | 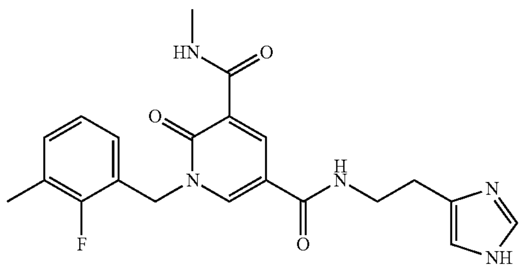 [SMILES: CNC(=O)c1cc(C(=O)NCCc2c[nH]cn2)cn(Cc2cccc(C)c2F)c1=O] | 411.9 (formic) | 0.57 |

Examples 50-58: Amide array of 1-(3-methoxybenzyl)-5-(methylcarbamoyl)-6-oxo-1,6-dihydropyridine-3-carboxylic acid A stock solution of 1-benzyl-5-(methylcarbannoyl)-6-oxo-1,6-dihydropyridine-3-carboxylic acid (0.029 g, 0.1 mmol)×12=344 mg and HATU (502 mg), dissolved in DMF (6 mL) was prepared and DIPEA (624 uL) was added. The stock solution was aliquoted (0.5 mL) to a set of preweighed amine monomers×12 (0.120 mmol, see table) in matrix vials at rt. For examples 53, 54, 56 and 57, additional DIPEA (25 uL) was added, due to the monomers being HCl salts. The vials were capped and shaken to aid dispersement. The reaction mixtures were stood at rt for 18 h. All the reaction mixtures were then injected as is and purified by MDAP (High pH). The solvent was dried under a stream of nitrogen in the plate blowdown apparatus to give the required examples as shown in the table.

Monomers

| Ex No. | Reagent Name | Structure | MW | Reagent Mass (g) | mmol |
|---|---|---|---|---|---|
| 50 | 2-(1H-Pyrazol-5-yl)ethanamine | 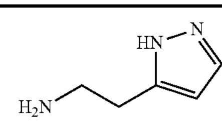 | 111.15 | 0.013 | 0.120 |
| 51 | 1-Methyl-1H-pyrazol-3-amine | 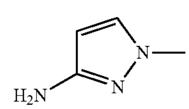 | 97.118 | 0.012 | 0.120 |
| 52 | 2-(1-Methyl-1H-pyrazol-4-yl)ethanamine | 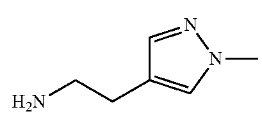 | 125.172 | 0.015 | 0.120 |
| 53 | 1-Methyl-1H-pyrazol-4-amine | 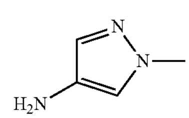 | 97.118 | 0.012 | 0.120 |
| 54 | 2-(4-Methyl-4H-1,2,4-triazol-3-yl)ethanamine | 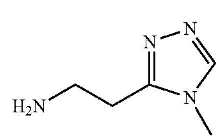 | 126.160 | 0.015 | 0.120 |

-continued

| Ex No. | Reagent Name | Structure | MW | Reagent Mass (g) | mmol |
|---|---|---|---|---|---|
| 55 | 2-(4-Methylthiazol-5-yl)ethanamine | 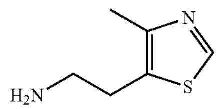 | 142.222 | 0.017 | 0.120 |
| 56 | 2-(thiazol-4-yl)ethanamine | 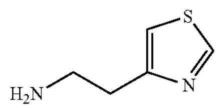 | 128.195 | 0.015 | 0.120 |
| 57 | 2-(Isoxazol-4-yl)ethanamine | 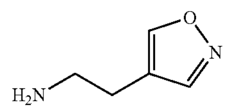 | 112.130 | 0.013 | 0.120 |
| 58 | Pyridazin-4-amine | 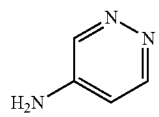 | 95.103 | 0.011 | 0.120 |

Examples

| Ex no. | Name | Structure | Mass (mg) | Yield (%) | [MH]+ | Rt (min) |
|---|---|---|---|---|---|---|
| 50 | $N^5$-(2-(1H-Pyrazol-5-yl)ethyl)-1-benzyl-$N^3$-methyl-2-oxo-1,2-dihydropyridine-3,5-dicarboxamide | 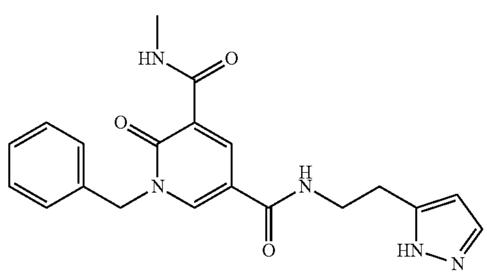 [SMILES: CNC(=O)c1cc(C(=O)NCCc2ccn[nH]2)cn(Cc2ccccc2)c1=O] | 24.3 | 58 | 380 | 0.75 |
| 51 | 1-Benzyl-$N^3$-methyl-$N^5$-(1-methyl-1H-pyrazol-3-yl)-2-oxo-1,2-dihydropyridine-3,5-dicarboxamide | 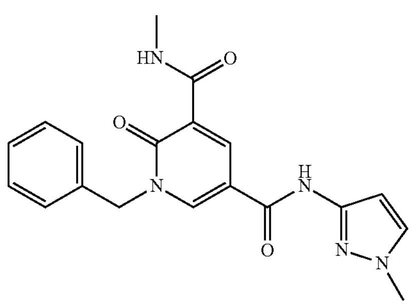 [SMILES: CNC(=O)c1cc(C(=O)Nc2ccn(C)n2)cn(Cc2ccccc2)c1=O] | 25.1 | 62 | 366 | 0.82 |
| 52 | 1-Benzyl-$N^3$-methyl-$N^5$-(2-(1-methyl-1H-pyrazol-4-yl)ethyl)-2-oxo-1,2-dihydropyridine-3,5-dicarboxamide | 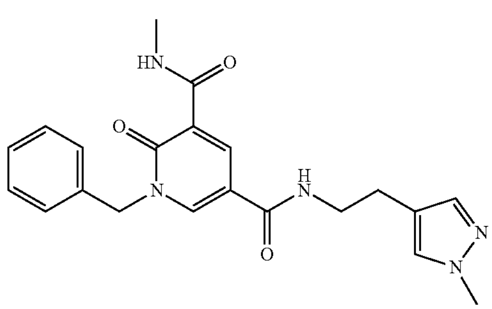 [SMILES: CNC(=O)c1cc(C(=O)NCCc2cnn(C)c2)cn(Cc2ccccc2)c1=O] | 22.7 | 52 | 394 | 0.79 |

| Ex no. | Name | Structure | Mass (mg) | Yield (%) | [MH]+ | Rt (min) |
|---|---|---|---|---|---|---|
| 53 | 1-Benzyl-$N^3$-methyl-$N^5$-(1-methyl-1H-pyrazol-4-yl)-2-oxo-1,2-dihydropyridine-3,5-dicarboxamide | 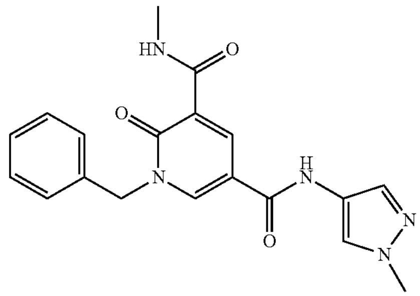 [SMILES: CNC(=O)c1cc(C(=O)Nc2cnn(C)c2)cn(Cc2ccccc2)c1=O] | 27.4 | 68 | 366 | 0.80 |
| 54 | 1-Benzyl-$N^3$-methyl-$N^5$-(2-(4-methyl-4H-1,2,4-triazol-3-yl)ethyl)-2-oxo-1,2-dihydropyridine-3,5-dicarboxamide | 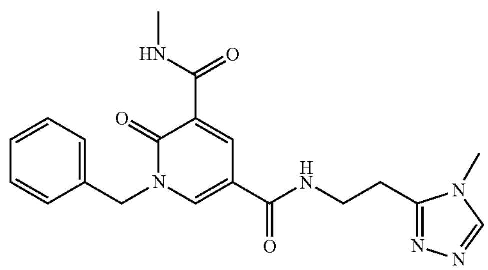 [SMILES: CNC(=O)c1cc(C(=O)NCCc2nncn2C)cn(Cc2ccccc2)c1=O] | 15.2 | 35 | 395 | 0.63 |
| 55 | 1-Benzyl-$N^3$-methyl-$N^5$-(2-(4-methylthiazol-5-yl)ethyl)-2-oxo-1,2-dihydropyridine-3,5-dicarboxamide | 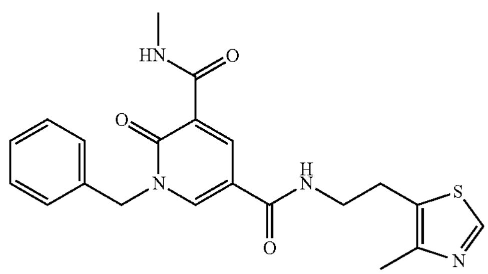 [SMILES: CNC(=O)c1cc(C(=O)NCCc2scnc2C)cn(Cc2ccccc2)c1=O] | 20.9 | 46 | 411 | 0.80 |
| 56 | 1-Benzyl-$N^3$-methyl-2-oxo-$N^5$-(2-(thiazol-4-yl)ethyl)-1,2-dihydropyridine-3,5-dicarboxamide | 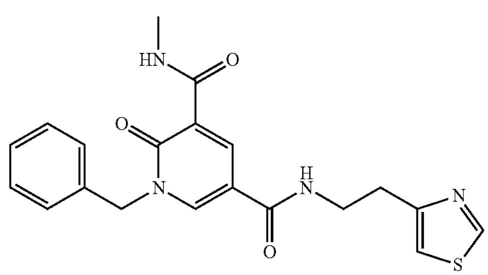 [SMILES: CNC(=O)c1cc(C(=O)NCCc2cscn2)cn(Cc2ccccc2)c1=O] | 21.5 | 49 | 397 | 0.82 |
| 57 | 1-Benzyl-$N^5$-(2-(isoxazol-4-yl)ethyl)-$N^3$-methyl-2-oxo-1,2-dihydropyridine-3,5-dicarboxamide | 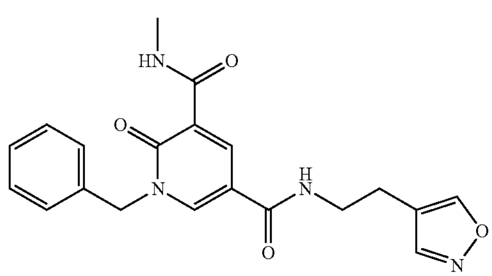 [SMILES: CNC(=O)c1cc(C(=O)NCCc2cnoc2)cn(Cc2ccccc2)c1=O] | 20.1 | 48 | 381 | 0.83 |

| Ex no. | Name | Structure | Mass (mg) | Yield (%) | [MH]+ | Rt (min) |
|---|---|---|---|---|---|---|
| 58 | 1-Benzyl-$N^3$-methyl-2-oxo-$N^5$-(pyridazin-4-yl)-1,2-dihydropyridine-3,5-dicarboxamide | 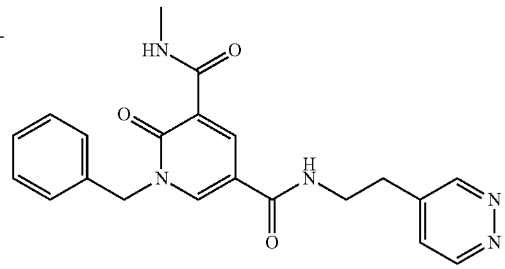 | 27.3 | 68 | 364 | 0.73 |

All LC/MS were conducted using 2 min Formic method.

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

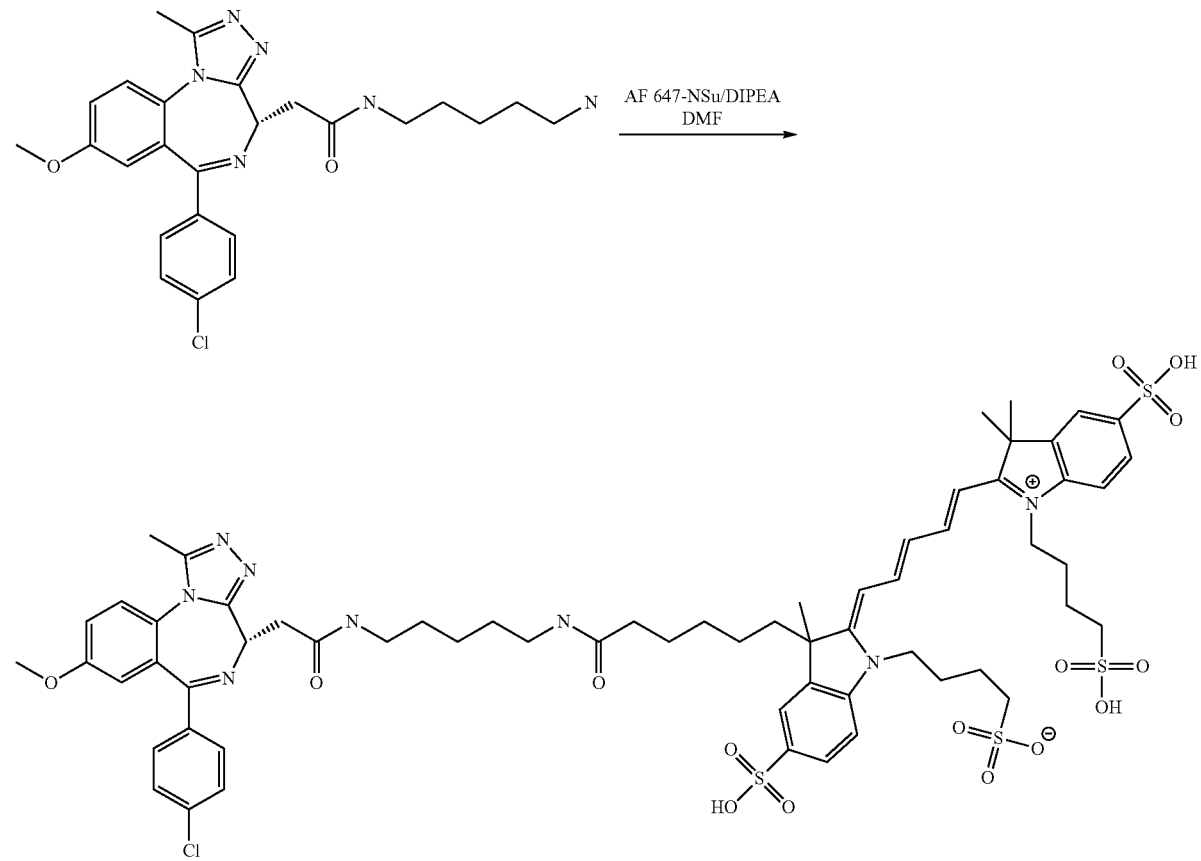 [SMILES: COc1ccc2c(c1)C(c1ccc(Cl)cc1)=N[C@@H](CC(=O)NCCCCCN)c1nnc(C)n1-2 ; COc1ccc2c(c1)C(c1ccc(Cl)cc1)=N[C@@H](CC(=O)NCCCCCNC(=O)CCCCCC1(C)/C(=C/C=C/C=C/C3=[N+](CCCCS(=O)(=O)O)c4ccc(S(=O)(=O)O)cc4C3(C)C)N(CCCCS(=O)(=O)[O-])c3ccc(S(=O)(=O)O)cc31)c1nnc(C)n1-2]

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 µmol) in DMF (40 µl) was added a solution of AlexaFluor647-ONSu (2.16 mg, 1.966 µmol) also in DMF (100 µl). The mixture was basified with DIPEA (1 µl, 5.73 µmol) and agitated overnight on a vortex mixer.

The reaction mixture was evaporated to dryness. The solid was dissolved in acetonitrile/water/acetic acid (5/4/1, <1 ml) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm): 5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transfered with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: $[M+H]^+$ (obs): 661.8/- corresponding with M-29. This equates to $[(M+2H)/2]^+$ for a calculated mass of 1320.984 which is M-29. This is a standard occurence with the Alexa Fluor 647 dye and represents a theoretical loss of two methylene groups under the conditions of the mass spectrometer.

Assay Principle:

In order to generate a TR-FRET signal, donor fluorophore is excited by a laser at $\lambda 337$ nm, which subsequently leads to emission at $\lambda 618$ nm. If the acceptor fluorophore is in close proximity then energy transfer can occur, which leads to emission of Alexa Fluor® 647 at $\lambda 665$ nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at $\lambda 665$ nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly greatly reduced in comparison to the non mutated, wild type tandem BET proteins (>1000 fold reduction in Kd). The affinities of the single mutated bromdomain tandem proteins for Reference Compound X were equi-potent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein production: Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µl/ml protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at –80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant TR-FRET Competition Assays:

All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at $\lambda 337$ nm and subsequently, after a delay of 50 µsecs, measuring emission of the donor and acceptor fluorophores at $\lambda 615$ nm and $\lambda 665$ nm, respectively. In order to control these assays, 16 replicates each of uninhibited (DMSO vehicle) and inhibited ($10*IC_{50}$ concentrations of Example 11 of WO 2011/054846A1) TR-FRET assays were included on every microtitre plate.

cA four parameter curve fit of the following form was then applied:

$$y=a+((b-a)/(1+(10\char`\^x/10\char`\^c)\char`\^d)$$

Where 'a' is the minimum, 'b' is the Hill slope, 'c' is the $pIC_{50}$ and 'd' is the maximum.

All compounds (Examples 1-58) were each tested in the BRD4 BD1 and the BRD4 BD2 TR-FRET assays described above.

All compounds were found to have a $pIC_{50} \geq 5.0$ in at least one assay.

Examples 29, 31 and 43 were found to have a $pIC_{50} \geq 4.0$ and <6.0 in the BRD4 BD2 assay.

Examples 1-10, 14, 16-23, 27, 28, 30, 32-42, 44-52 and 5458 were found to have a $pIC_{50} \geq 6.0$ and <7.0 in the BRD4 BD2 assay.

Examples 11-13, 15, 24-26 and 53 were found to have a $pIC_{50} \geq 7.0$ in the BRD4 BD2 assay.

Specific data for a selection of Examples is shown in the table below:

| Ex. No. | BRD4 BD2 IC$_{50}$ (average value) | N (total number of values recorded) |
|---|---|---|
| 2 | 6.9 | 3 |
| 11 | 7.2 | 3 |
| 13 | 7 | 4 |
| 20 | 6.6 | 2 |
| 25 | 7.6 | 4 |

Those of skill in the art will recognise that in vitro binding assays and cell-based assays for functional activity are subject to experimental variability. Accordingly, it is to be understood that the pIC$_{50}$ values given above are exemplary only.

Calculation of Selectivity for BRD4 BD2 over BRD4 BD1

Selectivity for BRD4 BD2 over BRD4 BD1 was calculated as follows:

Selectivity=BRD4BD2pIC$_{50}$−BRD4BD1pIC$_{50}$ pIC$_{50}$ values are expressed as log$_{10}$ units.

With the exception of Example 44 all tested compounds were found to have selectivity for BRD4 BD2 over BRD4 BD1 of ≥1 log unit in at least one of the TR-FRET assays described above, hence are at least 10 fold selective for BRD4 BD2 over BRD4 BD1.

Examples 1-26 and 50-56 were found to have selectivity for BRD4 BD2 over BRD4 BD1 of ≥2 log unit in at least one of the TR-FRET assays described above, hence are at least 100 fold selective for BRD4 BD2 over BRD4 BD1.

The invention claimed is:

1. A compound of Formula (I) or a pharmaceutically acceptable salt thereof:

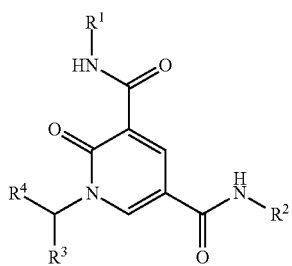

(I)

wherein

R$^1$ is C$_{1-3}$ alkyl or cyclopropyl;

R$_2$ is —CH$_3$, C$_{2-6}$ alkyl, —C$_{2-6}$ alkylOR$^5$, —C$_{2-6}$ alkylNR$^5$R$^6$, —(CH$_2$)$_m$SO$_2$C$_{1-3}$ alkyl, —(CH$_2$)$_m$C(O) NR$^5$R$^6$, —(CH$_2$)$_m$CN, —(CH$_2$)$_m$CO$_2$R$^5$, —(CH$_2$)$_m$ NHCO$_2$C(CH$_3$)$_3$, or —(CH$_2$)$_n$C$_{5-6}$ heteroaryl, wherein said C$_{2-6}$ alkyl is optionally substituted by one, two, three, four, or five times by fluoro; or said C$_{5-6}$ heteroaryl is optionally substituted by one or two substituents independently selected from halo, C$_{1-4}$ alkyl, C$_{3-4}$ cycloalkyl, and —OR$^5$;

R$^3$ is phenyl, C$_{5-6}$ heteroaryl, C$_{9-11}$heteroaryl, or —(CH$_2$)$_q$-phenyl, wherein said phenyl is optionally substituted one, two, or three times by R$^9$, said C$_{5-6}$ heteroaryl is optionally substituted by C$_{1-3}$ alkyl, C$_{3-4}$ cycloalkyl, C$_{1-3}$ alkoxy, or halo; or said C$_{9-11}$heteroaryl is optionally substituted one, two, or three times independently selected from —C$_{1-3}$ alkylR$^{10}$, —OCH$_3$, —OCHF$_2$, —OCF$_3$, —OC$_{2-3}$ alkylR$^{10}$, halo, oxo, and —CN;

R$^4$ is —H, C$_{1-4}$ alkyl, cyclopropyl, —CH$_2$OR$^{11}$, or —CH$_2$CH$_2$OR$^{11}$;

R$^5$ and R$^6$ are each independently selected from —H, C$_{1-3}$ alkyl, and C$_{2-4}$ alkylOC$_{0-3}$ alkyl;

each R$^9$ is independently selected from —NR$^{12}$R$^{13}$, —CN, —CH$_2$CN, —CO$_2$R$^{11}$, —C(O)C$_{1-3}$ alkyl, —OH, —OCHF$_2$, —OCF$_3$, —O—C$_{2-6}$ alkylR$^{10}$, —OCH$_3$, —OCH$_2$CH$_2$NR$^{12}$R$^{13}$, —C$_{1-6}$ alkylR$^{10}$, —OC$_{4-7}$ heterocyclyl, —OCH$_2$C$_{4-7}$ heterocyclyl, —CH$_2$C$_{4-7}$ heterocyclyl, —CH$_2$CH$_2$C$_{4-7}$ heterocyclyl, —NHC(O)R$^{11}$, —SO$_2$R$^{11}$, and —SOR$^{11}$;

R$^{10}$ is —H, —OR$^{11}$, or —NR$^{12}$R$^{13}$;

R$^{11}$ is —H or C$_{1-3}$ alkyl;

R$^{12}$ and R$^{13}$ are each independently selected from —H and C$_{1-3}$ alkyl; or R$^{12}$ and R$^{13}$ may join together with nitrogen to which they are attached to form a C$_{4-7}$heterocyclyl optionally containing a further heteroatom selected from nitrogen, oxygen, and sulphur and optionally substituted by one or two substituents independently selected from C$_{1-3}$ alkyl, —OH, and fluoro;

m is selected from 0, 1, 2, 3, and 4;

n is selected from 2, 3, and 4; and q is selected from 1 and 2.

2. The compound or pharmaceutically acceptable salt thereof according to claim 1, wherein R$^1$ is methyl.

3. The compound or pharmaceutically acceptable salt thereof according to claim 1, wherein R$^2$ is selected from methyl, ethyl, propyl, iso-propyl, butyl, —CH$_2$CH$_2$CH (CH$_3$)$_2$, —CH$_2$CH(CH$_3$)$_2$, —CH$_2$CH$_2$OR$^5$, —CH$_2$CH$_2$CH$_2$OR$^5$, —CH$_2$CH(CH$_3$)OR$^5$, —CH$_2$CH$_2$CH (CH$_3$)OR$^5$, —CH$_2$CH$_2$CH(CH$_3$)NR$^5$R$^6$, —CH$_2$CH$_2$CH$_2$NR$^5$R$^6$, —(CH$_2$)$_m$SO$_2$CH$_3$, —(CH$_2$)$_m$C(O) NHCH$_3$, —(CH$_2$)$_m$CN, —(CH$_2$)$_m$CO$_2$R$^5$, —(CH$_2$)$_m$CF$_3$, and —(CH$_2$)$_m$NHCO$_2$C(CH$_3$)$_3$.

4. The compound or pharmaceutically acceptable salt thereof according to claim 1, wherein R$^2$ is —(CH$_2$)$_n$C$_{5-10}$ heteroaryl, wherein said C$_{5-10}$heteroaryl is imidazolyl, pyridinyl, or pyrazolyl.

5. The compound or pharmaceutically acceptable salt thereof according to claim 1, wherein R$^3$ is phenyl, wherein said phenyl is optionally substituted by one or two times by R$^9$, wherein each R$^9$ is selected from fluoro, —CN, —OCH$_3$, —OC$_{1-6}$ alkylR$^{10}$, and —C$_{1-6}$ alkylR$^{10}$.

6. A compound or pharmaceutically acceptable salt thereof according to claim 5, wherein R$^3$ is selected from:

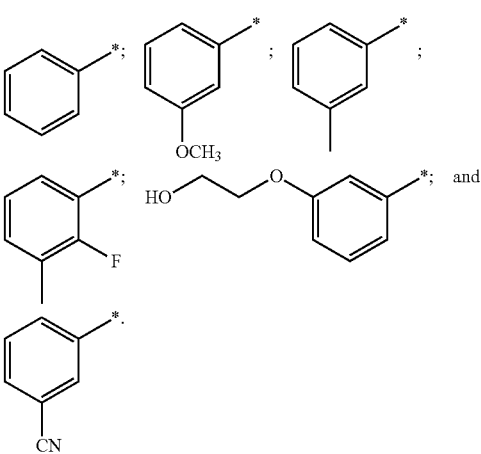

7. The compound or pharmaceutically acceptable salt thereof according to claim 1, wherein $R^3$ is unsubstituted phenyl.

8. The compound or pharmaceutically acceptable salt thereof according to claim 1, wherein $R^3$ is unsubstituted indolyl.

9. The compound or pharmaceutically acceptable salt thereof according to claim 1, wherein $R^4$ is —H or methyl.

10. The compound or pharmaceutically acceptable salt thereof according to claim 1, wherein $R^{10}$ is —$OR^{11}$.

11. The compound or pharmaceutically acceptable salt thereof according to claim 1, wherein $R^{11}$ is —H.

12. The compound or pharmaceutically acceptable salt thereof according to claim 1, wherein n is 2 or 3.

13. The compound or pharmaceutically acceptable salt thereof according to claim 1, wherein m is 2 or 3.

14. The compound according to claim 1 which is:
1-benzyl-N5-ethyl-N3-methyl-2-oxo-1,2-dihydropyridine-3,5-dicarboxamide;
1-benzyl-N3-methyl-2-oxo-N5-propyl-1,2-dihydropyridine-3,5-dicarboxamide;
1-benzyl-N5-butyl-N3-methyl-2-oxo-1,2-dihydropyridine-3,5-dicarboxamide;
1-benzyl-N5-isopentyl-N3-methyl-2-oxo-1,2-dihydropyridine-3,5-dicarboxamide;
1-benzyl-N3-methyl-N5-(4-(methylamino)-4-oxobutyl)-2-oxo-1,2-dihydropyridine-3,5-dicarboxamide;
tert-butyl (3-(1-benzyl-5-(methylcarbamoyl)-6-oxo-1,6-dihydropyridine-3-carboxamido)propyl)carbamate;
1-benzyl-N3-methyl-2-oxo-N5-(3,3,3-trifluoropropyl)-1,2-dihydropyridine-3,5-dicarboxamide;
N5-(2-(1H-imidazol-5-yl)ethyl)-1-benzyl-N3-methyl-2-oxo-1,2-dihydropyridine-3,5-dicarboxamide;
methyl 4-(1-benzyl-5-(methylcarbamoyl)-6-oxo-1,6-dihydropyridine-3-carboxamido)butanoate;
1-benzyl-N3-methyl-2-oxo-N5-(2-(pyridin-2-yl)ethyl)-1,2-dihydropyridine-3,5-dicarboxamide;
N5-(3-(1H-imidazol-2-yl)propyl)-1-benzyl-N3-methyl-2-oxo-1,2-dihydropyridine-3,5-dicarboxamide;
N5-(2-(1H-pyrazol-4-yl)ethyl)-1-benzyl-N3-methyl-2-oxo-1,2-dihydropyridine-3,5-dicarboxamide;
N5-(2-(1H-pyrazol-4-yl)ethyl)-N3-methyl-1-(3-methylbenzyl)-2-oxo-1,2-dihydropyridine-3,5-dicarboxamide;
N5-ethyl-N3-methyl-1-(3-methylbenzyl)-2-oxo-1,2-dihydropyridine-3,5-dicarboxamide;
(R)—N5-(2-(1H-pyrazol-4-yl)ethyl)-N3-methyl-2-oxo-1-(1-phenylethyl)-1,2-dihydropyridine-3,5-dicarboxamide;
(R)—N5-ethyl-N3-methyl-2-oxo-1-(1-phenylethyl)-1,2-dihydropyridine-3,5-dicarboxamide;
N5-(2-(1H-pyrazol-4-yl)ethyl)-1-(3-methoxybenzyl)-N3-methyl-2-oxo-1,2-dihydropyridine-3,5-dicarboxamide;
N5-ethyl-1-(3-methoxybenzyl)-N3-methyl-2-oxo-1,2-dihydropyridine-3,5-dicarboxamide;
N5-(2-(1H-imidazol-4-yl)ethyl)-1-(3-(2-hydroxyethoxy)benzyl)-N3-methyl-2-oxo-1,2-dihydropyridine-3,5-dicarboxamide;
N5-ethyl-1-(3-(2-hydroxyethoxy)benzyl)-N3-methyl-2-oxo-1,2-dihydropyridine-3,5-dicarboxamide;
N5-(2-(1H-pyrazol-4-yl)ethyl)-1-(3-(2-hydroxyethoxy)benzyl)-N3-methyl-2-oxo-1,2-dihydropyridine-3,5-dicarboxamide;
N5-ethyl-1-(2-fluoro-3-methylbenzyl)-N3-methyl-2-oxo-1,2-dihydropyridine-3,5-dicarboxamide;
N5-(2-(1H-pyrazol-4-yl)ethyl)-1-(2-fluoro-3-methylbenzyl)-N3-methyl-2-oxo-1,2-dihydropyridine-3,5-dicarboxamide;
N5-(2-(1H-imidazol-4-yl)ethyl)-1-((1H-indol-4-yl)methyl)-N3-methyl-2-oxo-1,2-dihydropyridine-3,5-dicarboxamide;
1-((1H-indol-4-yl)methyl)-N5-ethyl-N3-methyl-2-oxo-1,2-dihydropyridine-3,5-dicarboxamide;
1-((1H-indol-4-yl)methyl)-N5-(2-(1H-pyrazol-4-yl)ethyl)-N3-methyl-2-oxo-1,2-dihydropyridine-3,5-dicarboxamide;
1-benzyl-N3,N5-dimethyl-2-oxo-1,2-dihydropyridine-3,5-dicarboxamide;
1-benzyl-N5-isobutyl-N3-methyl-2-oxo-1,2-dihydropyridine-3,5-dicarboxamide;
1-benzyl-N5-(2-methoxypropyl)-N3-methyl-2-oxo-1,2-dihydropyridine-3,5-dicarboxamide;
1-benzyl-N5-isopropyl-N3-methyl-2-oxo-1,2-dihydropyridine-3,5-dicarboxamide;
1-benzyl-N5-(2-hydroxypropyl)-N3-methyl-2-oxo-1,2-dihydropyridine-3,5-dicarboxamide;
1-benzyl-N5-(3-hydroxypropyl)-N3-methyl-2-oxo-1,2-dihydropyridine-3,5-dicarboxamide;
1-benzyl-N5-(3-(dimethylamino)butyl)-N3-methyl-2-oxo-1,2-dihydropyridine-3,5-dicarboxamide;
1-benzyl-N3-methyl-2-oxo-N5-(2-(pyridin-4-yl)ethyl)-1,2-dihydropyridine-3,5-dicarboxamide;
1-benzyl-N3-methyl-N5-(3-(methylamino)-3-oxopropyl)-2-oxo-1,2-dihydropyridine-3,5-dicarboxamide;
1-benzyl-N5-(3-cyanopropyl)-N3-methyl-2-oxo-1,2-dihydropyridine-3,5-dicarboxamide;
1-benzyl-N5-(2-cyanoethyl)-N3-methyl-2-oxo-1,2-dihydropyridine-3,5-dicarboxamide;
N5-(3-aminopropyl)-1-benzyl-N3-methyl-2-oxo-1,2-dihydropyridine-3,5-dicarboxamide;
1-benzyl-N5-(3-hydroxybutyl)-N3-methyl-2-oxo-1,2-dihydropyridine-3,5-dicarboxamide;
1-benzyl-N3-methyl-2-oxo-N5-(2-(pyridin-3-yl)ethyl)-1,2-dihydropyridine-3,5-dicarboxamide;
1-benzyl-N5-(2-methoxyethyl)-N3-methyl-2-oxo-1,2-dihydropyridine-3,5-dicarboxamide;
1-benzyl-N5-(3-methoxypropyl)-N3-methyl-2-oxo-1,2-dihydropyridine-3,5-dicarboxamide;
1-(3-cyanobenzyl)-N3,N5-dimethyl-2-oxo-1,2-dihydropyridine-3,5-dicarboxamide;
4-(1-benzyl-5-(methylcarbamoyl)-6-oxo-1,6-dihydropyridine-3-carboxamido)butanoic acid;
1-benzyl-N3-methyl-N5-(2-(methylsulfonyl)ethyl)-2-oxo-1,2-dihydropyridine-3,5-dicarboxamide;
1-benzyl-N5-(2-hydroxyethyl)-N3-methyl-2-oxo-1,2-dihydropyridine-3,5-dicarboxamide;
1-benzyl-N5-(3-(dimethylamino)propyl)-N3-methyl-2-oxo-1,2-dihydropyridine-3,5-dicarboxamide;
1-benzyl-N3-methyl-N5-(3-(methylsulfonyl)propyl)-2-oxo-1,2-dihydropyridine-3,5-dicarboxamide;
N5-(2-(1H-imidazol-4-yl)ethyl)-1-(2-fluoro-3-methylbenzyl)-N3-methyl-2-oxo-1,2-dihydropyridine-3,5-dicarboxamide;
N5-(2-(1H-pyrazol-5-yl)ethyl)-1-benzyl-N3-methyl-2-oxo-1,2-dihydropyridine-3,5-dicarboxamide;
1-benzyl-N3-methyl-N5-(1-methyl-1H-pyrazol-3-yl)-2-oxo-1,2-dihydropyridine-3,5-dicarboxamide;
1-benzyl-N3-methyl-N5-(2-(1-methyl-1H-pyrazol-4-yl)ethyl)-2-oxo-1,2-dihydropyridine-3,5-dicarboxamide;
1-benzyl-N3-methyl-N5-(1-methyl-1H-pyrazol-4-yl)-2-oxo-1,2-dihydropyridine-3,5-dicarboxamide;

1-benzyl-N3-methyl-N5-(2-(4-methyl-4H-1,2,4-triazol-3-yl)ethyl)-2-oxo-1,2-dihydropyridine-3,5-dicarboxamide;

1-benzyl-N3-methyl-N5-(2-(4-methylthiazol-5-yl)ethyl)-2-oxo-1,2-dihydropyridine-3,5-dicarboxamide;

1-benzyl-N3-methyl-2-oxo-N5-(2-(thiazol-4-yl)ethyl)-1,2-dihydropyridine-3,5-dicarboxamide;

1-benzyl-N5-(2-(isoxazol-4-yl)ethyl)-N3-methyl-2-oxo-1,2-dihydropyridine-3,5-dicarboxamide; and 1-benzyl-N3-methyl-2-oxo-N5-(pyridazin-4-yl)-1,2-dihydropyridine-3,5-dicarboxamide;

or a pharmaceutically acceptable salt thereof.

15. A pharmaceutical composition comprising the compound or pharmaceutically acceptable salt thereof according to claim 1 and a pharmaceutically acceptable excipient.

16. A combination comprising the compound or pharmaceutically acceptable salt thereof according to claim 1 together with one or more other therapeutically active agents.

17. A method of treating a bromodomain-mediated disease or condition in a human in need thereof comprising administering a therapeutically effective amount of the compound, or pharmaceutically acceptable salt thereof, according to claim 1.

18. The method according to claim 17, wherein the bromodomain-mediated disease or condition is an acute and/or chronic autoimmune or inflammatory condition.

19. The method according to claim 18, wherein the acute or chronic autoimmune and/or inflammatory condition is rheumatoid arthritis.

20. A method of treating a bromodomain-mediated disease or condition in a human in need thereof comprising administering a therapeutically effective amount to the human a combination comprising the compound, or a pharmaceutically acceptable salt, according to claim 1, wherein the disease or condition is an acute and/or chronic autoimmune or inflammatory condition.

21. A method of treating a bromodomain-mediated disease or condition in a human in need thereof comprising administering a therapeutically effective amount to the human a combination comprising the compound, or a pharmaceutically acceptable salt, according to claim 1, wherein the disease or condition is rheumatoid arthritis.

* * * * *